(12) United States Patent
Galvin et al.

(10) Patent No.: US 11,472,831 B2
(45) Date of Patent: Oct. 18, 2022

(54) ISOTOPICALLY LABELED BILE ACID DERIVATIVES

(71) Applicant: Intercept Pharmaceuticals, Inc., New York, NY (US)

(72) Inventors: Gabriel Galvin, San Diego, CA (US); Kevin Schaab, San Diego, CA (US); Mathew Yanik, San Diego, CA (US)

(73) Assignee: Intercept Pharmaceuticals, Inc., Morristown, NJ (US)

( * ) Notice: Subject to any disclaimer, the term of this patent is extended or adjusted under 35 U.S.C. 154(b) by 58 days.

(21) Appl. No.: 16/632,093

(22) PCT Filed: Jul. 23, 2018

(86) PCT No.: PCT/US2018/043239
§ 371 (c)(1),
(2) Date: Jan. 17, 2020

(87) PCT Pub. No.: WO2019/023103
PCT Pub. Date: Jan. 31, 2019

(65) Prior Publication Data
US 2020/0165290 A1 May 28, 2020

Related U.S. Application Data

(60) Provisional application No. 62/536,609, filed on Jul. 25, 2017, provisional application No. 62/536,326, filed on Jul. 24, 2017.

(51) Int. Cl.
| C07J 41/00 | (2006.01) |
| C07J 9/00 | (2006.01) |
| C07J 17/00 | (2006.01) |

(52) U.S. Cl.
CPC ........... *C07J 41/0061* (2013.01); *C07J 9/005* (2013.01); *C07J 17/005* (2013.01); *C07B 2200/05* (2013.01)

(58) Field of Classification Search
CPC ...... C07J 41/0061; C07J 9/005; C07J 17/005; C07J 41/0094; C07J 51/00; C07J 9/00; C07B 2200/05
See application file for complete search history.

(56) References Cited

U.S. PATENT DOCUMENTS

| 7,932,244 B2 | 4/2011 | Pellicciari et al. |
| 8,114,862 B2 | 2/2012 | Pellicciari |
| 9,238,673 B2 | 1/2016 | Steiner et al. |
| 9,611,289 B2 | 4/2017 | Pellicciari |
| 2015/0112089 A1 | 4/2015 | Finch et al. |
| 2015/0291653 A1 | 10/2015 | Pellicciari et al. |
| 2017/0035784 A1 | 2/2017 | Lancaster et al. |

FOREIGN PATENT DOCUMENTS

| CN | 106 008 639 A | 10/2016 |
| EP | 3260463 A1 | 12/2017 |
| WO | WO 2002/075298 A2 | 9/2002 |
| WO | WO 2013/192097 A1 | 12/2013 |
| WO | WO 2014/066819 A1 | 5/2014 |
| WO | WO 2016/131414 A1 | 8/2016 |
| WO | WO 2016/168553 A1 | 10/2016 |
| WO | WO 2017/062763 A1 | 4/2017 |
| WO | WO 2017/147159 A1 | 8/2017 |

OTHER PUBLICATIONS

Gai, Kuo et al. "Synthesis of obeticholic acid, a farnesoid X receptor agonist, and its major metabolites labeled with deuterium", Journal of Labelled Compounds and Radiopharmaceuticals, vol. 61, No. 10, 2018, pp. 799-804.
Thomas et al. "Targeting bile-acid signalling for metabolic diseases", Nature Reviews | Drug Discovery, 2008, vol. 7, p. 678-693.
Ren S. et al. "An improved synthesis of [24-14C]cholic acid, and its application to the synthesis of [14C]SCH 209702 (Syn3). Synthesis of [2H8]SCH 209702", Journal of Labelled Compounds and Radiopharmaceuticals, (2008) 51: 231-235.

*Primary Examiner* — Susanna Moore

(57) ABSTRACT

The present application relates to isotopically labeled compounds of Formula I and methods of preparation and use thereof.

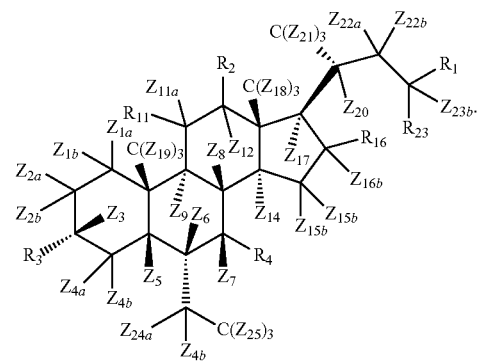

15 Claims, 18 Drawing Sheets

ISOTOPICALLY LABELED BILE ACID DERIVATIVES

BACKGROUND

Selective incorporation of isotopes (e.g., deuterium in place of hydrogen) has a unique effect of retaining the biochemical potency and selectivity of physiologically active compounds while modifying metabolic properties to alter their overall therapeutic profile. In some cases, this modification has the potential to have a positive impact on safety, efficacy and tolerability. Isotopically labeled (e.g., deuterated and/or radiolabeled) compounds have been widely studied in clinical and non-clinical settings and used in humans as metabolic or pharmacokinetic probes.

Bile acids (BAs) are well known for their role in the solubilization and digestion of lipid-soluble nutrients. Recently, BAs have emerged as signaling molecules with systemic endocrine functions. BAs and derivatives thereof have been shown to modulate several nuclear hormone receptors, notably the farnesoid X receptor (FXR), and are agonists for the G protein-coupled receptor TGR5. Signaling via FXR and TGR5 modulates several metabolic pathways, regulating not only BA synthesis and enterohepatic recirculation, but also triglyceride, cholesterol, glucose and energy homeostasis (Thomas, et al. Nat Rev Drug Discovery, 2008, 7, 678-693).

A semi-synthetic bile acid analogue, 3α,7α-dihydroxy-6α-ethyl-5β-cholan-24-oic acid (6-ethyl-chenodeoxycholic acid (6-ECDCA) or obeticholic acid (OCA)), disclosed in WO 2002/75298 is a highly potent FXR modulator, which is currently marketed as OCALIVA® for the treatment of primary biliary cholangitis (PBC).

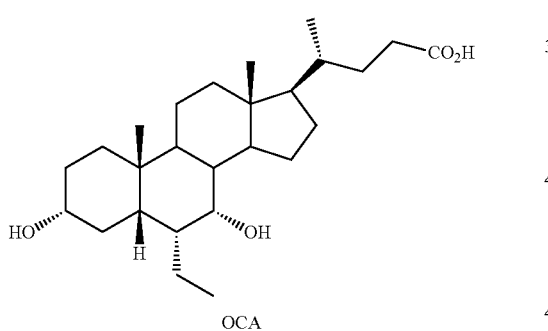

OCA

Another semi-synthetic bile acid analogue, 3α,7α, 11β-trihydroxy-6α-ethyl-5β-cholan-24-oic acid (compound 100) while being a potent FXR agonist, also showed specificity against G protein-coupled receptor TGR5 (GP-BAR1, M-BAR, GPBAR, or GPR131).

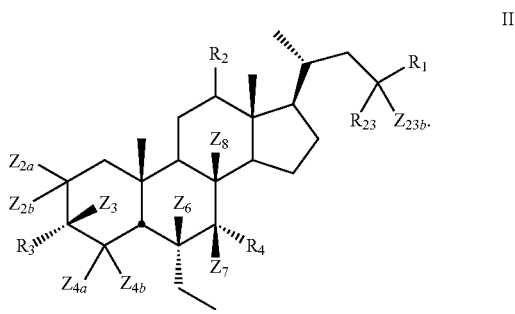

100

Accordingly, new isotopically labeled bile acid derivatives are needed to further investigate the important medical benefits of this class of compounds and enhance their clinical safety, tolerability and/or efficacy.

SUMMARY

The present disclosure relates to isotopically labeled (e.g., deuterated and/or radiolabeled) derivatives of obeticholic acid including amino acid conjugates and glucuronides thereof.

In some of the embodiments the present disclosure pertains to a compound of Formula I.

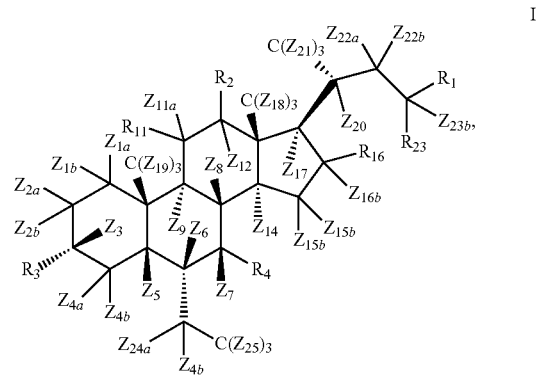

I or a pharmaceutically acceptable salt thereof, wherein $R_1$, $R_2$, $R_3$, $R_4$, $R_5$, $R_6$, $R_{11}$, $R_{16}$, $R_{23}$, $Z_{1a}$, $Z_{1b}$, $Z_{2a}$, $Z_{2b}$, $Z_3$, $Z_{4a}$, $Z_{4b}$, $Z_5$, $Z_6$, $Z_7$, $Z_8$, $Z_9$, $Z_{11a}$, $Z_{11b}$, $Z_{12}$, $Z_{14}$, $Z_{15a}$, $Z_{15b}$, $Z_{16a}$, $Z_{16b}$, $Z_{17}$, $Z_{18}$, $Z_{19}$, $Z_{20}$, $Z_{21}$, $Z_{22a}$, $Z_{22b}$, $Z_{23a}$, $Z_{23b}$, $Z_{24a}$, $Z_{24b}$, and $Z_{25}$ are as described herein.

In some embodiments, the present disclosure relates to a compound of Formula II

II

Some embodiments of the present disclosure relate to a compound of Formula III

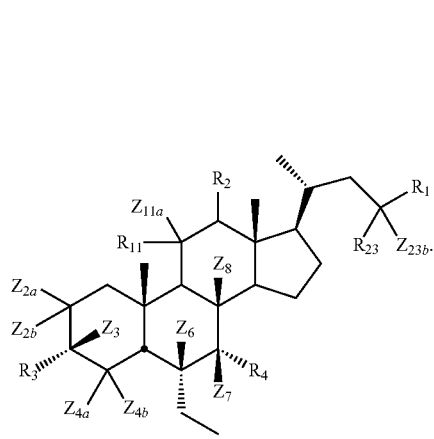

III

In some embodiments, the present disclosure relates to a compound of Formula IV

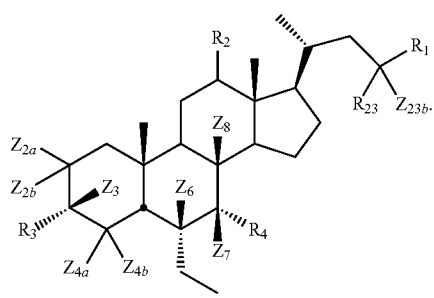

IV

In some embodiments, the present disclosure relates to a compound of Formula V

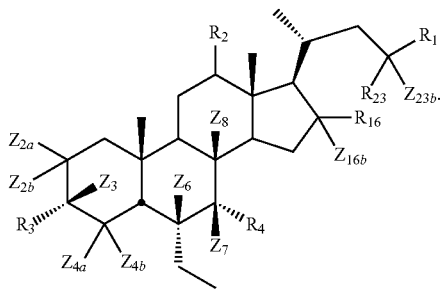

V

In some embodiments, the present disclosure relates to compounds of Formula VI

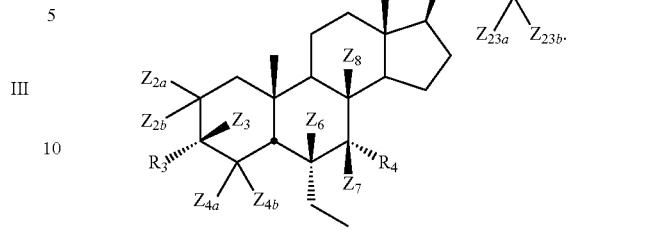

VI

In some embodiments, the present disclosure relates to compounds of Formula VII

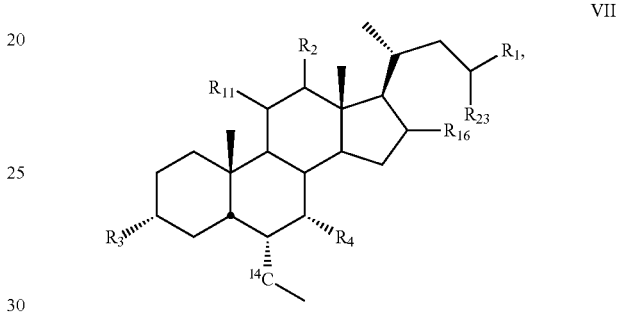

VII wherein
$R_1$, $R_2$, $R_3$, $R_4$, $R_{11}$, $R_{16}$, and $R_{23}$ are as described above.
In some embodiments, the present disclosure relates to a process for preparing the compounds of Formula I.

Some embodiments of the present disclosure pertain to a pharmaceutical composition comprising the compound of Formula I and a pharmaceutically acceptable diluent, excipient or carrier.

Some embodiments of the present disclosure pertain to a method of modulating FXR activity in a subject in need thereof, comprising administering a therapeutically effective amount of the compound of Formula I.

Some embodiments of the present disclosure pertain to a method of modulating TGR5 activity in a subject in need thereof, comprising administering a therapeutically effective amount of the compound of Formula I.

Unless otherwise defined, all technical and scientific terms used herein have the same meaning as commonly understood by one of ordinary skill in the art to which this application belongs. In the specification, the singular forms also include the plural unless the context clearly dictates otherwise. Although methods and materials similar or equivalent to those described herein can be used in the practice or testing of the present application, suitable methods and materials are described below. All publications, patent applications, patents, and other references mentioned herein are incorporated by reference. The references cited herein are not admitted to be prior art. In the case of conflict, the present specification, including definitions, will control. In addition, the materials, methods, and examples are illustrative only and are not intended to be limiting.

Other features and advantages of the application will be apparent from the following detailed description and claims.

DETAILED DESCRIPTION

Definitions

Figure 1:
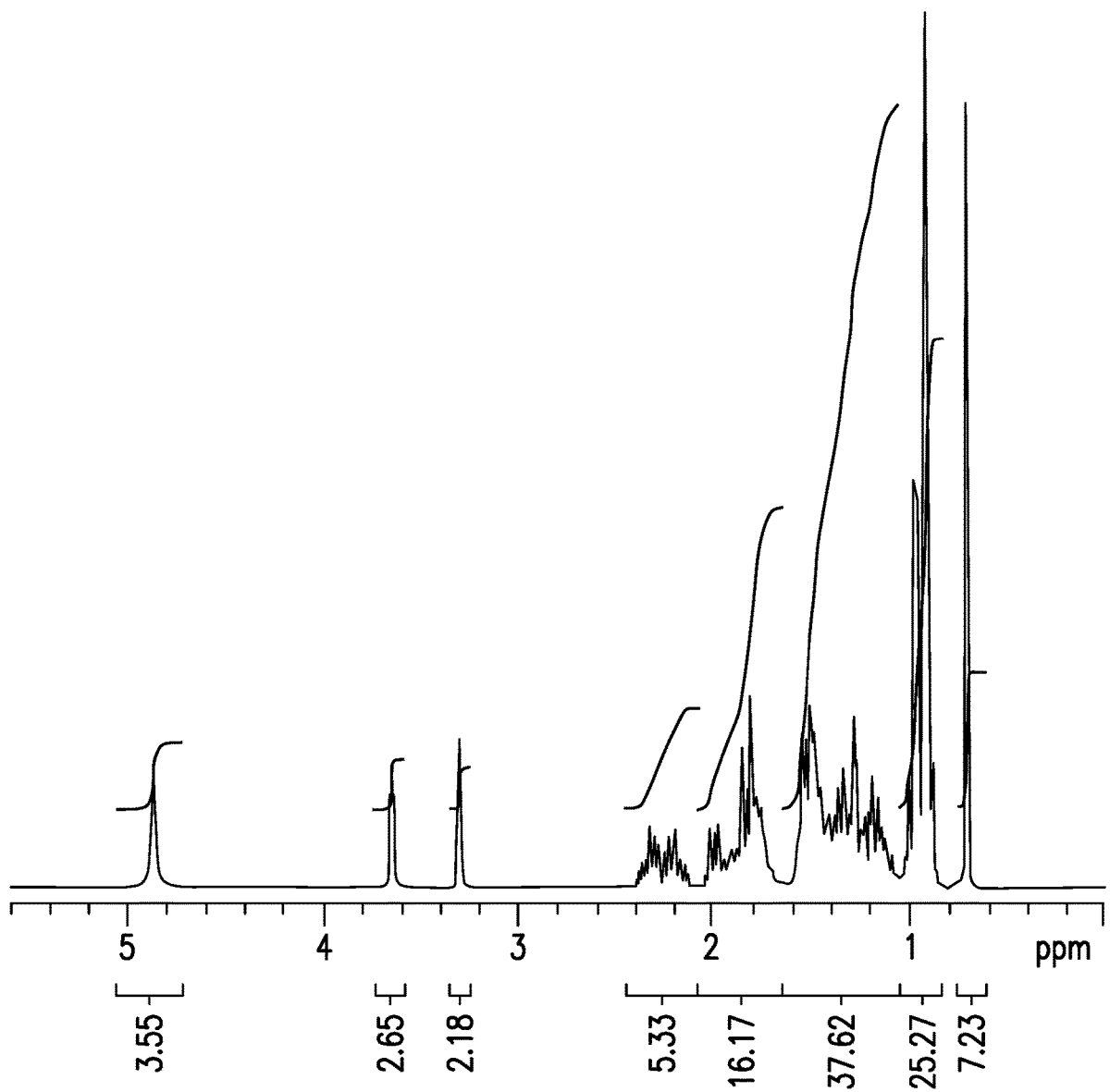
FIG. 1 shows the $^1$H NMR spectrum obtained from $d_5$-OCA.

As used in this disclosure and the accompanying claims, the indefinite articles "a" and "an" and the definite article "the" include plural as well as single referents, unless the context clearly indicates otherwise.

As used herein, the phrase "a compound of the invention" refers to a compound of any one of Formula I, II, III, IV, V, VI, VII or VIII or any compound explicitly disclosed herein.

The present disclosure relates to isotopically-labeled compounds of Formula I, wherein one or more atoms are replaced by an atom having an atomic mass or mass number different from the atomic mass or mass number usually found in nature. Examples of isotopes that can be incorporated into compounds of the disclosure include isotopes of hydrogen, carbon, nitrogen, and oxygen. Unless otherwise stated, when a position is designated specifically as "H" or "hydrogen", the position is understood to have hydrogen at its natural abundance isotopic composition or its isotopes, such as deuterium (d, d, D, or $^2$H) or tritium ($^3$H).

In some embodiments, isotopically labeled compounds of the present disclosure (e.g., those labeled with $^2$H, $^3$H and/or $^{14}$C or $^{13}$C) are useful in compound and/or substrate tissue distribution assays. Tritiated (i.e., $^3$H) and carbon-14 (i.e., $^{14}$C) isotopes are useful for their ease of preparation and detectability. Further, substitution with heavier isotopes such as deuterium (i.e., $^2$H or d) may afford certain therapeutic advantages resulting from greater metabolic stability (e.g., increased in vivo half-life or reduced dosage requirements) and hence may be preferred in some circumstances. In some embodiments, in isotopically labeled compounds of the present disclosure any carbon can be $^{11}$C, $^{12}$C, $^{13}$C, or $^{14}$C, any nitrogen atom can be $^{13}$N, $^{14}$N or $^{15}$N, and any oxygen atom can be $^{15}$O, $^{16}$O, $^{17}$O, or $^{18}$O.

Deuterium is a safe, nonradioactive relative of hydrogen that can be isolated from sea water and has been used extensively in human metabolic and clinical studies. The average adult human body contains about 1-2 grams of deuterium due to its general abundance in nature.

The term "deuterated" as used herein alone or as part of a group, means substituted deuterium atoms. The term "deuterated analog" or "deuterated compound" as used herein alone or as part of a group, means substituted deuterium atoms in place of hydrogen. The deuterated analog of the disclosure may be a fully or partially deuterium substituted derivative. In some embodiments, the deuterium substituted derivative of the disclosure holds a fully or partially deuterated substituent, e.g., alkyl group.

A deuterated drug is a medicinal product (e.g., compound of Formula I) in which one or more of the hydrogen atoms contained in the drug molecule have been replaced by deuterium. A compound of the invention or a pharmaceutically acceptable salt or solvate thereof that contains the aforementioned deuterium atom(s) is within the scope of the invention. Further, substitution with heavier deuterium, i.e., 2H, can afford certain therapeutic advantages resulting from greater metabolic stability, for example increased in vivo half-life or reduced dosage requirements. Isotopically labeled compounds of the present disclosure can generally be prepared by following procedures analogous to those described herein, including Schemes and Examples disclosed herein, by substituting an isotopically labeled reagent for a non-isotopically labeled reagent.

Deuterium-containing drugs, because of the kinetic isotope effect, may have significantly lower rates of metabolism, and hence a longer half-life. The present invention also comprehends deuterium labeled compounds of Formula I where one or more hydrogen atoms is replaced by a deuterium atom having an abundance of deuterium at that position that is substantially greater than the natural abundance of deuterium, which is 0.015%.

The term "deuterium enrichment factor" as used herein means the ratio between the deuterium abundance and the natural abundance of a deuterium. In one aspect, a compound of the invention has a deuterium enrichment factor for each deuterium atom of at least 3500 (52.5% deuterium incorporation at each deuterium atom), at least 4000 (60% deuterium incorporation), at least 4500 (67.5% deuterium incorporation), at least 5000 (75% deuterium), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation).

"Specific activity" as used herein means the activity per quantity of a radionuclide and is a physical property of that radionuclide. Activity is a quantity related to radioactivity. The SI unit of activity is the becquerel (Bq), equal to one reciprocal second. The becquerel is how many radioactive transformations per second occur in a radioactive isotope. Its related and more common unit is the Curie (abbreviated Ci) which is $3.7 \times 10^{10}$ transformations per second. Since the probability of radioactive decay for a given radionuclide is a fixed physical quantity (with some slight exceptions, see Changing decay rates), the number of decays that occur in a given time of a specific number of atoms of that radionuclide is also a fixed physical quantity (if there are large enough numbers of atoms to ignore statistical fluctuations). Thus, specific activity is defined as the activity per quantity of atoms of a particular radionuclide. It is usually given in units of Bq/g, but another commonly used unit of activity is the curie (Ci) allowing the definition of specific activity in Ci/g.

The term "alkyl" by itself or as part of another substituent, means, unless otherwise stated, a straight or branched chain hydrocarbon, having the number of carbon atoms designated (i.e. $C_{1-6}$ meaning one to six carbons). Representative alkyl groups include straight and branched chain alkyl groups having 1, 2, 3, 4, 5, 6, 7 or 8 carbon atoms. Examples of alkyl groups include methyl, ethyl, n-propyl, isopropyl, n-butyl, t-butyl, isobutyl, sec-butyl, n-pentyl, n-hexyl, n-heptyl, n-octyl, and the like. The term "deuteroalkyl" refers to a deuterated analog of an alkyl group.

"Optional" or "Optionally" as used throughout the disclosure means that the subsequently described event or circumstance may or may not occur, and that the description includes instances where the event or circumstance occurs and instances in which it does not. For example, the phrase "the alkyl group is optionally substituted with one or two substituents" means that the substituent may but need not be present, and the description includes situations where the alkyl group is substituted and situations where the alkyl group is not substituted.

It will be noted that the structure of some of the compounds of the invention include asymmetric carbon atoms. It is to be understood accordingly that the isomers arising from such asymmetry (e.g., all enantiomers and diastereomers) are included within the scope of the disclosure, unless indicated otherwise. Such isomers can be obtained in substantially pure form by classical separation techniques and by stereochemically controlled synthesis. Enantiomers (R- and S-configurations) are named according to the system developed by R. S. Cahn, C. Ingold, and V. Prelog.

As used herein, "pharmaceutically acceptable salts" refer to derivatives of a compound of the invention wherein the parent compound is modified by forming acid or base salts thereof. Examples of pharmaceutically acceptable salts include, but are not limited to, mineral or organic acid salts of basic residues such as amines; alkali (basic) or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. Common salt-forming cations in basic salts include but are not limited to sodium $Na^+$, potassium $K^+$, calcium $Ca^{2+}$, magnesium $Mg^{2+}$, ammonium $NH_4^+$, quaternary ammonium $NR_4^+$, where R can be an alkyl.

For example, such conventional non-toxic acid salts include, but are not limited to, those derived from inorganic and organic acids selected from 2-acetoxybenzoic, 2-hydroxyethane sulfonic, acetic, ascorbic, benzene sulfonic, benzoic, bicarbonic, carbonic, citric, edetic, ethane disulfonic, fumaric, glucoheptonic, gluconic, glutamic, glycolic, glycollyarsanilic, hexylresorcinic, hydrabamic, hydrobromic, hydrochloric, hydroiodide, hydroxymaleic, hydroxynaphthoic, isethionic, lactic, lactobionic, lauryl sulfonic, maleic, malic, mandelic, methane sulfonic, napsylic, nitric, oxalic, pamoic, pantothenic, phenylacetic, phosphoric, polygalacturonic, propionic, salicylic, stearic, subacetic, succinic, sulphamic, sulphanilic, sulphuric, tannic, tartaric, and toluene sulphonic.

"Solvate", as used herein, refers to a solvent addition form of a compound of the invention that contains either stoichiometric or non-stoichiometric amounts of solvent. Some compounds have a tendency to trap a fixed molar ratio of solvent molecules in the crystalline solid state, thus forming a solvate. If the solvent is water, the solvate formed is a hydrate, and when the solvent is alcohol, the solvate formed is an alcoholate. Hydrates are formed by the combination of one or more molecules of water with one of the substances in which the water retains its molecular state as $H_2O$, such combination being able to form one or more hydrate.

The term "tautomer" as used herein means compounds produced by the phenomenon wherein a proton of one atom of a molecule shifts to another atom. See, Jerry March, Advanced Organic Chemistry: Reactions, Mechanisms and Structures, Fourth Edition, John Wiley & Sons, pages 69-74 (1992). The tautomers also refer to one of two or more structural isomers that exist in equilibrium and are readily converted from one isomeric form to another. Examples of include keto-enol tautomers, such as acetone/propen-2-ol, imine-enamine tautomers and the like, ring-chain tautomers, such as glucose/2,3,4,5,6-pentahydroxy-hexanal and the like, the tautomeric forms of heteroaryl groups containing a —N=C(H)—NH— ring atom arrangement, such as pyrazoles, imidazoles, benzimidazoles, triazoles, and tetrazoles. Where the compound contains, for example, a keto or oxime group or an aromatic moiety, tautomeric isomerism ('tautomerism') can occur. The compounds described herein may have one or more tautomers and therefore include various isomers. A person of ordinary skill in the art would recognize that other tautomeric ring atom arrangements are possible. All such isomeric forms of these compounds are expressly included in the present disclosure.

The term "isomers" means compounds having identical molecular formula but differ in the nature or sequence of bonding of their atoms or in the arrangement of their atoms in space. Isomers that differ in the arrangement of their atoms in space are termed "stereoisomers". "Stereoisomer" and "stereoisomers" refer to compounds that exist in different stereoisomeric forms if they possess one or more asymmetric centers or a double bond with asymmetric substitution and, therefore, can be produced as individual stereoisomers or as mixtures. Stereoisomers include enantiomers and diastereomers. Stereoisomers that are not mirror images of one another are termed "diastereomers" and those that are non-superimposable mirror images of each other are termed "enantiomers". When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture". Unless otherwise indicated, the description is intended to include individual stereoisomers as well as mixtures. The methods for the determination of stereochemistry and the separation of stereoisomers are well-known in the art (see discussion in Chapter 4 of ADVANCED ORGANIC CHEMISTRY, 6th edition J. March, John Wiley and Sons, New York, 2007) differ in the chirality of one or more stereocenters.

The term "prodrugs" as used herein means any compound which releases a biologically active compound or drug in vivo when such prodrug is administered to a subject. Prodrugs of a compound of Formula I are prepared by modifying functional groups present in the compound of Formula I in such a way that the modifications may be cleaved in vivo to release the active compound. Prodrugs may be prepared by modifying functional groups present in the compounds in such a way that the modifications are cleaved, either in routine manipulation or in vivo, to the active compounds. Prodrugs include compounds of Formula I wherein a hydroxy, amino, carboxyl or sulfonyl group in a compound of Formula I is bonded to any group that may be cleaved in vivo to regenerate the free hydroxyl, amino, or sulfonate group, respectively. Examples of prodrugs include, but are not limited to esters (e.g., acetate, formate, and benzoate derivatives), amides, guanidines, carbamates (e.g., N,N-dimethylaminocarbonyl) of hydroxy functional groups in compounds of Formula I, and the like. Preparation, selection, and use of prodrugs is discussed in T. Higuchi and V. Stella, "Pro-drugs as Novel Delivery Systems," Vol. 14 of the A.C.S. Symposium Series; "Design of Prodrugs", ed. H. Bundgaard, Elsevier, 1985; and in Bioreversible Carriers in Drug Design, ed. Edward B. Roche, American Pharmaceutical Association and Pergamon Press, 1987, each of which are hereby incorporated by reference in their entirety.

As defined herein, the term "metabolite" can refer to amino acid conjugates, glucuronidated and sulphated derivatives of the compounds described herein, wherein one or more amino acid, glucuronic acid or sulphate moieties are linked to compound of the invention. Sulphated derivatives of the compounds may be formed through sulphation of the hydroxyl groups (e.g., 3-hydroxyl, 7-hydroxyl, 11-hydroxyl, and/or the hydroxyl of the $R_7$ group). Examples of such metabolites include, but are not limited to 3-sulphate, 7-sulphate, 11-sulphate, 3,7-bisulphate, 3,11-bisulphate, 7,11-bisulphate, and 3,7,11-trisulphate of the compounds described herein.

As used herein, the term "amino acid conjugates" refers to conjugates of a compound of the invention with any suitable amino acid. Taurine (—NH(CH$_2$)$_2$SO$_3$H), glycine (—NHCH$_2$CO$_2$H), and sarcosine (—N(CH$_3$)CH$_2$CO$_2$H) are examples of amino acid conjugates. Suitable amino acid conjugates of the compounds have the added advantage of enhanced integrity in bile or intestinal fluids. Suitable amino acids are not limited to taurine, glycine, and sarcosine.

As defined herein, the term "glucuronides" refers to glucuronidated derivatives of the compounds described herein, wherein one or more glucuronic acid linked to compound of the disclosure. Glucuronic acid moieties may be linked to the compounds through glycosidic bonds with the hydroxyl groups of the compounds (e.g., 3-hydroxyl, 7-hydroxyl, 11-hydroxyl, 12-hydroxyl, and/or the hydroxyl of the $R^1$ group). Examples of glucuronides of Compound of Formula I include, but are not limited to, 3-O-glucuronides, 7-O-glucuronides, 12-O-glucuronides, 3-O-7-O-diglucuronides, 3-O-12-O-triglucuronides, 7-O-12-O-triglucuronides, and 3-O-7-O-12-O-triglucuronides.

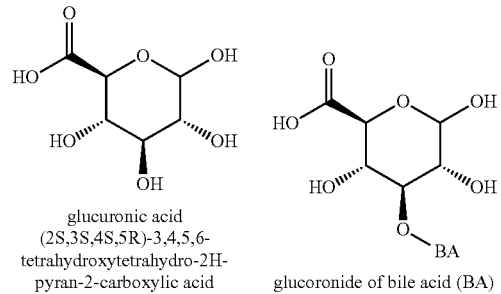

glucuronic acid
(2S,3S,4S,5R)-3,4,5,6-tetrahydroxytetrahydro-2H-pyran-2-carboxylic acid glucoronide of bile acid (BA)

As defined herein, the terms "sulphated derivatives" and/or "sulphates" relate to the compounds described herein, wherein one or more sulphate moieties are linked to compound of the disclosure. Sulphated derivatives of the compounds may be formed through sulphation of the hydroxyl groups (e.g., 3-hydroxyl, 7-hydroxyl, 11-hydroxyl, 12-hydroxyl, and/or the hydroxyl of the $R^1$ group). Examples of sulphated derivatives of compound of Formula I include, but are not limited to 3-sulphates, 7-sulphates, 11-sulphates, 12-sulphates, 3,7-bisulphates, 3,12-bisulphates, 7,12-bisulphates, and 3,7,12-trisulphates and other combinations thereof.

A "composition" or "pharmaceutical composition" is a formulation containing a compound of the invention or a salt, solvate, or amino acid conjugate thereof. In one embodiment, the pharmaceutical composition is in bulk or in unit dosage form. The unit dosage form is any of a variety of forms, including, for example, a capsule, an IV bag, a tablet, a single pump on an aerosol inhaler, or a vial. The quantity of active ingredient (e.g., a formulation of a compound of the invention or salts thereof) in a unit dose of composition is an effective amount and is varied according to the particular treatment involved. One skilled in the art will appreciate that it may be necessary to make routine variations to the dosage depending on the age and condition of the patient. The dosage will also depend on the route of administration. A variety of routes are contemplated, including oral, ocular, ophthalmic, pulmonary, rectal, parenteral, transdermal, subcutaneous, intravenous, intramuscular, intraperitoneal, intranasal, and the like. Dosage forms for the topical or transdermal administration of a compound of this application include powders, sprays, ointments, pastes, creams, lotions, gels, solutions, patches and inhalants. In another embodiment, the active compound is mixed under sterile conditions with a pharmaceutically acceptable carrier, and with any preservatives, buffers, or propellants that are required.

The phrase "pharmaceutically acceptable carrier" is art-recognized, and includes, for example, pharmaceutically acceptable materials, compositions or vehicles, such as a liquid or solid filler, diluent, excipient, solvent or encapsulating material, involved in carrying or transporting any subject composition from one organ, or portion of the body, to another organ, or portion of the body. Each carrier is "acceptable" in the sense of being compatible with the other ingredients of a subject composition and not injurious to the patient. In certain embodiments, a pharmaceutically acceptable carrier is non-pyrogenic. Some examples of materials which may serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, sunflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

The term "treating", as used herein, refers to relieving, lessening, reducing, eliminating, modulating, or ameliorating, i.e., causing regression of the disease state or condition.

The term "preventing", as used herein, refers to completely or almost completely stop a disease state or condition, from occurring in a patient or subject, especially when the patient or subject is predisposed to such or at risk of contracting a disease state or condition. Preventing can also include inhibiting, i.e., arresting the development, of a disease state or condition, and relieving or ameliorating, i.e., causing regression of the disease state or condition, for example when the disease state or condition may already be present.

The phrase "reducing the risk of", as used herein, refers to lowering the likelihood or probability of a central nervous system disease, inflammatory disease and/or metabolic disease from occurring in a patient, especially when the subject is predisposed to such occurrence.

As used herein, the term "modulating" or "modulate" or the like refers to an effect of altering a biological activity, especially a biological activity associated with a particular biomolecule (e.g., receptor or enzyme). For example, an agonist or antagonist of a particular biomolecule modulates the activity of that biomolecule by either increasing (e.g. agonist, activator), or decreasing (e.g. antagonist, inhibitor) the activity of the biomolecule. Such activity is typically indicated in terms of an inhibitory concentration ($IC_{50}$) or effective concentration ($EC_{50}$) of the compound for an inhibitor or activator, respectively, with respect to, for example, a receptor or an enzyme.

"Combination therapy" (or "co-therapy") refers to the administration of a compound of the invention and at least a second agent as part of a specific treatment regimen intended to provide the beneficial effect from the co-action of these therapeutic agents (i.e., the compound of the invention and at least a second agent). The beneficial effect of the combination includes, but is not limited to, pharmacokinetic or pharmacodynamic co-action resulting from the combination of therapeutic agents. Administration of these therapeutic agents in combination typically is carried out over a defined time periods (usually minutes, hours, days or weeks depending upon the combination selected). "Combination therapy" may, but generally is not, intended to encompass the administration of two or more of these therapeutic agents as part of separate monotherapy regimens that incidentally and arbitrarily result in the combinations of the present application. "Combination therapy" is intended to embrace administration of these therapeutic agents in a sequential manner, that is, wherein each therapeutic agent is administered at a different time, as well as administration of these therapeutic agents, or at least two of the therapeutic agents, in a substantially simultaneous manner. Substantially simultaneous administration can be accomplished, for example, by administering to the subject a single capsule having a fixed ratio of each therapeutic agent or in multiple, single capsules for each of the therapeutic agents. Sequential or substantially simultaneous administration of each therapeutic agent can be effected by any appropriate route including, but not limited to, oral routes, intravenous routes, intramuscular routes, and direct absorption through mucous membrane tissues. The therapeutic agents can be administered by the same route or by different routes. For example, a first therapeutic agent of the combination selected may be administered by intravenous injection while the other therapeutic agents of the combination may be administered orally. Alternatively, for example, all therapeutic agents may be administered orally or all therapeutic agents may be administered by intravenous injection. The sequence in which the therapeutic agents are administered is not narrowly critical.

"Combination therapy" also embraces the administration of the therapeutic agents as described above in further combination with other biologically active ingredients and non-drug therapies (e.g., surgery or mechanical treatments). Where the combination therapy further comprises a non-drug treatment, the non-drug treatment may be conducted at any suitable time so long as a beneficial effect from the co-action of the combination of the therapeutic agents and non-drug treatment is achieved. For example, in appropriate cases, the beneficial effect is still achieved when the non-drug treatment is temporally removed from the administration of the therapeutic agents, perhaps by days or even weeks.

An "effective amount" of a compound of the invention, or a combination of compounds is an amount (quantity or concentration) of compound or compounds. In one embodiment, when a therapeutically effective amount of a compound is administered to a subject in need of treatment symptoms arising from the disease are ameliorated immediately or after administration of the compound one or more times. The amount of the compound to be administered to a subject will depend on the specific disorder, the mode of administration, co-administered compounds, if any, and the characteristics of the subject, such as general health, other diseases, age, sex, genotype, body weight, and tolerance to drugs. The skilled artisan will be able to determine appropriate dosages depending on these and other factors. For any compound, the therapeutically effective amount can be estimated initially either in cell culture assays, e.g., of neoplastic cells, or in animal models, usually rats, mice, rabbits, dogs, or pigs. The animal model may also be used to determine the appropriate concentration range and route of administration. Such information can then be used to determine useful doses and routes for administration in humans.

The term "prophylactically effective amount" means an amount (quantity or concentration) of a compound of the present invention, or a combination of compounds, that is administered to prevent or reduce the risk of a disease—in other words, an amount needed to provide a preventative or prophylactic effect. Therapeutic/prophylactic efficacy and toxicity may be determined by standard pharmaceutical procedures, e.g., $ED_{50}$ (the dose therapeutically effective in 50% of the population) and $LD_{50}$ (the dose lethal to 50% of the population). The dose ratio between toxic and therapeutic effects is the therapeutic index, and it can be expressed as the ratio, $LD_{50}/ED_{50}$. Pharmaceutical compositions that exhibit large therapeutic indices are preferred. The dosage may vary depending upon various factors, including but not limited to the dosage form employed, sensitivity of the patient, and the route of administration.

The amount of the present compound to be administered to a subject will depend on a particular disorder, mode of administration, co-administered compounds, if any, and the characteristics of the subject, such as general health, other diseases, age, sex, genotype, body weight, and tolerance to drugs. The skilled artisan will be able to determine appropriate dosages depending on these and other factors.

A "subject" includes mammals, e.g., humans, companion animals (e.g., dogs, cats, birds, and the like), farm animals (e.g., cows, sheep, pigs, horses, and the like), and laboratory animals (e.g., rats, mice, guinea pigs, and the like). Typically, the subject is human.

The term "assay" or "assaying" relates to the creation of experimental conditions and the gathering of data regarding a particular result of the exposure to specific experimental conditions. For example, biomolecules or target molecules, e.g., enzymes or receptors, can be assayed based on their ability to act upon a detectable substrate. A compound can be assayed based on its ability to bind to a particular target molecule or molecules.

As used herein, the terms "ligand" and "modulator" may be used equivalently to refer to a compound that changes (i.e., increases or decreases) the activity of a target biomolecule, e.g., an enzyme or receptor. Generally, a ligand or modulator is a compound that possesses pharmacological and/or pharmacokinetic properties for a particular biological system or therapeutic use.

The term "binds" in connection with the interaction between a target and a potential binding compound indicates that the potential binding compound associates with the target to a statistically significant degree as compared to association with proteins generally (i.e., non-specific binding). Thus, the term "binding compound" refers to a compound that has a statistically significant association with a target molecule. In some embodiments, a binding compound interacts with a specified target with a dissociation constant ($K_D$) of about 1 mM or less, about 1 μM or less, e.g., about 500 nm, about 400 nm, about 300 nm, about 200 nm, or about 100 nm, about 50 nM or less, about 10 nM or less, or about 1 nM or less. In the context of compounds binding to a target, the terms "greater affinity" and "selective" indicates that the compound binds more tightly than a reference compound, or than the same compound in a reference condition, i.e., with a lower dissociation constant. In some embodiments, the greater affinity is at least about 2, 3, 4, 5, 8, 10, 30, 50, 100, 200, 400, 500, 1000, or 10,000-fold greater affinity.

Compounds of the Disclosure

The present disclosure relates to isotopically labeled (e.g., deuterated) derivatives of bile acids (e.g., obeticholic acid) including amino acid conjugates and glucuronides thereof.

In some of the embodiments, the present disclosure pertains to a compound of Formula I.

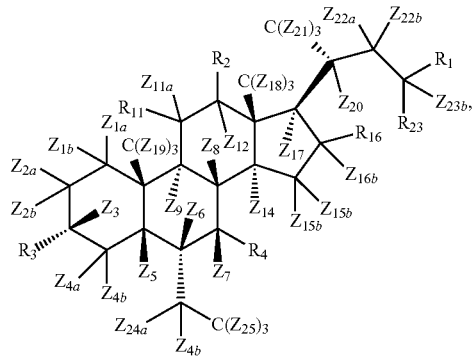

I or a pharmaceutically acceptable salt thereof, wherein
$R_1$ is OH, O-glucuronide, $OSO_3H$, $SO_3H$, $CO_2R_5$, $^{14}CO_2R_5$, $C(O)R_6$, or $^{14}C(O)R_6$;
$R_2$ is H, D, or OH;
$R_3$ is OH or O-glucuronide;
$R_4$ is OH or O-glucuronide;
$R_5$ is H or substituted or unsubstituted alkyl;
$R_6$ is $NH(CH_2)_2SO_3H$, $NHCH_2CO_2H$, or $N(CH_3)CH_2CO_2H$ or glucuronic acid moieties, wherein hydrogens can be replaced with deuterium;
$R_{11}$ is $Z_{11b}$, hydroxy, halogen, alkoxy, or oxo when $Z_{11a}$ is not present;
$R_{16}$ is $Z_{16a}$, hydroxy, halogen, alkoxy, or oxo when $Z_{16b}$ is not present;
$R_{23}$ is $Z_{23a}$ or alkyl; and
$Z_{1a}$, $Z_{1b}$, $Z_{2a}$, $Z_{2b}$, $Z_3$, $Z_{4a}$, $Z_{4b}$, $Z_5$, $Z_6$, $Z_7$, $Z_8$, $Z_9$, $Z_{11a}$, $Z_{11b}$, $Z_{12}$, $Z_{14}$, $Z_{15a}$, $Z_{15b}$, $Z_{16a}$, $Z_{16b}$, $Z_{17}$, $Z_{18}$, $Z_{19}$, $Z_{20}$, $Z_{21}$, $Z_{22a}$, $Z_{22b}$, $Z_{23a}$, $Z_{23b}$, $Z_{24a}$, $Z_{24b}$, or $Z_{25}$ is independently selected from H (hydrogen) or D (deuterium), and at least one of $Z_{1a}$, $Z_{1b}$, $Z_{2a}$, $Z_{2b}$, $Z_3$, $Z_{4a}$, $Z_{4b}$, $Z_5$, $Z_6$, $Z_7$, $Z_8$, $Z_9$, $Z_{11a}$, $Z_{11b}$, $Z_{12}$, $Z_{14}$, $Z_{15a}$, $Z_{15b}$, $Z_{16a}$, $Z_{16b}$, $Z_{17}$, $Z_{18}$, $Z_{19}$, $Z_{20}$, $Z_{21}$, $Z_{22a}$, $Z_{22b}$, $Z_{23a}$, $Z_{23b}$, $Z_{24a}$, $Z_{24b}$, or $Z_{25}$ is D; and
any carbon atom is $^{11}C$, $^{12}C$, $^{13}C$, or $^{14}C$, any nitrogen atom is $^{13}N$, $^{14}N$ or $^{15}N$, and any oxygen atom is $^{15}O$, $^{16}O$, $^{17}O$, or $^{18}O$.

In some of the embodiments, $R_2$ is hydrogen. In some of the embodiments, $R_2$ is hydroxy. In some of the embodiments, $R_2$ is alpha-hydroxy.

In some of the embodiments, $R_{11}$ is hydroxy or oxo.
In some of the embodiments, $R_{16}$ is hydroxy or oxo.
In some of the embodiments, $R_2$ is hydrogen and $R_{11}$ is hydroxy.
In some of the embodiments, $R_2$ is hydroxy and $R_{11}$ is hydroxy.
In some embodiments $R_{23}$ is methyl. In some embodiments $R_{23}$ is (S)-methyl. In some embodiments $R_{23}$ is (R)-methyl.
In some embodiment, $R_6$ is taurine ($—NH(CH_2)_2SO_3H$), glycine ($—NHCH_2CO_2H$), or sarcosine ($—N(CH_3)CH_2CO_2H$).

In certain embodiments, the present disclosure relates to compounds of Formula I having a chemical structure corresponding to Formulas II, III, IV, and V.

In certain embodiments, the present disclosure relates to a compound of Formula II

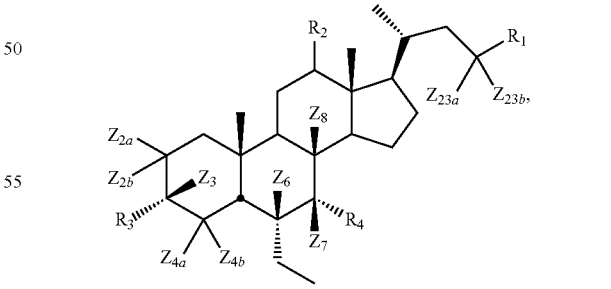

II wherein
$Z_{2a}$, $Z_{2b}$, $Z_3$, $Z_{4a}$, $Z_{4b}$, $Z_6$, $Z_7$, $Z_8$, $Z_{23a}$, or $Z_{23b}$ is independently selected from H or D and at least one of $Z_{2a}$, $Z_{2b}$, $Z_3$, $Z_{4a}$, $Z_{4b}$, $Z_6$, $Z_7$, $Z_8$, $Z_{23a}$, or $Z_{23b}$ is D and $R_1$, $R_2$, $R_3$, and $R_4$ are as described above.

In some of the embodiments, at least two of $Z_{2a}$, $Z_{2b}$, $Z_3$, $Z_{4a}$, $Z_{4b}$, $Z_6$, $Z_7$, $Z_8$, $Z_{23a}$, or $Z_{23b}$ are D. In some of the embodiments, at least three of $Z_{2a}$, $Z_{2b}$, $Z_3$, $Z_{4a}$, $Z_{4b}$, $Z_6$, $Z_7$, $Z_8$, $Z_{23a}$, or $Z_{23b}$ are D. In some of the embodiments, at least four of $Z_{2a}$, $Z_{2b}$, $Z_3$, $Z_{4a}$, $Z_{4b}$, $Z_6$, $Z_7$, $Z_8$, $Z_{23a}$, or $Z_{23b}$ are D. In some of the embodiments, at least five of $Z_{2a}$, $Z_{2b}$, $Z_3$, $Z_{4a}$, $Z_{4b}$, $Z_6$, $Z_7$, $Z_8$, $Z_{23a}$, or $Z_{23b}$ are D. In some of the embodiments, at least six of $Z_{2a}$, $Z_{2b}$, $Z_3$, $Z_{4a}$, $Z_{4a}$, $Z_6$, $Z_7$, $Z_8$, $Z_{23a}$, or $Z_{23b}$ are D. In some of the embodiments, at least seven of $Z_{2a}$, $Z_{2b}$, $Z_3$, $Z_{4a}$, $Z_{4b}$, $Z_6$, $Z_7$, $Z_8$, $Z_{23a}$, or $Z_{23b}$ are D. In some of the embodiments, at least eight of $Z_{2a}$, $Z_{2b}$, $Z_3$, $Z_{4a}$, $Z_{4b}$, $Z_6$, $Z_7$, $Z_8$, $Z_{23a}$, or $Z_{23b}$ are D. In some of the embodiments, at least nine of $Z_{2a}$, $Z_{2b}$, $Z_3$, $Z_{4a}$, $Z_{4b}$, $Z_6$, $Z_7$, $Z_8$, $Z_{23a}$, or $Z_{23b}$ are D. In some embodiments, $Z_{2a}$, $Z_{2b}$, $Z_3$, $Z_{4a}$, $Z_{4b}$, $Z_6$, $Z_7$, $Z_8$, $Z_{23a}$, and $Z_{23b}$ are D.

In some of the embodiments, $R_2$ is hydrogen. In some of the embodiments, $R_2$ is hydroxy. In some of the embodiments, $R_2$ is alpha-hydroxy.

In some embodiments, any carbon atom of the compound of Formula II, or a pharmaceutically acceptable salt thereof, is $^{11}C$, $^{12}C$, $^{13}C$, or $^{14}C$, any nitrogen atom is $^{13}N$, $^{14}N$ or $^{15}N$, and any oxygen atom is $^{15}O$, $^{16}O$, $^{17}O$, or $^{18}O$.

In certain embodiments, the present disclosure relates to a compound of Formula III

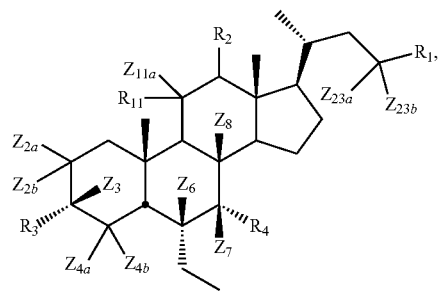

III wherein $Z_{2a}$, $Z_{2b}$, $Z_3$, $Z_{4a}$, $Z_{4b}$, $Z_6$, $Z_7$, $Z_8$, $Z_{11a}$, $Z_{23a}$, or $Z_{23b}$ is independently selected from H or D and at least one of $Z_{2a}$, $Z_{2b}$, $Z_3$, $Z_{4a}$, $Z_{4b}$, $Z_6$, $Z_7$, $Z_8$, $Z_{23a}$, or $Z_{23b}$ is D and $R_1$, $R_2$, $R_3$, $R_4$, and $R_{11}$ are as described above.

In some of the embodiments, at least two of $Z_{2a}$, $Z_{2b}$, $Z_3$, $Z_{4a}$, $Z_{4b}$, $Z_6$, $Z_7$, $Z_8$, $Z_{11a}$, $Z_{23a}$, or $Z_{23b}$ are D. In some of the embodiments, at least three of $Z_{2a}$, $Z_{2b}$, $Z_3$, $Z_{4a}$, $Z_{4b}$, $Z_6$, $Z_7$, $Z_8$, $Z_{11a}$, $Z_{23a}$, or $Z_{23b}$ are D. In some of the embodiments, at least four of $Z_{2a}$, $Z_{2b}$, $Z_3$, $Z_{4a}$, $Z_{4b}$, $Z_6$, $Z_7$, $Z_8$, $Z_{11a}$, $Z_{23a}$, or $Z_{23b}$ are D. In some of the embodiments, at least five of $Z_{2a}$, $Z_{2b}$, $Z_3$, $Z_{4a}$, $Z_{4b}$, $Z_6$, $Z_7$, $Z_8$, $Z_{11a}$, $Z_{23a}$, or $Z_{23b}$ are D. In some of the embodiments, at least six of $Z_{2a}$, $Z_{2b}$, $Z_3$, $Z_{4a}$, $Z_{4b}$, $Z_6$, $Z_7$, $Z_8$, $Z_{11a}$, $Z_{23a}$, or $Z_{23b}$ are D. In some of the embodiments, at least seven of $Z_{2a}$, $Z_{2b}$, $Z_3$, $Z_{4a}$, $Z_{4b}$, $Z_6$, $Z_7$, $Z_8$, $Z_{11a}$, $Z_{23a}$, or $Z_{23b}$ are D. In some of the embodiments, at least eight of $Z_{2a}$, $Z_{2b}$, $Z_3$, $Z_{4a}$, $Z_{4b}$, $Z_6$, $Z_7$, $Z_8$, $Z_{11a}$, $Z_{23a}$, or $Z_{23b}$ are D. In some of the embodiments, at least nine of $Z_{2a}$, $Z_{2b}$, $Z_3$, $Z_{4a}$, $Z_{4b}$, $Z_6$, $Z_7$, $Z_8$, $Z_{11a}$, $Z_{23a}$, or $Z_{23b}$ are D. In some embodiments, at least ten $Z_{2a}$, $Z_{2b}$, $Z_3$, $Z_{4a}$, $Z_{4b}$, $Z_6$, $Z_7$, $Z_8$, $Z_{11a}$, $Z_{23a}$, and $Z_{23b}$ are D. In some embodiments, $Z_{2a}$, $Z_{2b}$, $Z_3$, $Z_{4a}$, $Z_{4b}$, $Z_6$, $Z_7$, $Z_8$, $Z_{11a}$, $Z_{23a}$, and $Z_{23b}$ are D.

In some of the embodiments, $R_2$ is hydrogen. In some of the embodiments, $R_2$ is hydroxy. In some of the embodiments, $R_2$ is alpha-hydroxy.

In some of the embodiments, $R_{11}$ is hydroxy or oxo.

In some of the embodiments, $R_2$ is hydrogen and $R_{11}$ is hydroxy.

In some of the embodiments, $R_2$ is hydroxy and $R_{11}$ is hydroxy.

In certain embodiments, the present disclosure relates to a compound of Formula IV

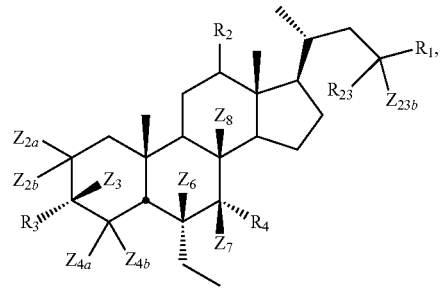

IV wherein $Z_{2a}$, $Z_{2b}$, $Z_3$, $Z_{4a}$, $Z_{4b}$, $Z_6$, $Z_7$, $Z_8$, or $Z_{23b}$ is independently selected from H or D and at least one of $Z_{2a}$, $Z_{2b}$, $Z_3$, $Z_{4a}$, $Z_{4b}$, $Z_6$, $Z_7$, $Z_8$, or $Z_{23b}$ is D, $R_{23}$ is alkyl, and $R_2$, $R_3$, $R_4$, and are as described above.

In some of the embodiments, at least two of $Z_{2a}$, $Z_{2b}$, $Z_3$, $Z_{4a}$, $Z_{4b}$, $Z_6$, $Z_7$, $Z_8$, or $Z_{23b}$ are D. In some of the embodiments, at least three of $Z_{2a}$, $Z_{2b}$, $Z_3$, $Z_{4a}$, $Z_{4b}$, $Z_6$, $Z_7$, $Z_8$, or $Z_{23b}$ are D. In some of the embodiments, at least four of $Z_{2a}$, $Z_{2b}$, $Z_3$, $Z_{4a}$, $Z_{4b}$, $Z_6$, $Z_7$, $Z_8$, or $Z_{23b}$ are D. In some of the embodiments, at least five of $Z_{2a}$, $Z_{2b}$, $Z_3$, $Z_{4a}$, $Z_{4b}$, $Z_6$, $Z_7$, $Z_8$, or $Z_{23b}$ are D. In some of the embodiments, at least six of $Z_{2a}$, $Z_{2b}$, $Z_3$, $Z_{4a}$, $Z_{4b}$, $Z_6$, $Z_7$, $Z_8$, or $Z_{23b}$ are D. In some of the embodiments, at least seven of $Z_{2a}$, $Z_{2b}$, $Z_3$, $Z_{4a}$, $Z_{4b}$, $Z_6$, $Z_7$, $Z_8$, or $Z_{23b}$ are D. In some of the embodiments, at least eight of $Z_{2a}$, $Z_{2b}$, $Z_3$, $Z_{4a}$, $Z_{4b}$, $Z_6$, $Z_7$, $Z_8$, or $Z_{23b}$ are D. In some of the embodiments, $Z_{2a}$, $Z_{2b}$, $Z_3$, $Z_{4a}$, $Z_{4b}$, $Z_6$, $Z_7$, $Z_8$, or $Z_{23b}$ are D.

In some of the embodiments, $R_2$ is hydrogen. In some of the embodiments, $R_2$ is hydroxy. In some of the embodiments, $R_2$ is alpha-hydroxy.

In some embodiments $R_{23}$ is methyl. In some embodiments $R_{23}$ is (S)-methyl. In some embodiments $R_{23}$ is (R)-methyl.

In some embodiments, any carbon atom of the compound of Formula IV, or a pharmaceutically acceptable salt thereof, is $^{11}C$, $^{12}C$, $^{13}C$, or $^{14}C$, any nitrogen atom is $^{13}N$, $^{14}N$ or $^{15}N$, and any oxygen atom is $^{15}O$, $^{16}O$, $^{17}O$, or $^{18}O$.

In certain embodiments, the present disclosure relates to a compound of Formula V

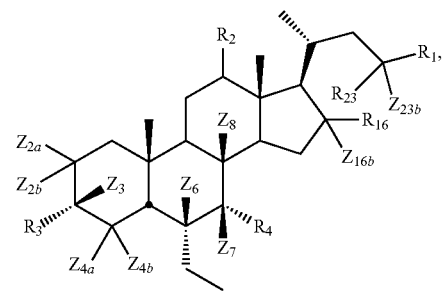

V wherein $Z_{2a}$, $Z_{2b}$, $Z_3$, $Z_{4a}$, $Z_{4b}$, $Z_6$, $Z_7$, $Z_8$, $Z_{16b}$ or $Z_{23b}$ is independently selected from H or D and at least one of $Z_{2a}$, $Z_{2b}$, $Z_3$, $Z_{4a}$, $Z_{4b}$, $Z_6$, $Z_7$, $Z_8$, $Z_{16b}$, $Z_{23a}$ or $Z_{23b}$ is D, $R_{16}$ is hydroxy, and $R_2$, $R_3$, $R_4$, and $R_{23}$ are as described above.

In some of the embodiments, at least two of $Z_{2a}$, $Z_{2b}$, $Z_3$, $Z_{4a}$, $Z_{4b}$, $Z_6$, $Z_7$, $Z_8$, $Z_{16b}$, $Z_{23a}$ or $Z_{23b}$ are D. In some of the embodiments, at least three of $Z_{2a}$, $Z_{2b}$, $Z_3$, $Z_{4a}$, $Z_{4b}$, $Z_6$, $Z_7$, $Z_8$, $Z_{16b}$, $Z_{23a}$ or $Z_{23b}$ are D. In some of the embodiments, at least four of $Z_{2a}$, $Z_{2b}$, $Z_3$, $Z_{4a}$, $Z_{4b}$, $Z_6$, $Z_7$, $Z_8$, $Z_{16b}$, $Z_{23a}$ or $Z_{23b}$ are D. In some of the embodiments, at least five of $Z_{2a}$, $Z_{2b}$, $Z_3$, $Z_{4a}$, $Z_{4b}$, $Z_6$, $Z_7$, $Z_8$, $Z_{16b}$, $Z_{23a}$ or $Z_{23b}$ are D. In some of the embodiments, at least six of $Z_{2a}$, $Z_{2b}$, $Z_3$, $Z_{4a}$, $Z_{4b}$, $Z_6$, $Z_7$, $Z_8$, $Z_{16b}$, $Z_{23a}$ or $Z_{23b}$ are D. In some of the embodiments, at least seven of $Z_{2a}$, $Z_{2b}$, $Z_3$, $Z_{4a}$, $Z_{4b}$, $Z_6$, $Z_7$, $Z_8$, $Z_{16b}$, $Z_{23a}$ or $Z_{23b}$ are D. In some of the embodiments, at least eight of $Z_{2a}$, $Z_{2b}$, $Z_3$, $Z_{4a}$, $Z_{4b}$, $Z_6$, $Z_7$, $Z_8$, $Z_{16b}$, $Z_{23a}$ or $Z_{23b}$ are D. In some of the embodiments, at least nine of $Z_{2a}$, $Z_{2b}$, $Z_3$, $Z_{4a}$, $Z_{4b}$, $Z_6$, $Z_7$, $Z_8$, $Z_{16b}$, $Z_{23a}$ or $Z_{23b}$ are D. In some of the embodiments, at least ten of $Z_{2a}$, $Z_{2b}$, $Z_3$, $Z_{4a}$, $Z_{4b}$, $Z_6$, $Z_7$, $Z_8$, $Z_{16b}$, $Z_{23a}$ or $Z_{23b}$ are D. In some of the embodiments, $Z_{2a}$, $Z_{2b}$, $Z_3$, $Z_{4a}$, $Z_{4b}$, $Z_6$, $Z_7$, $Z_8$, $Z_{16b}$, $Z_{23a}$ or $Z_{23b}$ are D.

In some of the embodiments, $R_2$ is hydrogen. In some of the embodiments, $R_2$ is hydroxy. In some of the embodiments, $R_2$ is alpha-hydroxy.

In some embodiments $R_{16}$ is alpha-hydroxy. In some embodiments $R_{16}$ is beta-hydroxy.

In some embodiments $R_{23}$ is methyl. In some embodiments $R_{23}$ is (S)-methyl. In some embodiments $R_{23}$ is (R)-methyl.

In some embodiments, any carbon atom of the compound of Formula V, or a pharmaceutically acceptable salt thereof, is $^{11}C$, $^{12}C$, $^{13}C$, or $^{14}C$, any nitrogen atom is $^{13}N$, $^{14}N$ or $^{15}N$, and any oxygen atom is $^{15}O$, $^{16}O$, $^{17}O$, or $^{18}O$.

In some embodiments, the present disclosure relates to compounds of Formula VI

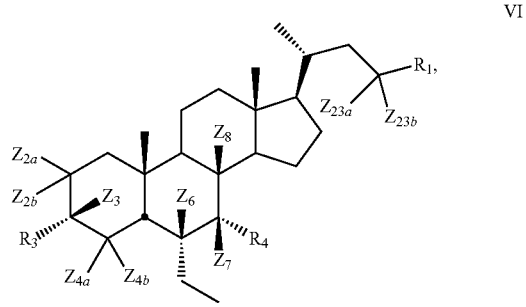

VI wherein $Z_{2a}$, $Z_{2b}$, $Z_3$, $Z_{4a}$, $Z_{4b}$, $Z_6$, $Z_7$, $Z_8$, $Z_{23a}$, or $Z_{23b}$ is independently selected from H or D and at least one of $Z_{2a}$, $Z_{2b}$, $Z_3$, $Z_{4a}$, $Z_{4b}$, $Z_6$, $Z_7$, $Z_8$, $Z_{23a}$, or $Z_{23b}$ is D and $R_1$, $R_3$, and $R_4$ are as described above.

In some embodiments, the present disclosure relates to compounds of Formula VII

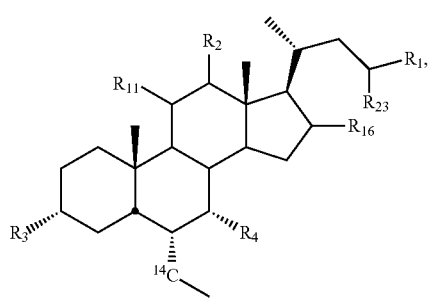

VII wherein $R_1$, $R_2$, $R_3$, $R_4$, $R_{11}$, $R_{16}$, and $R_{23}$ are as described above.

In some embodiments, the present disclosure relates to compounds of Formula VIII

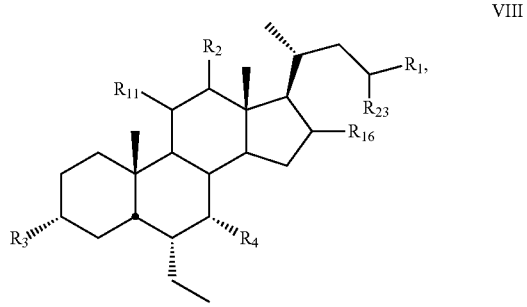

VIII wherein $R_1$ is $^{14}CO_2R_5$ or $^{14}C(O)R_6$ and $R_2$, $R_3$, $R_4$, $R_{11}$, $R_{16}$, and $R_{23}$ are as described above.

Synthesis of Compound of the Disclosure

Some embodiments of the present disclosure relate to a process for preparing the compound of Formula I.

Compounds of Formula I can be prepared by methods known in the art, e.g., those described in U.S. Pat. Nos. 7,932,244; 8,114,862; 9,238,673; and 9,611,289 and publications WO 2014/066819 and WO 2017/062763, the entire contents of each of which are incorporated herein by reference.

Standard synthetic methods and procedures for the preparation of organic molecules and functional group transformations and manipulations, including the use of protective groups, can be obtained from the relevant scientific literature or from standard reference textbooks in the field. Although not limited to any one or several sources, recognized reference textbooks of organic synthesis include: Smith, M. B.; March, J. March's Advanced Organic Chemistry: Reactions, Mechanisms, and Structure, 5$^{th}$ ed.; John Wiley & Sons: New York, 2001; and Greene, T. W.; Wuts, P G. M. Protective Groups in Organic Synthesis, 3$^{rd}$, John Wiley & Sons: New York, 1999.

In some embodiments, the present disclosure relates to a process for preparing the compound of Formula II. In some embodiments, the present disclosure relates to a process for preparing the compound of Formula III. In some embodiments, the present disclosure relates to a process for preparing the compound of Formula IV. In some embodiments, the present disclosure relates to a process for preparing the compound of Formula V. In some embodiments, the present disclosure relates to a process for preparing the compound of Formula VI. In some embodiments, the present disclosure relates to a process for preparing the compound of Formula VII. In some embodiments, the present disclosure relates to a process for preparing the compound of Formula VIII.

In one aspect, this application pertains to methods for preparing deuterated compounds of Formula (I). Depending on the desired sites of deuteration, in some cases deuterium from $D_2O$ can be exchanged directly into finished drug compounds or into reagents that are useful for synthesizing drug molecules (H. Esaki, et al., Tetrahedron, 2006, 62, 10954; H. Esaki, et al., Chem. Eur. J., 2007, 13, 4052). In protic solution exchangeable protons (e.g., such as those in hydroxyl or amine group) exchange protons with the solvent. If $D_2O$ is solvent, deuterons will be incorporated at these positions. The exchange reaction can be followed using a variety of methods (e.g. NMR spectroscopy). Since this exchange is an equilibrium reaction, the molar amount of deuterium should be high compared to the exchangeable protons of the substrate. For instance, deuterium is added to a compound in $H_2O$ by diluting the $H_2O$ solution with $D_2O$ (e.g. tenfold). Usually exchange is performed at physiological pH (7.0-8.0). The H/D exchange reaction can also be catalysed, by acid, base or metal catalysts (e.g., platinum). The deuteration pattern of a molecule that has undergone H/D exchange can be maintained in aprotic environments. Deuterium gas is also a useful starting material for incorporating deuterium into molecules. Catalytic deuteration of olefinic and acetylenic bonds is a rapid route for incorporation of deuterium (H. J. Leis, et al., Curr. Org. Chem., 1998, 2, 131). Metal catalysts (i.e., Pd, Pt, and Rh) in the presence of deuterium gas can be used to directly exchange deuterium for hydrogen in functional groups containing hydrocarbons (U.S. Pat. No. 3,966,781). A wide variety of deuterated reagents and synthetic building blocks are commercially available.

Some embodiments of the present disclosure pertain to methods of preparing deuterated compounds of Formula I, II, III, IV, V, VI, VII, and VIII based on the methods known in the art including but not limited to the procedures shown in Schemes 1-11. The methods shown in Schemes 1-11 are based on obeticholic acid (OCA) as starting material, but can be applied to any bile acid analogs of the present disclosure to prepare compounds of Formulas I-VIII.

In some embodiments, $d_{10}$-OCA analogs can be prepared according to Scheme 1. As shown, $d_{10}$-OCA analogs can be prepared by first treating 3,7-diketo-OCA methyl ester with a base, e.g., sodium methoxide in the presence of deuterated methanol and concommitent treatment with sodium deuteroxide in $D_2O$, at ambient or elevated temperature, to generate 3,7-diketo-($d_8$)-OCA. Further treatment with deuterated reducing agent such as, for example, $NaBD_4$ generates $d_{10}$-OCA. The $d_{10}$-OCA obtained can be coupled with various moieties, for example, taurine, glycine, other amino acids, glucuronic acid or their deuterated counterparts, as described herein, to generate $d_{10}$-OCA derivatives.

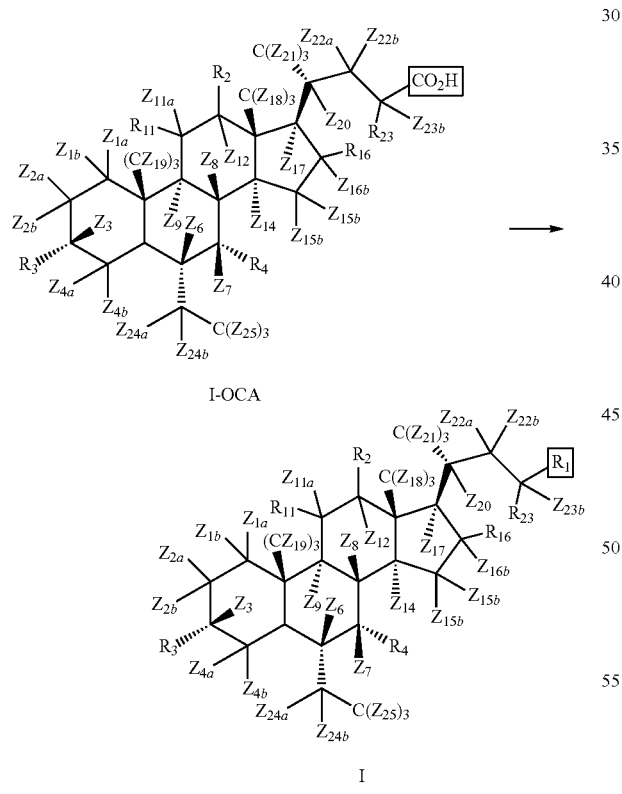

Scheme 1. $d_{10}$-OCA Analogs

21

-continued

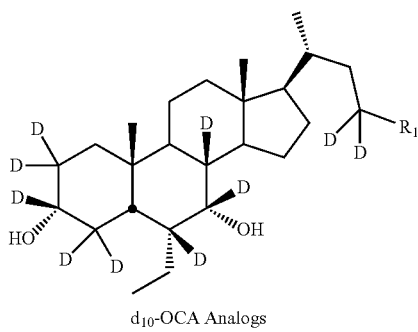

d₁₀-OCA Analogs

22

-continued

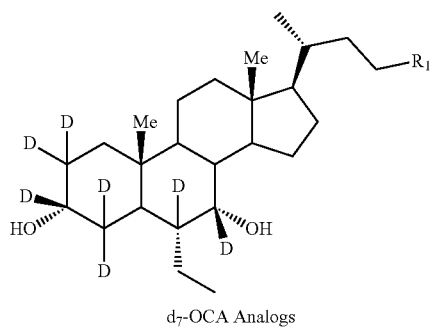

d₇-OCA Analogs

In some embodiments, d₇-OCA analogs are prepared according to Scheme 2. As shown, d₇-OCA analogs can be prepared by treating 3,7-diketo-OCA in D₂O with NaOD at ambient temperature. The reaction is monitored by ¹H-NMR until the deuterium exchange is complete and d₅-3,7-diketo-OCA is obtained. Next, the d₅-3,7-diketo-OCA intermediate is treated with NaBD₄ to generate d₇-OCA. The d₇-OCA obtained can be coupled with various moieties, for example, taurine, glycine, other amino acids, glucuronic acid or their deuterated counterparts, as described herein, to generate d₇-OCA derivatives.

In some embodiments, d₅-OCA (C3) analogs can be prepared according to Scheme 3. As shown, d₅-OCA (C3) analogs can be prepared by oxidizing OCA to 3-keto-OCA using an oxidizing agent, e.g., catalytic TPAP in the presence of N-methylmorpholine oxide. In some embodiments, reaction using an oxidizing agent, e.g., catalytic TPAP in the presence of N-methylmorpholine oxide, provided 3-keto OCA selectively. Reaction of 3-keto-OCA with NaOD in D₂O, followed by treatment of NaBD₄ generates d₅-OCA (C3). The d₅-OCA obtained can be coupled with various moieties, for example, taurine, glycine, other amino acids, glucuronic acid or their deuterated counterparts, as described herein, to generate d₅-OCA (C3) derivatives.

Scheme 2. d₇-OCA Analogs

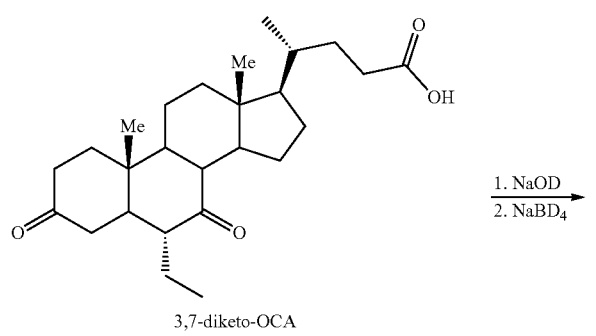

Scheme 3. d₅-OCA Analogs (C3)

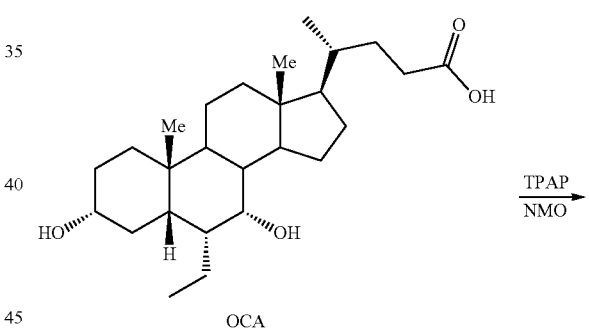

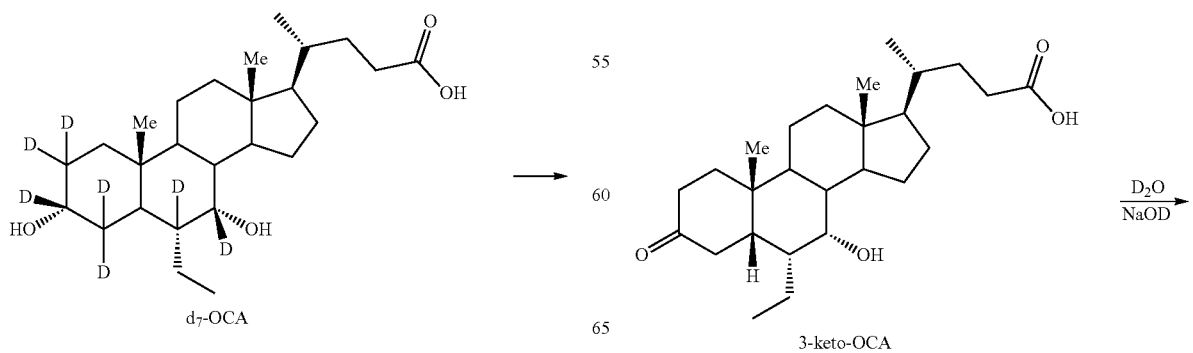

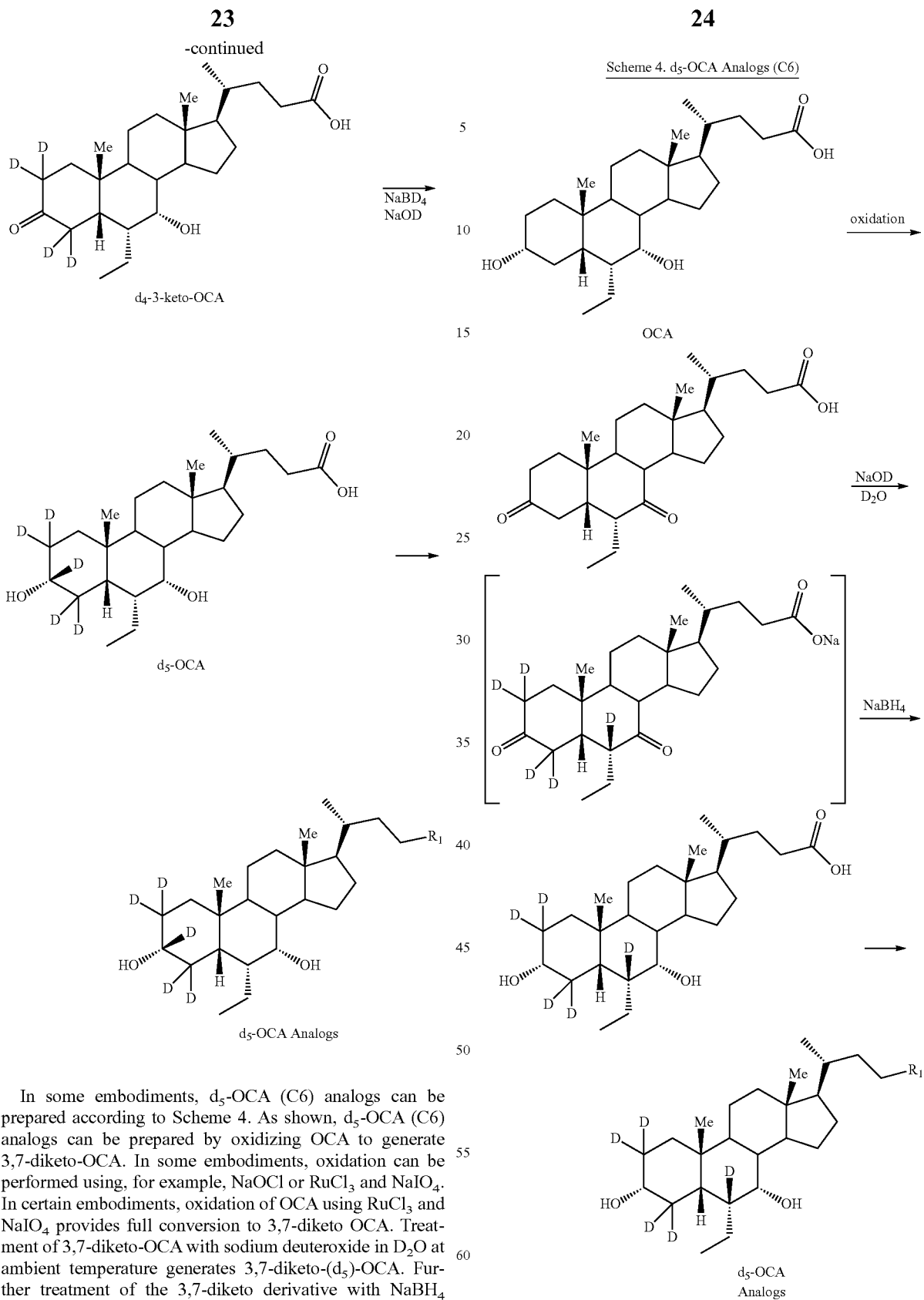

Scheme 4. d$_5$-OCA Analogs (C6)

In some embodiments, d$_5$-OCA (C6) analogs can be prepared according to Scheme 4. As shown, d$_5$-OCA (C6) analogs can be prepared by oxidizing OCA to generate 3,7-diketo-OCA. In some embodiments, oxidation can be performed using, for example, NaOCl or RuCl$_3$ and NaIO$_4$. In certain embodiments, oxidation of OCA using RuCl$_3$ and NaIO$_4$ provides full conversion to 3,7-diketo OCA. Treatment of 3,7-diketo-OCA with sodium deuteroxide in D$_2$O at ambient temperature generates 3,7-diketo-(d$_5$)-OCA. Further treatment of the 3,7-diketo derivative with NaBH$_4$ generates d$_5$-OCA. The d$_5$-OCA obtained can be coupled with various moieties, for example, taurine, glycine, other amino acids, glucuronic acid or their deuterated counterparts, as described herein, to generate d$_5$-OCA (C6) derivatives.

In some embodiments, d$_4$-OCA analogs (C3(d)-C7(d)-C23(d$_2$)-OCA) can be prepared according to Scheme 5. As shown, d$_4$-OCA analogs (C3(d)-C7(d)-C23(d$_2$)-OCA) can be prepared by treating OCA with HCl in the presence of methanol to generate the OCA methyl ester (OCA-OMe). Deuterium is introduced into the C23 position by treatment of OCA-OMe with NaOMe in MeOD to generate $d_2$-OCA-OMe. Ester hydrolysis with NaOD in $D_2O$ generates $d_2$-OCA, which is subjected to oxidation with catalytic $RuCl_3$ in the presence of $NaIO_4$ to generate $d_2$-3,7-diketo-OCA. The diketone is subjected to reduction using $NaBD_4$ in the presence of NaOD in $D_2O$ to generate $d_4$-OCA. The $d_4$-OCA obtained can be coupled with various moieties, for example, taurine, glycine, other amino acids, glucuronic acid or their deuterated counterparts, to generate $d_4$-OCA derivatives.

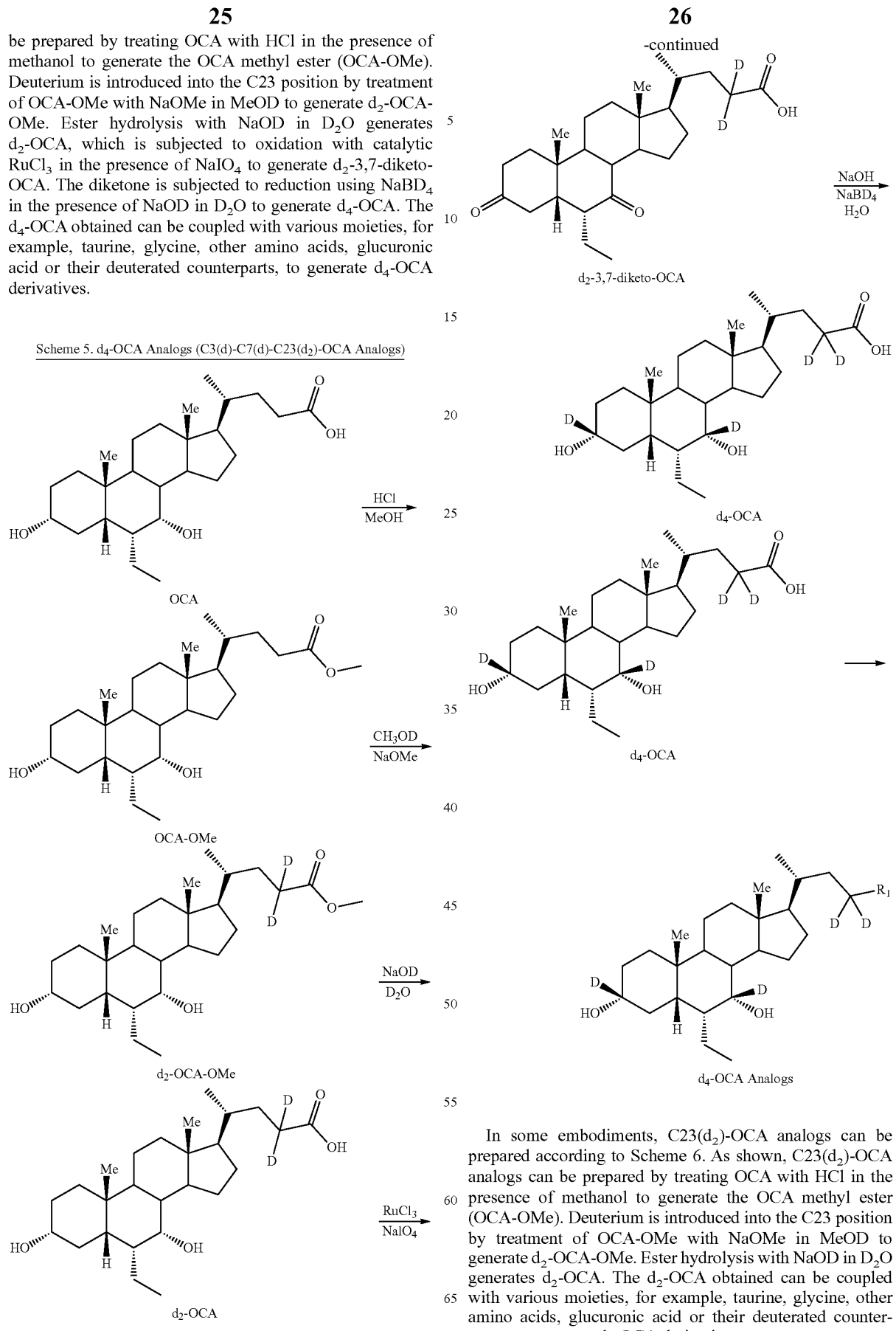

In some embodiments, C23($d_2$)-OCA analogs can be prepared according to Scheme 6. As shown, C23($d_2$)-OCA analogs can be prepared by treating OCA with HCl in the presence of methanol to generate the OCA methyl ester (OCA-OMe). Deuterium is introduced into the C23 position by treatment of OCA-OMe with NaOMe in MeOD to generate $d_2$-OCA-OMe. Ester hydrolysis with NaOD in $D_2O$ generates $d_2$-OCA. The $d_2$-OCA obtained can be coupled with various moieties, for example, taurine, glycine, other amino acids, glucuronic acid or their deuterated counterparts, to generate $d_2$-OCA derivatives.

Scheme 6. C23(d$_2$)-OCA Analogs

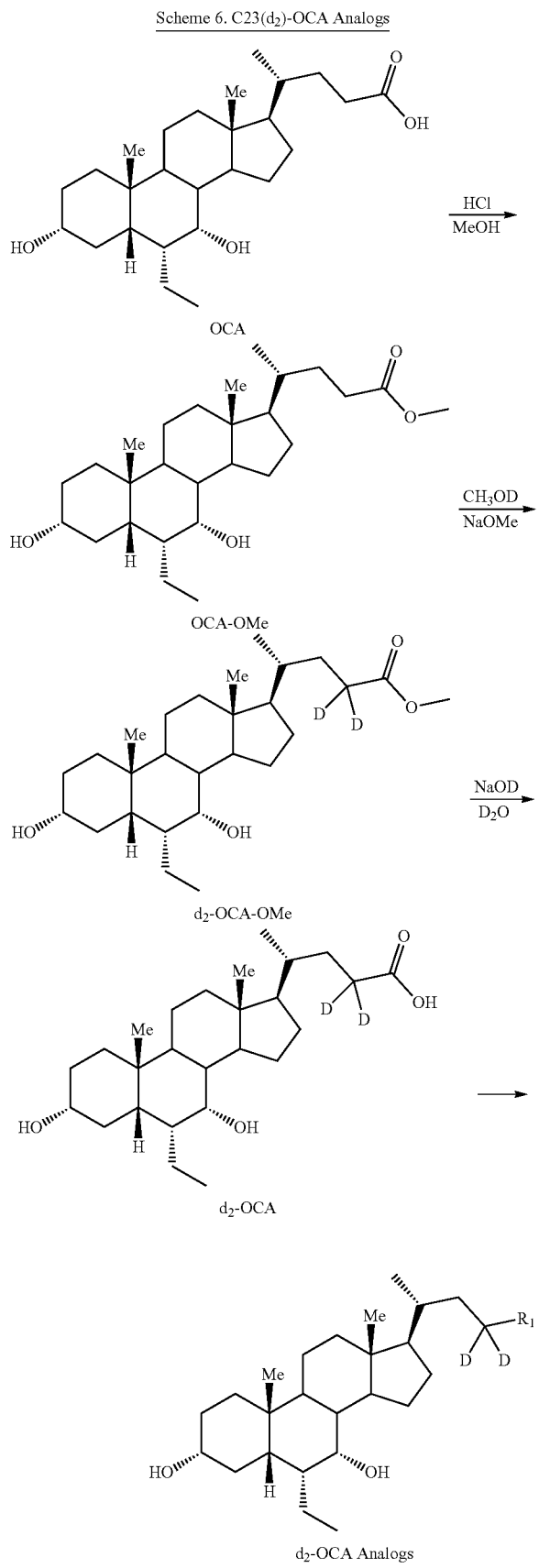

In some embodiments, the present disclosure relates to OCA conjugates, where hydrogens of the amino acid residue are fully or partially substituted with deuterium. In one of the embodiment the conjugate is fully deuterated. Any bile acid intermediate prepared by the methods described herein, including but not limited to procedures shown in Schemes 1-6, can be converted into the corresponding conjugate by using a suitable coupling reagent. Suitable coupling reagents include, but are not limited to carbodiimides, for example, dicyclohexylcarbodiimide (DCC), diisopropylcarbodiimide (DIC), N-(3-dimethylaminopropyl)-N'-ethylcarbodiimide-.HCl (EDAC.HCl, EDC.HCl, WSC.HCl); the phosphonium- and the aminium-(imonium-) type reagents which include, for example, benzotriazole-1-yl-oxy-tris-(dimethylamino)-phosphonium hexafluorophosphate (BOP), Benzotriazol-1-yloxy-tripyrrolidinophosphonium hexafluorophosphate (PyBOP®), Bromo-tripyrrolidino-phosphonium hexafluorophosphate (PyBrOP®), 7-aza-benzotriazol-1-yloxy-tripyrrolidinophosphonium hexafluorophosphate (PyAOP), ethyl cyano(hydroxyimino)acetate-O$_2$)-tri-(1-pyrrolidinyl)-phosphonium hexafluorophosphate (PyOxim), 3-(diethoxy-phosphoryloxy)-1,2,3-benzo[d]triazin-4(3H)-one (DEPBT), N-[(7-aza-1H-benzotriazol-1-yl)(dimethylamino)-methylene]-N-methylmethanaminium hexafluorophosphate N-oxide (HATU), N-[(5-chloro-1H-benzotriazol-1-yl)-dimethylamino-morpholino]-uronium hexafluorophosphate N-oxide (HDMC), N-[(7-aza-1H-benzotriazol-1-yl)(dimethylamino)-methylene]-N-methylmethanaminium tetrafluoroborate N-oxide (TATU), 2-(6-chloro-1H-benzotriazol-1-yl)-N,N,N',N'-tetramethylaminium hexafluorophosphate (HCTU), N-[(5-chloro-1H-benzotriazol-1-yl)-dimethylamino-morpholino]-uronium hexafluorophosphate N-oxide (HDMC), 2-(1H-benzotriazol-1-yl)-N,N,N',N'-tetramethylaminium tetrafluoroborate/hexafluorophosphate (TBTU (BF$_4^-$)/HBTU (PF$_6^-$)), 1-[1-(cyano-2-ethoxy-2-oxoethylideneaminooxy)-dimethylamino-morpholino]-uronium hexafluorophosphate (COMU), tetramethylfluoroformamidinium hexafluorophosphate (TFFH), and 2-(1-oxy-pyridin-2-yl)-1,1,3,3-tetramethylisothiouronium tetrafluoroborate (TOTT); and other coupling reagents, for example, N-ethoxycarbonyl-2-ethoxy-1,2-dihydroquinoline (EEDQ); 2-propanephosphonic acid anhydride (T3P), 4-(4,6-dimethoxy-1,3,5-triazin-2-yl)-4-methylmorpholinium salts (DMTMM) and related compounds, bis-trichloromethylcarbonate or "Triphosgene" (BTC), and 1,1'-Carbonyldiimidazole (CDI).

Some coupling reactions (e.g., amide bond formations) require the presence of an additive (e.g., to enhance the reactivity and also to reduce formation of epimers as well as N-acylureas), such as, for example, 1-hydroxybenzotriazole (HOBt), HOBt-6-sulfonamidomethyl resin.HCl (200-400 mesh), N-hydroxysuccinimide (HOSu), 1-hydroxy-7-aza-1H-benzotriazole (HOAt), ethyl 2-cyano-2-(hydroximino)acetate (Oxyma Pure®), and 4-(N,N-dimethylamino)-pyridine (DMAP).

Some coupling reactions (e.g., amide bond formations) require the presence of a base, for example, triethylamine, diisopropylethylamine (DIPEA), N-methylmorpholine (NMM), sym-collidine, 2,6-lutidine, Cs$_2$CO$_3$, NaHCO$_3$, etc.

In some of the embodiments, the present disclosure pertains to a method of making amino acid conjugates of Formula I.

Scheme B

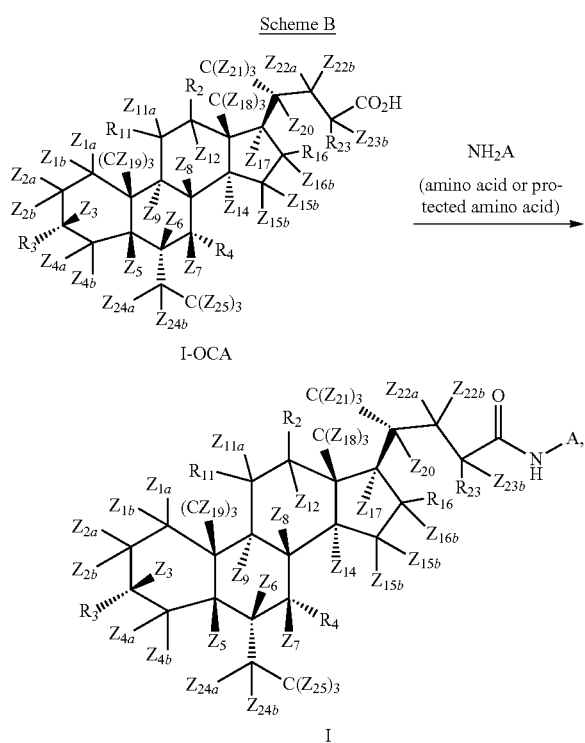

wherein A is an amino acid residue (protected or unprotected) or an amino acid residue where at least one hydrogen is replaced with deuterium or tritium (the carboxylic group of amino residue can be protected or unprotected).

In some of the embodiments, glycine conjugate, e.g., $d_5$-OCA-O($d_2$)Gly, can be prepared as shown in Scheme 7.

Scheme 7. $d_5$-OCA-O($d_2$)Gly

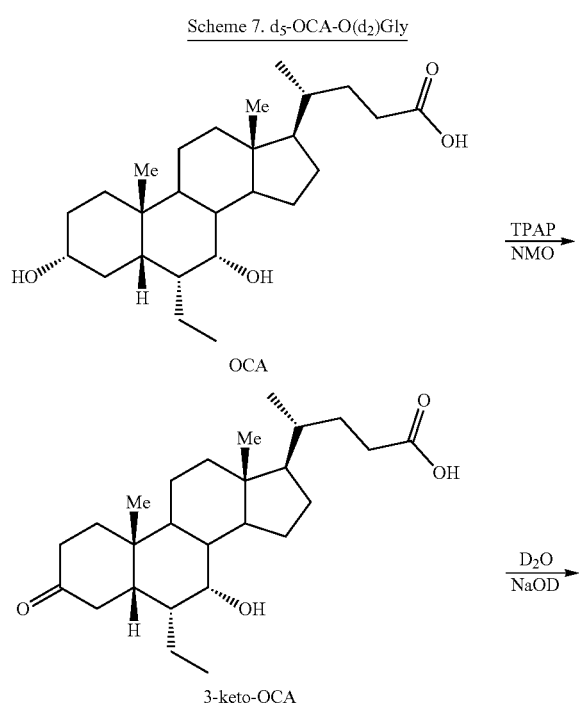

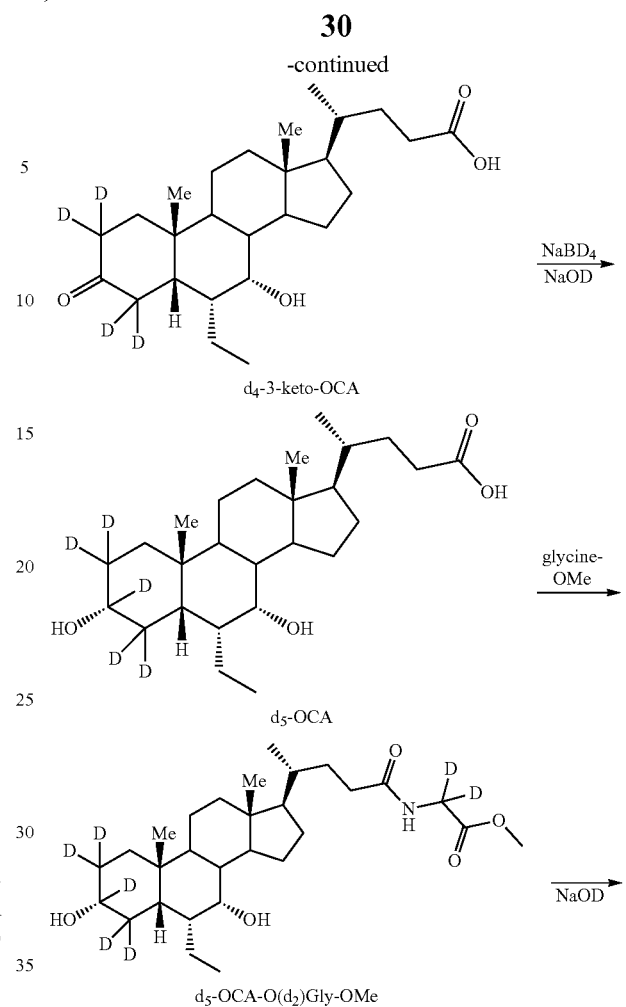

In some embodiments, $d_5$-OCA-O($d_2$)Gly analogs can be prepared by oxidizing OCA to 3-keto-OCA using, for example, catalytic TPAP in the presence of N-methylmorpholine oxide. Treating 3-keto-OCA with NaOD in $D_2O$ generates $d_4$-3-keto-OCA, which is treated with a reducing agent, e.g., $NaBD_4$ to generate $d_5$-OCA (as also shown in Schemes 3 and 4). Coupling of $d_5$-OCA with $d_2$-glycine methyl ester is achieved using a coupling reagent, e.g., 4-(4,6-dimethoxy-1,3,5-triazin-2-yl)-4-methylmorpholinium (DMT-MM), to afford $d_5$-OCA-O($d_2$)Gly-OMe. Ester hydrolysis using NaOD in $D_2O$ affords $d_5$-OCA-O($d_2$)Gly.

In some of the embodiments tauro conjugate, e.g., $d_5$-OCA-O($d_4$)Tau, can be prepared as shown in Scheme 8.

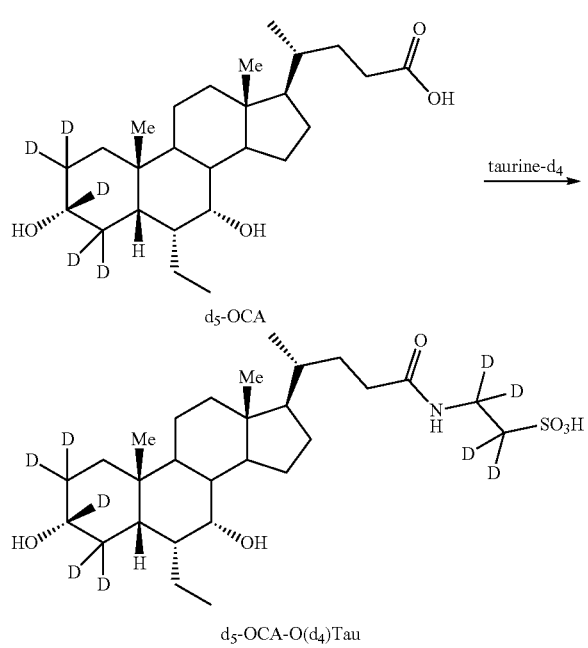

d₅-OCA

↓ taurine-d₄ d₅-OCA-O(d₄)Tau

In some embodiments, d₅-OCA-O(d₄)Tau analogs can be prepared by treating d₅-OCA in the presence of d₄-taurine and a coupling reagent (e.g., N-ethoxycarbonyl-2-ethoxy-1,2-dihydroquinoline (EEDQ), 1-[bis(dimethylamino)methylene]-1H-1,2,3-triazolo[4,5-b]pyridinium 3-oxide hexafluorophosphate (HATU) and 2,6-dichlorobenzoyl chloride, or other peptide coupling agent) and a base (e.g., triethylamine, DIPEA, 2,6-lutidine, $Cs_2CO_3$, etc.).

In some embodiments, as shown, for example, in Schemes 1-6, deuterium exchange and the reduction (using, e.g., $NaBD_4$) are carried out in one pot. In some embodiment, deuterium exchange and the reduction are carried out as two sequential steps.

Some embodiments of the present disclosure relate to compounds of Formulas I, II, III, IV, V, and VI having at least one carbon-12 ($^{12}C$) replaced with radioactive carbon-14 ($^{14}C$) or carbon-13 ($^{13}C$). In certain embodiments, compounds of the present disclosure (Formulas I-VI) are labeled with at least one $^{14}C$ (e.g., compound VII or VIII). Compounds labeled with $^{14}C$ can be prepared by various methods known in the art.

The general approach to quantify a metabolite is to synthesize a carbon-14-labeled version of the drug. By replacing a carbon-12 atom with radioactive carbon-14, researchers have a chemically identical analogue that enables the pathway of the drug to be traced in a biological system. Carbon-14 radioisotopes sometimes are selected over tritium because the exact position of the label can be selected based on the synthetic route employed for labeling. Carbon occurs in the skeleton of nearly all drug molecules, thereby allowing a chosen position for the radiolabeling site that is more likely to be metabolically stable.

Carbon-14-labeled compounds generally exhibit greater radiochemical stability than their tritium-labeled counterparts, as a result of the higher specific activity of tritium-labeled material. This has the effect of increasing the risk of significant autoradiolysis, (radiochemical decomposition), during storage or usage of the radiolabeled compound. Carbon-14 is also detectable at very low levels using scintillation counting, making it useful for studies in which doses that run close to the pharmacological threshold are common.

In some of the embodiments, compounds of the present disclosure (Formulas I-VI) can be labeled with at least one $^{14}C$ (e.g., compound VII or VIII). In some embodiments, as shown in Scheme 9, $^{14}C$ can be incorporated into the molecule by using a radiolabeled reagent, e.g., [1-$^{14}C$] acetaldehyde.

Scheme 9. [$^{14}C$]OCA

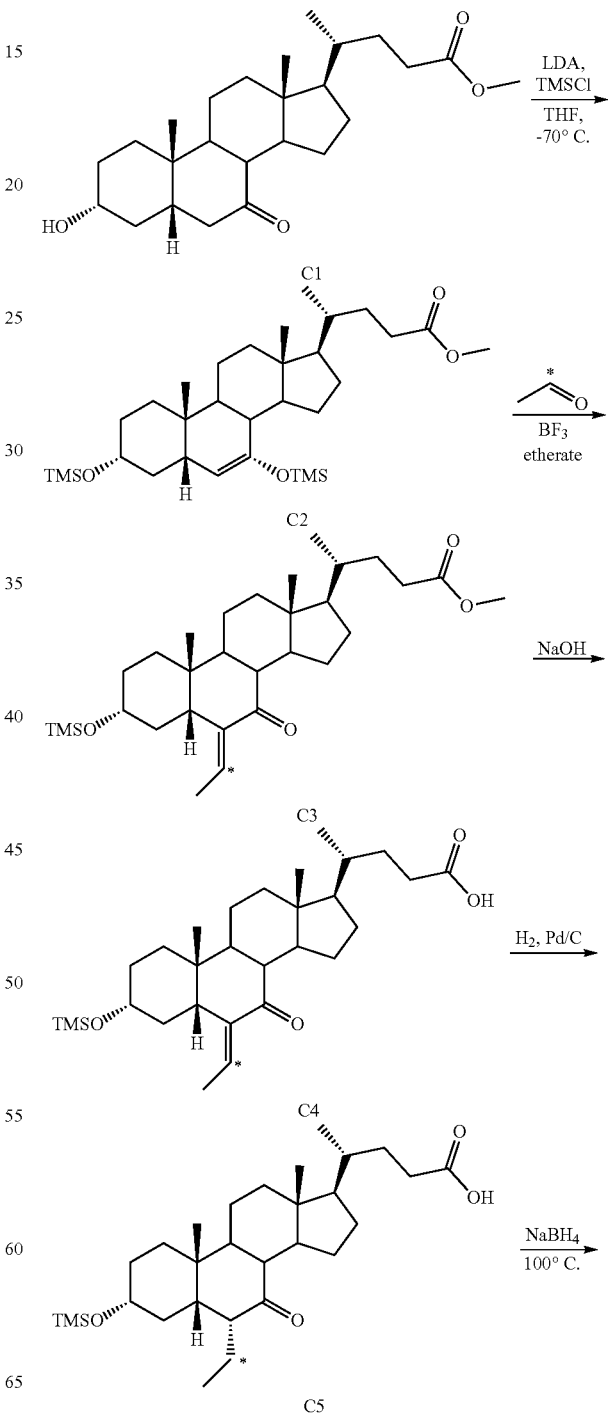

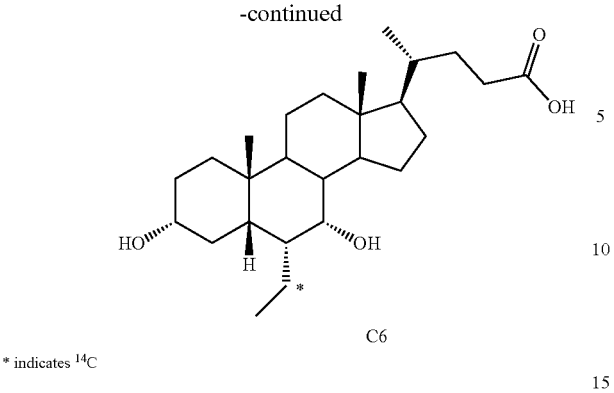

C6

* indicates $^{14}$C

In some embodiments, starting material, for example, compound C1, in a suitable solvent (e.g., THF) at about −65° C. to about −78° C., e.g., about −70° C., is treated with LDA in the presence of chlorotrimethylsilane or other suitable reagent for protection of C3-hydroxy (or any other hydroxy groups) to prepare compound C2. Compound C2 can be treated with [1-$^{14}$C]acetaldehyde and boron trifluoride etherate, in a suitable solvent, e.g., dichloromethane, at about −65° C. to about −78° C., e.g., −70° C., under inert atmosphere, e.g., nitrogen. To provide compound [$^{14}$C] C3. Compound [$^{14}$C]C3 can be treated with a base, e.g., sodium hydroxide, in a suitable solvent, e.g., methanol, at about 35° C. to about 55° C., e.g., 45° C. to afford compound [$^{14}$C]C4. Compound [$^{14}$C]C4 can be hydrogenated in the presence of sodium hydroxide, and 5% palladium on carbon at room temperature (e.g., at about 20° C., or about 25° C., or about 30° C.) and then at about 100° C. to about 130° C., e.g, 115° C. to [$^{14}$C]OCA ketone C5. [$^{14}$C]OCA ketone C5 can be purified (e.g., by HPLC). In some embodiments, the quality of the radiolabelled precursor [$^{14}$C]OCA ketone C5 is considered a critical control to the quality of [$^{14}$C]OCA C6 compound. Purified [$^{14}$C]OCA ketone C5 can be treated with a base, e.g., sodium hydroxide at about 75° C. to about 85° C., e.g., 80° C. and then aqueous sodium borohydride at approximately 100° C. to provide crude [$^{14}$C]OCA C6. Crude [$^{14}$C]OCA C6 can be purified (e.g., by column chromatography). In some embodiments, [$^{14}$C]OCA C6 material from the flash column can be treated with QuadraPure™ Tu palladium scavenger. In some embodiments, the filtered material can be further purified using preparative HPLC (e.g. using C18 column).

In some embodiments, [$^{14}$C]OCA is at high specific activity. In one of embodiments, [$^{14}$C]OCA high specific activity component can be combined with the OCA cold component at a ratio of [$^{14}$C]OCA to OCA to produce [$^{14}$C]OCA drug substance with the specific activity required for use in the [$^{14}$C]-OCA solution for administration (e.g., intravenous or oral) in clinical trial or other studies. The material can then be further diluted with OCA to produce [$^{14}$C]OCA drug substance with the specific activity required for use in the [$^{14}$C]-OCA Drug in Capsule in clinical trial or other study.

In some embodiments, e.g., as shown in Schemes 10 and 11, $^{14}$C can be incorporated into the molecule (compound of Formula I) at position C24 by using a radiolabeled reagent, e.g., K$^{14}$CN. The methods shown in Schemes 10 or 11 are based on obeticholic acid (OCA) and compound 100, respectively, as starting materials, but can be applied to any bile acid analogs of the present disclosure (i.e., compound of Formula I) to prepare $^{14}$C derivatives of compounds of Formulas I-VIII.

Scheme 10. [$^{14}$C-24]OCA

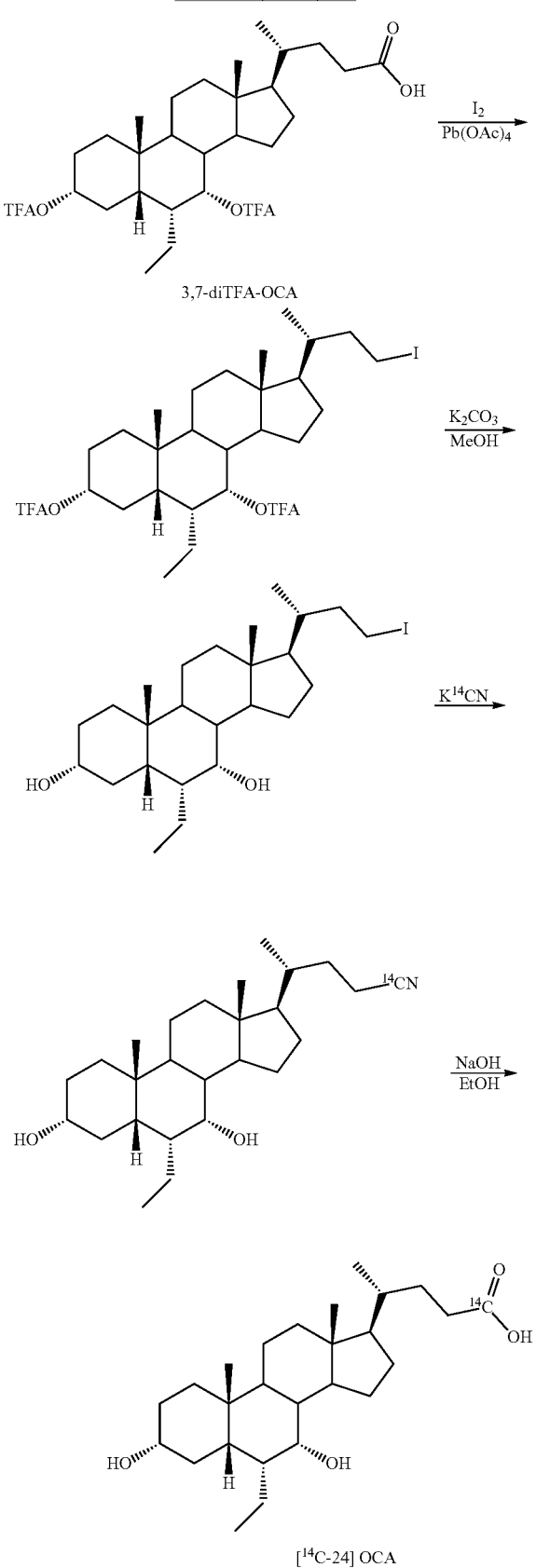

[$^{14}$C-24] OCA

3-O-glucuronides, 7-O-glucuronides, 11-O-glucuronides, 12-O-glucuronides, 24-O-glucuronides, or di- or triglucuronides, such as, for example, 3,7-diglucuronides or 3,7,11-triglucuronides. Glucuronides of Formula I can be prepared by methods known in the art and exemplified in Schemes 12 and 13.

In some embodiments, the present disclosure relates to 3-O-glucuronides of Formula I. The methods shown in Scheme 12 are based on obeticholic acid (OCA) as starting material, but can be applied to any bile acid analogs of the present disclosure (i.e., compound of Formula I) to prepare 3-O-glucuronidated compounds of Formulas I-VIII.

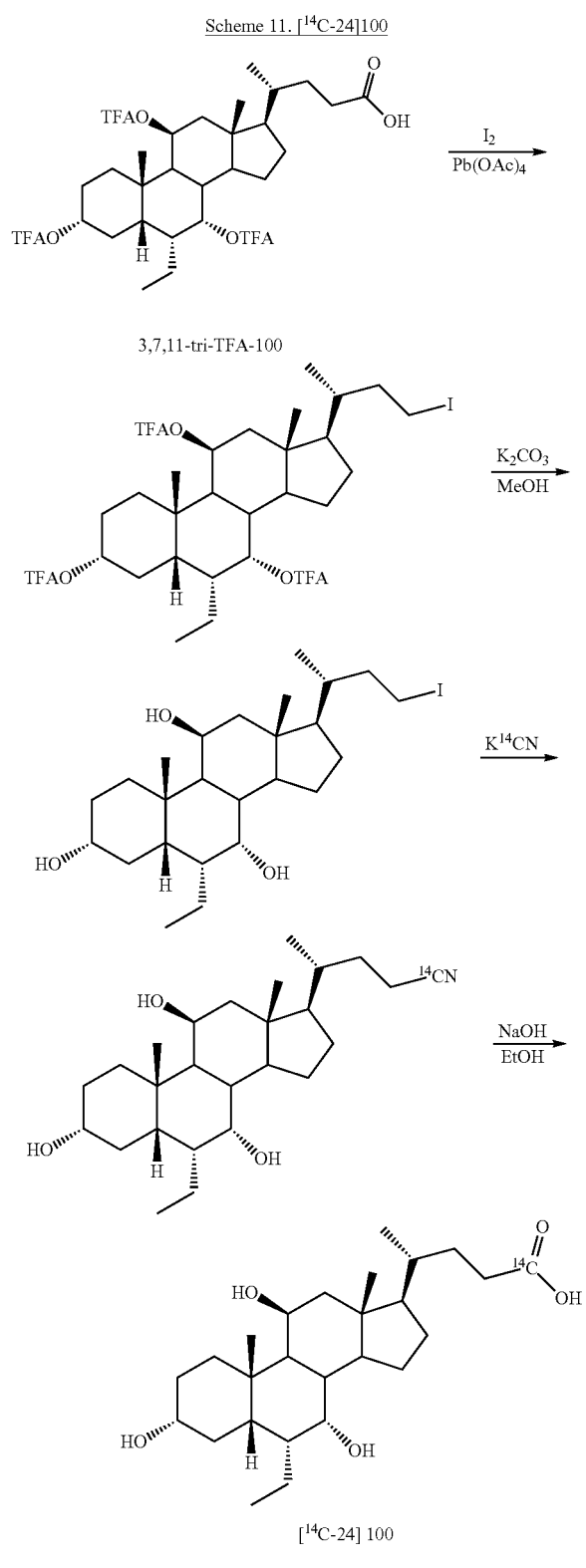

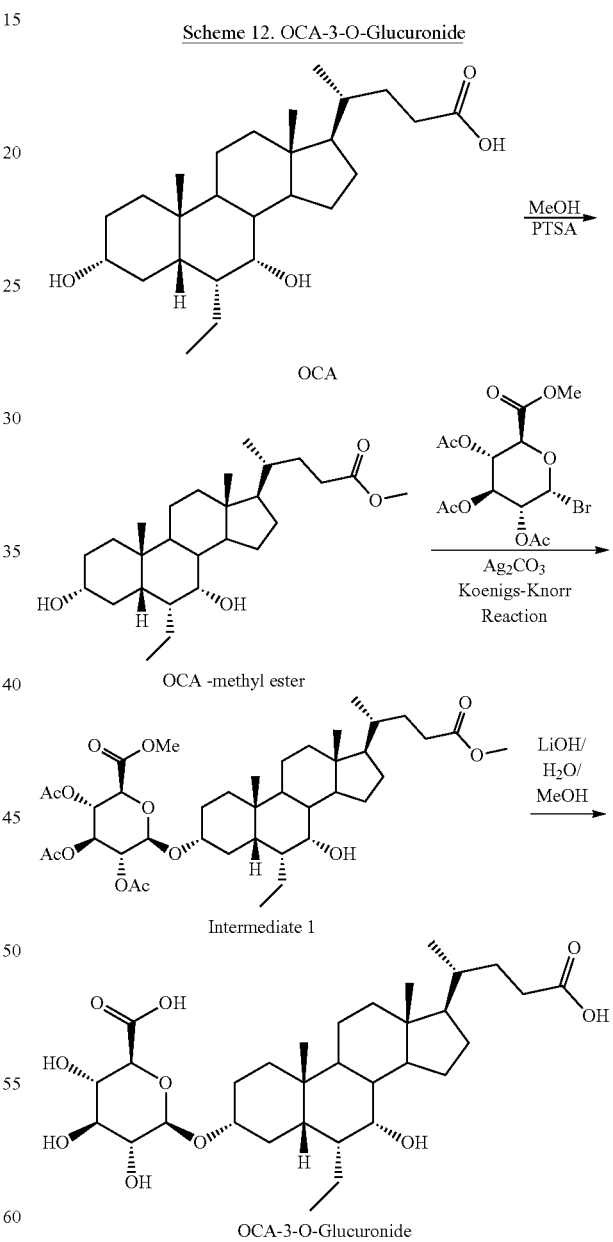

In some embodiments compounds of Formulas I, II, III, IV, V, VI, VII and VIII are glucuronides. Glucuronides of the present disclosure are prepared via methods known in the art, including Koenigs-Knorr reactions (Anne Wadouachi et. al., Molecules 16 (2011), 3933-3968). Glucuronated compounds of Formula I include, but are not limited to In some embodiments, the stating 3-hydroxy compound (e.g., OCA) can be protected, e.g., converted into methyl ester using, for example, methanol and para-toluene sulfonic acid. Protected compound, e.g., OCA-methyl ester, can be treated with silver carbonate and acetobromo-α-D-glucuronic acid methyl ester (protected glucuronic acid) to provide protected 3-O-glucuronide, e.g., protected OCA-3-O-glucuronide, which can be deprotected using methods known in the art to give 3-O-glucuronide of Formula I, e.g., OCA-3-O-glucuronide. In some embodiments, glucuronide starting material can be radiolabeled.

In some of the embodiments of the present disclosure, compounds of Formula I can be tritated. Tritiated compounds of Formula I can be prepared according to methods known in the art, for example, from corresponding 3-, 7-, 11-, or 12-keto compounds using tritiated reducing agent such as $NaBT_4$. In one of the embodiments, compounds of Formula I have tritium incorporated at C3 position. In one of the embodiments, compounds of Formula I have tritium incorporated at C11 position. In one of the embodiments, compounds of Formula I have tritium incorporated at C12 position. In one of the embodiments, tritium can be incorporated at C7 position.

In some embodiments, the present disclosure relates to 24-O-glucuronides of Formula I. The method shown in Scheme 13 is based on obeticholic acid (OCA) as starting material, but can be applied to any bile acid analogs of the present disclosure to prepare 24-O-glucuronidated compounds of Formulas I-VIII.

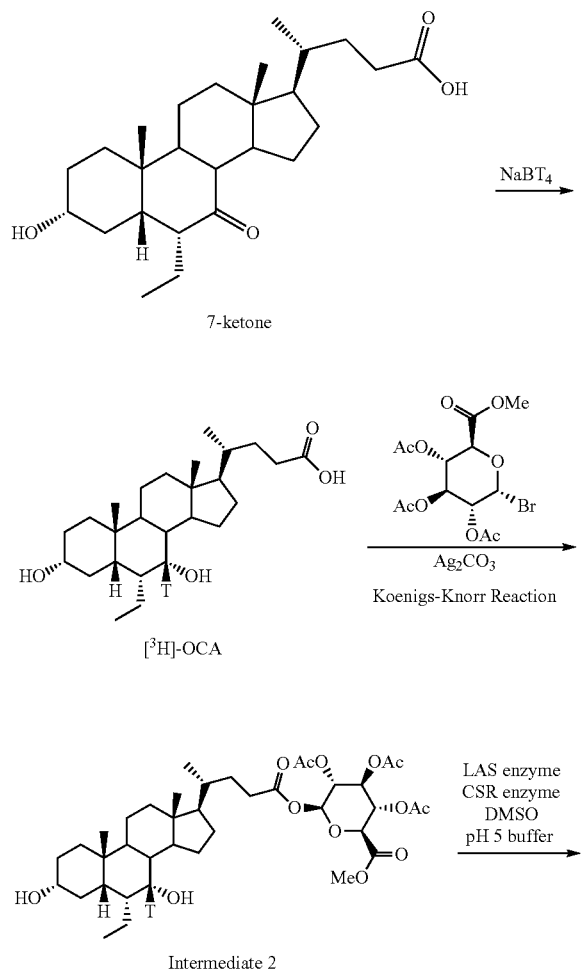

Scheme 13. [$^3$H]OCA-24-Glucuronide of OCA

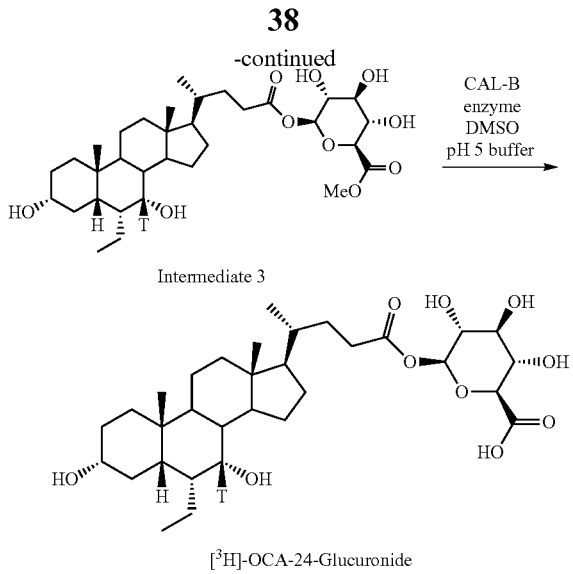

As shown in Scheme 13, C7-tritiated compound of Formula I, e.g., [$^3$H]OCA, can be prepared from C7-keto compound using tritiated reducing agent (e.g., $NaBT_4$). Radiolabeled and glucuronated compounds of Formula I, e.g., [$^3$H]OCA-24-Glucuronide of OCA, can be prepared by methods known in the art and described herein.

In some embodiments, compound of Formula I having carboxylic or hydroxy group(s), e.g., at C23 position, can be treated with protected glucuronic acid, e.g., acetobromo-α-D-glucuronic acid methyl ester, in the presence of silver carbonate to provide glucuronated compound, e.g., Intermediate 2. Intermediate 2 can be purified or used in the next step without purification. Enzyme-catalyzed consecutive deprotection (hydrolysis) affords glucuronated compound of Formula I, e.g., [$^3$H]OCA-24-glucuronide. Hydrolytic enzymes that can be used for deprotection include, but are not limited to transferases, hydrolases, and lyases. In some embodiments, deprotection may involve LAS enzyme, CSR enzyme, Cal-B enzyme and combinations thereof.

In some embodiments, the compound of Formula I-VIII can be purified using various methods including column chromatography (e.g., reversed phase chromatography). All radiolabeled compounds of the present disclosure can be characterised by various analytical method including, for example, mass spectrometry, HPLC and NMR ($^1$H, $^{13}$C, HMBC (Heteronuclear Multiple Bond Correlation)). In some embodiments, the compounds of Formulas I-VIII are analysed by NMR spectroscopy. Hydrogen and deuterium nuclei are different in their magnetic properties, therefore it is possible to distinguish between them by NMR spectroscopy. Deuterons will not be observed in a $^1$H NMR spectrum and conversely, protons will not be observed in a $^2$H NMR spectrum. Where small signals are observed in a $^1$H NMR spectrum of a highly deuterated sample, these are referred to as residual signals. They can be used to calculate the level of deuteration in a molecule. Analogous signals are not observed in $^2$H NMR spectra because of the low sensitivity of this technique compared to the $^1$H analysis. Deuterons typically exhibit very similar chemical shifts to their analogous protons. Analysis via $^{13}$C NMR spectroscopy is also possible: the different spin values of hydrogen (1/2) and deuterium (1) gives rise to different splitting multiplicities. NMR spectroscopy can be used to determine site-specific deuteration of molecules. In some embodiments, deuterium incorporation is determined by $^1$H-NMR. In one of the embodiments, the deuterium incorporation at each deuterium atom in compounds of the present disclosure is at least about 52.5% (enrichment factor is at least about 3500). In one of the embodiments, the deuterium incorporation at each deuterium atom in compounds of the present disclosure is at least about 60% (enrichment factor is at least about 4000). In one of the embodiments, the deuterium incorporation at each deuterium atom in compounds of the present disclosure is at least about 67.5% (enrichment factor is at least about 4500). In one of the embodiments, the deuterium incorporation at each deuterium atom in compounds of the present disclosure is at least about 75% (enrichment factor is at least about 5000). In one of the embodiments, the deuterium incorporation in compounds of the present disclosure is at least about 82.5% (enrichment factor is at least about 5500). In one of the embodiments, the deuterium incorporation in compounds of the present disclosure is at least about 90% (enrichment factor is at least about 6000). In one of the embodiments, the deuterium incorporation in compounds of the present disclosure is at least about 95% (enrichment factor is at least about 6333.3). In one of the embodiments, the deuterium incorporation in compounds of the present disclosure is at least about 97% (enrichment factor is at least about 6466.7). In one of the embodiments, the deuterium incorporation in compounds of the present disclosure is at least about 99% (enrichment factor is at least about 6600). In one of the embodiments, the deuterium incorporation in compounds of the present disclosure is at least about 99.5% (enrichment factor is at least about 6633.3).

The exemplified schemes and conditions are not intended to be limiting.

Pharmaceutical Compositions

A "pharmaceutical composition" is a formulation containing an active agent (e.g., isotopically-labeled compound of Formula I-VIII or a pharmaceutically acceptable salt thereof) in a form suitable for administration to a subject.

In some embodiments, the present disclosure pertains to a pharmaceutical composition comprising the compounds of Formulas I, II, III, IV, V, VI, VII or VIII and a pharmaceutically acceptable diluent, excipient or carrier. In some embodiments, the present disclosure pertains to a pharmaceutical composition comprising the compounds of Formula I and a pharmaceutically acceptable diluent, excipient or carrier. In some embodiments, the present disclosure pertains to a pharmaceutical composition comprising the compounds of Formula II and a pharmaceutically acceptable diluent, excipient or carrier. In some embodiments, the present disclosure pertains to a pharmaceutical composition comprising the compounds of Formula III and a pharmaceutically acceptable diluent, excipient or carrier. In some embodiments, the present disclosure pertains to a pharmaceutical composition comprising the compounds of Formula IV and a pharmaceutically acceptable diluent, excipient or carrier. In some embodiments, the present disclosure pertains to a pharmaceutical composition comprising the compounds of Formula V and a pharmaceutically acceptable diluent, excipient or carrier. In some embodiments, the present disclosure pertains to a pharmaceutical composition comprising the compounds of Formula VI and a pharmaceutically acceptable diluent, excipient or carrier. In some embodiments, the present disclosure pertains to a pharmaceutical composition comprising the compounds of Formula VII and a pharmaceutically acceptable diluent, excipient or carrier. In some embodiments, the present disclosure pertains to a pharmaceutical composition comprising the compounds of Formula VIII and a pharmaceutically acceptable diluent, excipient or carrier.

In one embodiment, the pharmaceutical composition is in bulk or in unit dosage form. The unit dosage form is any of a variety of forms, including, for example, a capsule, an IV bag, a tablet, a single pump on an aerosol inhaler, or a vial. The quantity of active ingredient in a unit dose of composition is an effective amount and is varied according to the particular treatment involved.

The present application provides pharmaceutical compositions comprising a compound of Formula I or a pharmaceutically acceptable salt thereof and a pharmaceutically acceptable diluent, excipient, or carrier. The pharmaceutical composition of the present disclosure can be administered enternally, orally, transdermally, pulmonarily, inhalationally, buccally, sublingually, intraperintoneally, subcutaneously, intramuscularly, intravenously, rectally, intrapleurally, intrathecally, intranasally, parenterally, or topically.

In particular, tablets, coated tablets, capsules, syrups, suspensions, drops or suppositories are used for enteral administration, solutions, preferably oily or aqueous solutions, furthermore suspensions, emulsions or implants, are used for parenteral administration, and ointments, creams or powders are used for topical application. Suitable dosage forms include, but are not limited to capsules, tablets, pellets, dragees, semi-solids, powders, granules, suppositories, ointments, creams, lotions, inhalants, injections, cataplasms, gels, tapes, eye drops, solution, syrups, aerosols, suspension, emulsion, which can be produced according to methods known in the art, for example as described below:

tablets: mixing of active ingredient/sand auxiliaries, compression of said mixture into tablets (direct compression), optionally granulation of part of mixture before compression.

capsules: mixing of active ingredient/s and auxiliaries to obtain a flowable powder, optionally granulating powder, filling powders/granulate into opened capsules, capping of capsules.

semi-solids (ointments, gels, creams): dissolving/dispersing active ingredient/s in an aqueous or fatty carrier; subsequent mixing of aqueous/fatty phase with complementary fatty/aqueous phase, homogenization (creams only).

suppositories (rectal and vaginal): dissolving/dispersing active ingredient/sin carrier material liquified by heat (rectal: carrier material normally a wax; vaginal: carrier normally a heated solution of a gelling agent), casting said mixture into suppository forms, annealing and withdrawal suppositories from the forms.

aerosols: dispersing/dissolving active agents in a propellant, bottling said mixture into an atomizer.

Suitable formulations for parenteral administration include aqueous solutions of the active compounds in water soluble form, for example, water-soluble salts and alkaline solutions. In addition, suspensions of the active compounds as appropriate oily injection suspensions may be administered. Suitable lipophilic solvents or vehicles include fatty oils, for example, sesame oil, or synthetic fatty acid esters, for example, ethyl oleate or triglycerides or polyethylene glycol-400 (the compounds are soluble in PEG-400). Aqueous injection suspensions may contain substances, which increase the viscosity of the suspension, including, for example, sodium carboxymethyl cellulose, sorbitol, and/or dextran, optionally, the suspension may also contain stabilizers. For administration as an inhalation spray, it is possible to use sprays in which the active ingredient is either dissolved or suspended in a propellant gas or propellant gas mixture (for example $CO_2$ or chlorofluorocarbons). The active ingredient is advantageously used here in micronized form, in which case one or more additional physiologically acceptable solvents may be present, for example ethanol. Inhalation solutions can be administered with the aid of conventional inhalers. In addition, stabilizers may be added.

Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

Dosage forms for the topical or transdermal administration include but are not limited to powders, sprays, ointments, pastes, creams, lotions, gels, solutions, patches and inhalants. In one embodiment, the active ingredient is mixed under sterile conditions with a pharmaceutically acceptable carrier, and with any preservatives, buffers or propellants that are required.

Suitable excipients are organic or inorganic substances, which are suitable for enteral (for example oral), parenteral or topical administration and do not react with the products of the disclosure, for example water, vegetable oils, benzyl alcohols, alkylene glycols, polyethylene glycols, glycerol triacetate, gelatine, carbohydrates, such as lactose, sucrose, mannitol, sorbitol or starch (maize starch, wheat starch, rice starch, potato starch), cellulose preparations and/or calcium phosphates, for example tricalcium phosphate or calcium hydrogen phosphate, magnesium stearate, talc, gelatine, tragacanth, methyl cellulose, hydroxypropylmethylcellulose, sodium carboxymethylcellulose, polyvinyl pyrrolidone and/or vaseline. If desired, disintegrating agents may be added such as the above-mentioned starches and also carboxymethyl-starch, cross-linked polyvinyl pyrrolidone, agar, or alginic acid or a salt thereof, such as sodium alginate. Auxiliaries include, without limitation, flow-regulating agents and lubricants, for example, silica, talc, stearic acid or salts thereof, such as magnesium stearate or calcium stearate, and/or polyethylene glycol.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, or sodium chloride in the composition. Prolonged absorption of the injectable compositions can be brought about by including in the composition an agent which delays absorption, for example, aluminum monostearate and gelatin. Sterile injectable solutions can be prepared by incorporating the active ingredient in the required amount in an appropriate solvent with one or a combination of ingredients enumerated above, as required, followed by filtered sterilization. Generally, dispersions are prepared by incorporating the active ingredient into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof. The compounds of the disclosure can be used, for example, for the production of injection preparations. The preparations indicated can be sterilized and/or can contain excipients such as lubricants, preservatives, stabilizers and/or wetting agents, emulsifiers, salts for affecting the osmotic pressure, buffer substances, colorants, flavourings and/or aromatizers. They can, if desired, also contain one or more further active compounds, e.g. one or more vitamins.

For administration by inhalation, the active ingredient is delivered in the form of an aerosol spray from pressured container or dispenser, which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active ingredient is formulated into ointments, salves, gels, or creams as generally known in the art.

One skilled in the art will appreciate that it is sometimes necessary to make routine variations to the dosage depending on, for example, the age and condition of the patient. The dosage will also depend on the route of administration.

One skilled in the art will recognize the advantages of certain routes of administration. The dosage administered will be dependent upon the age, health, and weight of recipient, kind of concurrent treatment, if any, frequency of treatment, and the nature of the effect desired.

In one embodiment, the pharmaceutical composition of the present application is administered orally.

Oral compositions generally include an inert diluent or an edible pharmaceutically acceptable carrier. They can be enclosed in gelatin capsules or compressed into tablets. For the purpose of oral therapeutic administration, the active ingredient can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring. For example, oral compositions can be tablets or gelatin capsules comprising the active ingredient together with a) diluents, e.g., lactose, dextrose, sucrose, mannitol, sorbitol, cellulose and/or glycine; b) lubricants, e.g., silica, talcum, stearic acid, its magnesium or calcium salt and/or polyethyleneglycol; for tablets also c) binders, e.g., magnesium aluminum silicate, starch paste, gelatin, tragacanth, methylcellulose, sodium carboxymethylcellulose and or polyvinylpyrrolidone; if desired d) disintegrants, e.g., starches, agar, alginic acid or its sodium salt, or effervescent mixtures; and/or e) absorbents, colorants, flavors and sweeteners.

Dragee cores are provided with suitable coatings, which, if desired, are resistant to gastric juices. For this purpose, concentrated saccharide solutions may be used, which may optionally contain gum arabic, talc, polyvinyl pyrrolidone, polyethylene glycol and/or titanium dioxide, lacquer solutions and suitable organic solvents or solvent mixtures.

In order to produce dosage form coatings resistant to gastric juices or to provide a dosage form affording the advantage of prolonged action (modified release dosage form), the tablet, dragee or pill can comprise an inner dosage and an outer dosage component me latter being in the form of an envelope over the former. The two components can be separated by an enteric layer, which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, acetyl alcohol, solutions of suitable cellulose preparations such as acetyl-cellulose phthalate, cellulose acetate or hydroxypropylmethyl-cellulose phthalate, are used. Dye stuffs or pigments may be added to the tablets or dragee coatings, for example, for identification or in order to characterize combinations of active compound doses. Suitable carrier substances are organic or inorganic substances which are suitable for enteral (e.g. oral) or parenteral administration or topical application and do not react with the compounds of disclosure, for example water, vegetable oils, benzyl alcohols, polyethylene glycols, gelatin, carbohydrates such as lactose or starch, magnesium stearate, talc and petroleum jelly.

Other pharmaceutical preparations, which can be used orally include push-fit capsules made of gelatine, as well as soft, sealed capsules made of gelatine and a plasticizer such as glycerol or sorbitol. The push-fit capsules can contain the active compounds in the form of granules, which may be mixed with fillers such as lactose, binders such as starches, and/or lubricants such as talc or magnesium stearate and, optionally, stabilizers. In soft capsules, the active compounds are preferably dissolved or suspended in suitable liquids, such as fatty oils, or liquid paraffin.

The liquid forms in which the compositions of the present disclosure may be incorporated for administration orally include aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinyl-pyrrolidone or gelatine.

Dosage forms for oral administration can comprise modified release formulations. The term "immediate release" is defined as a release of a compound of Formula I or a pharmaceutically acceptable salt thereof from a dosage form in a relatively brief period of time, generally up to about 60 minutes. The term "modified release" is defined to include delayed release, extended release, and pulsed release. The term "pulsed release" is defined as a series of releases of drug from a dosage form. The term "sustained release" or "extended release" is defined as continuous release of a compound of Formula I or a pharmaceutically acceptable salt thereof from a dosage form over a prolonged period of time.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active ingredient calculated to produce the desired therapeutic effect in association with the required pharmaceutical carrier. The specification for the dosage unit forms of the application are dictated by and directly dependent on the unique characteristics of the active ingredient and the particular therapeutic effect to be achieved.

In therapeutic applications, the dosages of the pharmaceutical compositions used in accordance with the application vary depending on the agent, the age, weight, and clinical condition of the recipient patient, and the experience and judgment of the clinician or practitioner administering the therapy, among other factors affecting the selected dosage.

Dosages of the compounds of the disclosure can range from about 0.01 mg/kg per day to about 500 mg/kg per day. In one of the embodiments, the daily dose is preferably between about 0.01 mg/kg and 10 mg/kg of body weight.

In one of the embodiments, the composition or formulation comprises about 0.1 mg to about 1500 mg of the compound of Formula I or a pharmaceutically acceptable salt thereof per dosage form. In another embodiment, the formulation or composition comprises about 1 mg to about 100 mg of the compound of Formula I or a pharmaceutically acceptable salt thereof. In another embodiment, the formulation comprises about 1 mg to about 50 mg. In another embodiment, the formulation comprises about 1 mg to about 30 mg. In another embodiment, the formulation comprises about 4 mg to about 26 mg. In another embodiment, the formulation comprises about 5 mg to about 25 mg. In one embodiment, the formulation comprises about 1 mg to about 5 mg. In one embodiment, the formulation comprises about 1 mg to about 2 mg.

An effective amount of a pharmaceutical agent is that which provides an objectively identifiable improvement as noted by the clinician or other qualified observer.

The pharmaceutical compositions can be included in a container, kit, pack, or dispenser together with instructions for administration.

The pharmaceutical compositions containing free form, salts, and/or solid state forms thereof of the present application may be manufactured in a manner that is generally known, e.g., by means of conventional mixing, dissolving, granulating, dragee-making, levigating, emulsifying, encapsulating, entrapping, or lyophilizing processes. Pharmaceutical compositions may be formulated in a conventional manner using one or more pharmaceutically acceptable carriers comprising excipients and/or auxiliaries that facilitate processing of the active ingredient into preparations that can be used pharmaceutically. Of course, the appropriate formulation is dependent upon the route of administration chosen.

Techniques for formulation and administration of the compounds of Formula I or the pharmaceutically acceptable salts thereof can be found in Remington: The Science and Practice of Pharmacy, 19$^{th}$ edition, Mack Publishing Co., Easton, Pa. (1995) or any later versions thereof.

The active ingredient can be prepared with pharmaceutically acceptable carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid.

Methods for preparation of such formulations will be apparent to those skilled in the art.

Methods of the Application

Some aspects of the present disclosure pertain to a method of treating, preventing, ameliorating or modulating a variety of liver, metabolic, kidney, cardiovascular, gastrointestinal and cancerous diseases, disorders or conditions using deuterated and/or radiolabeled bile acid derivatives of Formula I (including compounds of Formula II, III, IV, V, VI, and VII). In some embodiments, the compounds of Formula I or pharmaceutically acceptable salts thereof are used to improve metabolic profile, safety, tolerability and/or efficacy.

In some of the embodiments, this application pertains to a method of modulating FXR (e.g., activating FXR) in a subject in need thereof, comprising administering a therapeutically effective amount of a compound of Formula I or a pharmaceutically acceptable salt thereof.

In some embodiments, the present disclosure relates to a method of treating, preventing or ameliorating an FXR-mediated disease or disorder in a subject in need thereof, comprising administering a therapeutically effective amount of a compound of Formula I or a pharmaceutically acceptable salt thereof.

In some of the embodiments, this application pertains to a method of modulating TGR5 (e.g., activating TGR5) in a subject in need thereof, comprising administering a therapeutically effective amount of a compound of Formula I or a pharmaceutically acceptable salt thereof.

In some aspects, the present disclosure pertains to a compound of Formula I or a pharmaceutically acceptable salt thereof for treating or preventing or ameliorating an TGR5-mediated disease or disorder.

In certain embodiments, this disclosure pertains to a method of treating or preventing an FXR- or TGR5-mediated condition, disease or disorder in a subject in need thereof, comprising administering a composition comprising a therapeutically effective amount of a compound of Formula I or a pharmaceutically acceptable salt thereof.

In one embodiment, the disclosure relates to a method of treating or preventing chronic liver disease in a subject, comprising administering to the subject in need thereof an effective amount of a compound of Formula I or a pharmaceutically acceptable salt thereof. In one embodiment, the disclosure relates to a method of treating chronic liver disease. In one embodiment, the disclosure relates to a method of preventing chronic liver disease. In one embodiment, the FXR mediated liver disease is selected from a cholestatic liver disease such as primary biliary cirrhosis (PBC) also known as primary biliary cholangitis (PBC), primary sclerosing cholangitis (PSC), chronic liver disease, nonalcoholic fatty liver disease (NAFLD), nonalcoholic steatohepatitis (NASH), hepatitis C infection, alcoholic liver disease, liver damage due to progressive fibrosis, and liver fibrosis. Other examples of FXR mediated diseases also include portal hypertension, bile acid diarrhea, hyperlipidemia, high LDL-cholesterol, high HDL cholesterol, high triglycerides, and cardiovascular disease. Other liver diseases include cerebrotendinous xanthomatosis (CTX), drug induced cholestasis, intrahepatic cholestasis of pregnancy, parenteral nutrition associated cholestasis (PNAC), bacterial overgrowth or sepsis associated cholestasis, autoimmune hepatitis, chronic viral hepatitis, liver transplant associated graft versus host disease, living donor transplant liver regeneration, congenital hepatic fibrosis, choledocholithiasis, granulomatous liver disease, intra- or extrahepatic malignancy, Sjogren's syndrome, Sarcoidosis, Wilson's disease, Gaucher's disease, hemochromatosis, and alpha 1-antitrypsin deficiency.

In one embodiment, the disclosure relates to a method of treating or preventing one or more symptoms of cholestasis, including complications of cholestasis in a subject, comprising administering to the subject in need thereof an effective amount of a compound of Formula I or a pharmaceutically acceptable salt thereof. In one embodiment, the disclosure relates to a method of modulating one or more symptoms of cholestasis.

A compound of Formula I or a pharmaceutically acceptable salt thereof may be used for treating or preventing one or more symptoms of intrahepatic or extrahepatic cholestasis, including without limitation, biliary atresia, obstetric cholestasis, neonatal cholestasis, drug induced cholestasis, cholestasis arising from Hepatitis C infection, chronic cholestatic liver disease such as primary biliary cirrhosis (PBC), and primary sclerosing cholangitis (PSC).

In one embodiment, the present disclosure relates to a method of enhancing liver regeneration in a subject, comprising administering to the subject in need thereof an effective amount of a compound of Formula I or a pharmaceutically acceptable salt thereof. In one embodiment, the method is enhancing liver regeneration for liver transplantation.

In one embodiment, the disclosure relates to a method of treating or preventing fibrosis in a subject, comprising administering to the subject in need thereof an effective amount of a compound of Formula I or a pharmaceutically acceptable salt thereof.

Accordingly, as used herein, the term fibrosis refers to all recognized fibrotic disorders, including fibrosis due to pathological conditions or diseases, fibrosis due to physical trauma ("traumatic fibrosis"), fibrosis due to radiation damage, and fibrosis due to exposure to chemotherapeutics. As used herein, the term "organ fibrosis" includes but is not limited to liver fibrosis, fibrosis of the kidneys, fibrosis of lung, and fibrosis of the intestine.

In one of the embodiments, the renal disease is diabetic nephropathy, focal segmental glomerulosclerosis (FSGS), hypertensive nephrosclerosis, chronic glomerulonephritis, chronic transplant glomerulopathy, chronic interstitial nephritis, or polycystic kidney disease.

In some embodiments, the disclosure relates to a method of treating, preventing or modulating cardiovascular disease in a subject, comprising administering to the subject in need thereof an effective amount of a compound of Formula I or a pharmaceutically acceptable salt thereof. In one embodiment, cardiovascular disease is selected from atherosclerosis, arteriosclerosis, dyslipidemia, hypercholesteremia, hyperlipidemia, hyperlipoproteinemia, and hypertriglyceridemia.

The term "hyperlipidemia" refers to the presence of an abnormally elevated level of lipids in the blood. Hyperlipidemia can appear in at least three forms: (1) hypercholesterolemia, i.e., an elevated cholesterol level; (2) hypertriglyceridemia, i.e., an elevated triglyceride level; and (3) combined hyperlipidemia, i.e., a combination of hypercholesterolemia and hypertriglyceridemia. The term "dyslipidemia" refers to abnormal levels of lipoproteins in blood plasma including both depressed and/or elevated levels of lipoproteins (e.g., elevated levels of LDL, VLDL and depressed levels of HDL).

In one embodiment, the disclosure relates to a method selected from reducing cholesterol levels or modulating cholesterol metabolism, catabolism, absorption of dietary cholesterol, and reverse cholesterol transport in a subject, comprising administering to the subject in need thereof an effective amount of a compound of Formula I or a pharmaceutically acceptable salt thereof.

In another embodiment, the disclosure relates to a method of treating or preventing a disease affecting cholesterol, triglyceride, or bile acid levels in a subject, comprising administering to the subject in need thereof an effective amount of a compound of Formula I or a pharmaceutically acceptable salt thereof.

In one embodiment, the disclosure relates to a method of lowering triglycerides in a subject, comprising administering to the subject in need thereof an effective amount of a compound of Formula I or a pharmaceutically acceptable salt thereof.

In one embodiment, the disclosure relates to a method of preventing a disease state associated with an elevated cholesterol level in a subject. In one embodiment, the disease state is selected from coronary artery disease, angina pectoris, carotid artery disease, strokes, cerebral arteriosclerosis, and xanthoma.

In one embodiment, the disclosure relates to a method of treating or preventing a lipid disorder in a subject, comprising administering to the subject in need thereof an effective amount of a compound of Formula I or a pharmaceutically acceptable salt thereof.

In one embodiment, the disclosure relates to a method of treating or preventing one or more symptoms of disease affecting lipid metabolism (i.e., lipodystrophy) in a subject, comprising administering to the subject in need thereof an effective of a compound of Formula I or a pharmaceutically acceptable salt thereof. In one embodiment, the disclosure relates to a method of treating one or more symptoms of a disease affecting lipid metabolism. In one embodiment, the disclosure relates to a method of preventing one or more symptoms of a disease affecting lipid metabolism. In one embodiment, the disclosure relates to a method of decreasing lipid accumulation in a subject.

In one embodiment, the disclosure relates to a method of treating, preventing or modulating gastrointestinal disease in a subject, comprising administering to the subject in need thereof an effective amount of a compound of Formula I or a pharmaceutically acceptable salt thereof. In some embodiments, the gastrointestinal disease is selected from inflammatory bowel disease (IBD), irritable bowel syndrome (IBS), bacterial overgrowth, malabsorption, post-radiation colitis, and microscopic colitis. In one embodiment, the inflammatory bowel disease is selected from Crohn's disease and ulcerative colitis.

In one embodiment, the disclosure relates to a method of treating, preventing or modulating renal disease in a subject, comprising administering to the subject in need thereof an effective amount of a compound of Formula I or a pharmaceutically acceptable salt thereof. In some embodiments, the renal disease is selected from diabetic nephropathy, focal segmental glomerulosclerosis (FSGS), hypertensive nephrosclerosis, chronic glomerulonephritis, chronic transplant glomerulopathy, chronic interstitial nephritis, and polycystic kidney disease.

In one embodiment, the disclosure relates to a method of treating or preventing metabolic disease in a subject, comprising administering to the subject in need thereof an effective amount of a compound of Formula I or a pharmaceutically acceptable salt thereof. In one embodiment, the metabolic disease is selected from insulin resistance, hyperglycemia, diabetes mellitus, diabesity, and obesity. In one embodiment, the diabetes mellitus is type I diabetes. In one embodiment, the diabetes mellitus is type II diabetes.

Diabetes mellitus, commonly called diabetes, refers to a disease or condition that is generally characterized by metabolic defects in production and utilization of glucose which result in the failure to maintain appropriate blood sugar levels in the body.

In the case of type II diabetes, the disease is characterized by insulin resistance, in which insulin loses its ability to exert its biological effects across a broad range of concentrations. This resistance to insulin responsiveness results in insufficient insulin activation of glucose uptake, oxidation and storage in muscle and inadequate insulin repression of lipolysis in adipose tissue and of glucose production and secretion in liver. The resulting condition is elevated blood glucose, which is called "hyperglycemia". Uncontrolled hyperglycemia is associated with increased and premature mortality due to an increased risk for microvascular and macrovascular diseases, including retinopathy (the impairment or loss of vision due to blood vessel damage in the eyes); neuropathy (nerve damage and foot problems due to blood vessel damage to the nervous system); and nephropathy (kidney disease due to blood vessel damage in the kidneys), hypertension, cerebrovascular disease, and coronary heart disease. Therefore, control of glucose homeostasis is a critically important approach for the treatment of diabetes.

Insulin resistance has been hypothesized to unify the clustering of hypertension, glucose intolerance, hyperinsulinemia, increased levels of triglyceride and decreased HDL cholesterol, and central and overall obesity. The association of insulin resistance with glucose intolerance, an increase in plasma triglyceride and a decrease in high-density lipoprotein cholesterol concentrations, hypertension, hyperuricemia, smaller denser low-density lipoprotein particles, and higher circulating levels of plasminogen activator inhibitor-1, has been referred to as "Syndrome X". Accordingly, methods of treating or preventing any disorders related to insulin resistance including the cluster of disease states, conditions or disorders that make up "Syndrome X" are provided.

In one embodiment, the invention relates to a method of treating, preventing or ameliorating metabolic syndrome in a subject, comprising administering to the subject in need thereof an effective amount of a compound of the disclosure or a pharmaceutically acceptable salt thereof.

In some embodiments, the disclosure relates to a method of treating, preventing, ameliorating or modulating cancer in a subject, comprising administering to the subject in need thereof an effective amount of a compound of Formula I or a pharmaceutically acceptable salt thereof. In some embodiments, the cancer is selected from hepatocellular carcinoma (HCC), also known as malignant hepatoma, cholangiocellular carcinoma, colorectal cancer, gastric cancer, renal cancer, prostate cancer, adrenal cancer, pancreatic cancer, breast cancer, bladder cancer, salivary gland cancer, ovarian cancer, uterine body cancer, and lung cancer.

In one of the embodiments, the hepatocellular carcinoma is selected from the group consisting of early stage hepatocellular carcinoma, non-metastatic hepatocellular carcinoma, primary hepatocellular carcinoma, advanced hepatocellular carcinoma, locally advanced hepatocellular carcinoma, metastatic hepatocellular carcinoma, hepatocellular carcinoma in remission, or recurrent hepatocellular carcinoma.

In another embodiment, at least one of an agent selected from Sorafenib, Sunitinib, Erlotinib, or Imatinib is co-administered with the crystalline form of the present disclosure to treat cancer. In one embodiment, at least one of an agent selected from abarelix, aldeleukin, allopurinol, altretamine, amifostine, anastozole, bevacizumab, capecitabine, carboplatin, cisplatin, docetaxel, doxorubicin, erlotinib, exemestane, 5-fluorouracil, fulvestrant, gemcitabine, goserelin acetate, irinotecan, lapatinib ditosylate, letozole, leucovorin, levamisole, oxaliplatin, paclitaxel, panitumumab, pemetrexed disodium, profimer sodium, tamoxifen, topotecan, and trastuzumab is co-administered with the compound of the invention to treat cancer.

Appropriate treatment for cancers depends on the type of cell from which the tumor derived, the stage and severity of the malignancy, and the genetic abnormality that contributes to the tumor.

Cancer staging systems describe the extent of cancer progression. In general, the staging systems describe how far the tumor has spread and puts patients with similar prognosis and treatment in the same staging group. In general, there are poorer prognoses for tumors that have become invasive or metastasized.

In one type of staging system, cases are grouped into four stages, denoted by Roman numerals I to IV. In stage I, cancers are often localized and are usually curable. Stage II and IIIA cancers are usually more advanced and may have invaded the surrounding tissues and spread to lymph nodes. Stage IV cancers include metastatic cancers that have spread to sites outside of lymph nodes.

Another staging system is TNM staging which stands for the categories: Tumor, Nodes, and Metastases. In this system, malignancies are described according to the severity of the individual categories. For example, T classifies the extent of a primary tumor from 0 to 4 with 0 representing a malignancy that does not have invasive activity and 4 representing a malignancy that has invaded other organs by extension from the original site. N classifies the extent of lymph node involvement with 0 representing a malignancy with no lymph node involvement and 4 representing a malignancy with extensive lymph node involvement. M classifies the extent of metastasis from 0 to 1 with 0 representing a malignancy with no metastases and 1 representing a malignancy with metastases.

These staging systems or variations of these staging systems or other suitable staging systems may be used to describe a tumor such as hepatocellular carcinoma. Few options only are available for the treatment of hepatocellular cancer depending on the stage and features of the cancer. Treatments include surgery, treatment with Sorafenib, and targeted therapies. In general, surgery is the first line of treatment for early stage localized hepatocellular cancer. Additional systemic treatments may be used to treat invasive and metastatic tumors.

In one embodiment, the disclosure relates to a method of treating, preventing or ameliorating gallstones in a subject, comprising administering to the subject in need thereof an effective amount of a compound of Formula I or a pharmaceutically acceptable salt thereof.

Presence of gallstones in the gallbladder may lead to acute cholecystitis, an inflammatory condition characterized by retention of bile in the gallbladder and often secondary infection by intestinal microorganisms, predominantly *Escherichia coli*, and *Bacteroides* species. Presence of gallstones in other parts of the biliary tract can cause obstruction of the bile ducts, which can lead to serious conditions such as ascending cholangitis or pancreatitis.

In one embodiment, the disclosure relates to a method of treating, preventing or ameliorating a cholesterol gallstone disease.

In one embodiment, the disclosure relates to a method of treating or preventing neurological disease in a subject, comprising administering to the subject in need thereof an effective amount of a compound of Formula I or a pharmaceutically acceptable salt thereof. In one embodiment, the neurological disease is stroke.

In one embodiment, the disclosure relates to a method of regulating the expression level of one or more genes involved in bile acid homeostasis.

In one embodiment, the disclosure relates to a method of down regulating the expression level of one or more genes selected from CYP7α1 and SREBP-IC in a cell by administering to the cell a crystalline form of OCA. In one embodiment, the disclosure relates to a method of up regulating the expression level of one or more genes selected from OSTα, OSTβ, BSEP, SHP, UGT2B4, MRP2, FGF-19, PPARγ, PLTP, APOCII, and PEPCK in a cell by administering to the cell a crystalline form of the invention.

The amount of a compound of Formula I or a pharmaceutically acceptable salt thereof which is required to achieve the desired biological effect will depend on a number of factors such as the use for which it is intended, the means of administration, and the recipient, and will be ultimately at the discretion of the attendant physician or veterinarian. In general, a typical daily dose for the treatment of a FXR mediated disease and condition, for instance, may be expected to lie in the range of from about 0.01 mg/kg to about 100 mg/kg. This dose may be administered as a single unit dose or as several separate unit doses or as a continuous infusion. Similar dosages would be applicable for the treatment of other diseases, conditions and therapies including the prevention and treatment of cholestatic liver diseases.

In some embodiment, the disclosure relates to a method of using an effective amount of a compound of Formula I (including compounds of Formula II, III, IV, V, VI, VII and VIII) or a pharmaceutically acceptable salt thereof as metabolic or pharmacokinetic probe. In certain embodiments, the disclosure relates to a method of using an effective amount of a compound of Formula I or a pharmaceutically acceptable salt thereof as metabolic probe. In certain embodiments, the disclosure relates to a method of using an effective amount of a compound of Formula I or a pharmaceutically acceptable salt thereof as pharmacokinetic probe.

The disclosure also relates to the manufacture of a medicament for treating, preventing, ameliorating or modulating a disease or condition (e.g., a disease or condition mediated by FXR or TGR5), wherein the medicament comprises a compound of Formula I or a pharmaceutically acceptable salt thereof.

The disclosure also relates to the manufacture of a medicament for treating, preventing, ameliorating or modulating a disease or condition (e.g., a disease or condition mediated by FXR or TGR5), wherein the medicament comprises composition comprising a compound of Formula I or a pharmaceutically acceptable salt thereof and a pharmaceutically acceptable excipient.

All percentages and ratios used herein, unless otherwise indicated, are by weight. Other features and advantages of the present application are apparent from the different examples. The provided examples illustrate different components and methodology useful in practicing the present application. The examples do not limit the claimed application. Based on the present disclosure the skilled artisan can identify and employ other components and methodology useful for practicing the present application.

EXAMPLES

Example 1: $d_5$-OCA

Method 1:

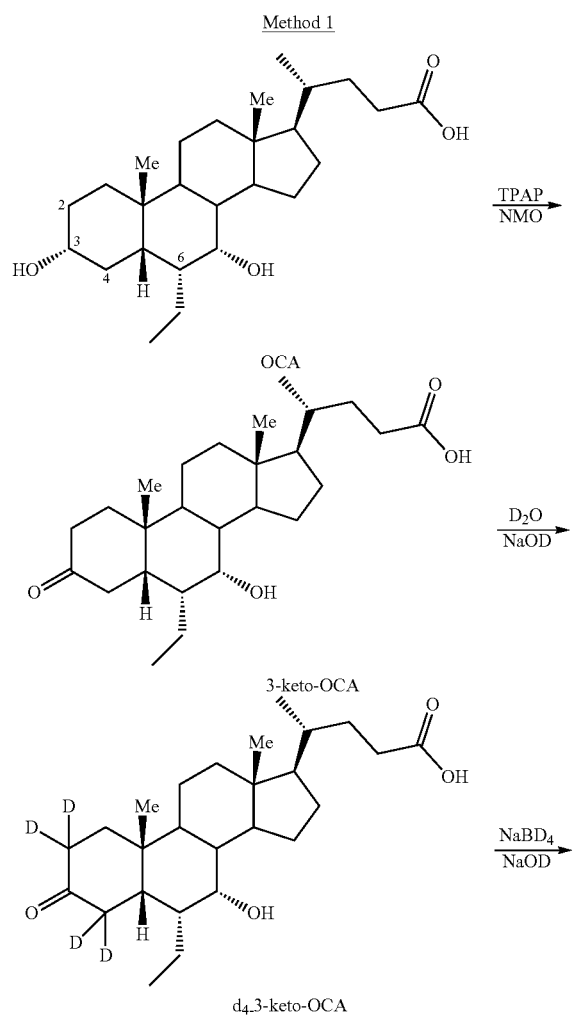

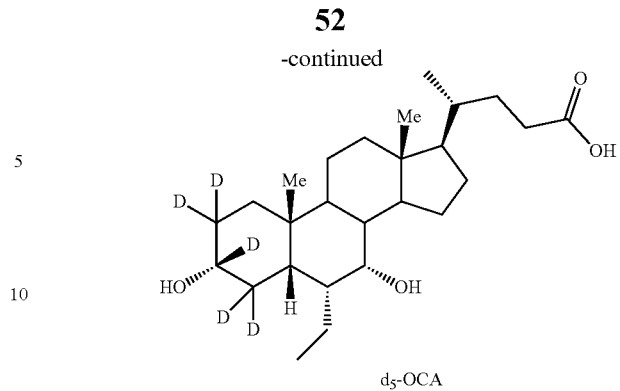

3-Keto-OCA (52.5 g, 125.6 mmol), prepared by oxidizing OCA with TPAP/NMO, was dissolved in 400 mL of $D_2O$ and NaOD (40% in $D_2O$, 35 mL) was added. The mixture was stirred at 90° C. for 4 hours. $NaBD_4$ (7.77 g, 185 mmol) was added portionwise and stirring continued for 2 hours at 90° C. The mixture was cooled to room temperature and quenched with aqueous citric acid. The product was extracted with EtOAc (2×). The combined organic layers were washed with brine, dried over $Na_2SO_4$ and concentrated. The material was taken up in 1 L of water and 10 g of NaOH. The solution was slowly acidified with 10% HCl until pH 2. The precipitate is collected and washed with water and dried in vacuo.

Another batch of 3-keto-OCA (18.4 g, 44 mmol) was converted and combined with the first batch. The combined batches had a HPLC-purity around 95%. Pure $d_5$-OCA was obtained by means of column chromatography (silica; DCM/MeOH 2-10%). The pure material, $d_5$-OCA, was dissolved in 3 L of water containing 16 g of NaOH, and the solution was slowly acidified with 10% HCl (aq) until pH 2. The precipitate was filtered and washed with water, then dried in vacuo (43 g, 61%). Chemical purity: 99.4%; Isotopic purity: >95%. $^1$H NMR (300 MHz, $CD_3OD$) confirmed the identity of this compound (FIG. 1).

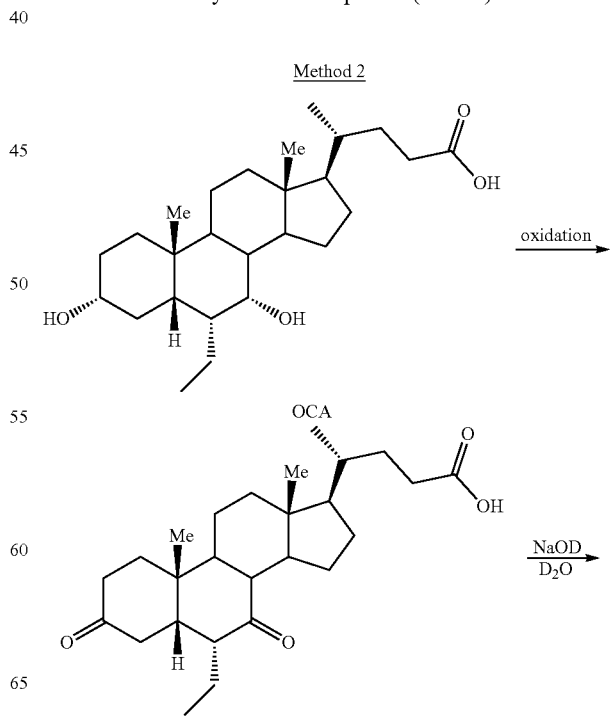

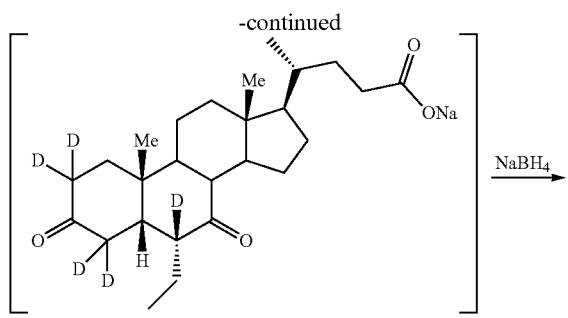

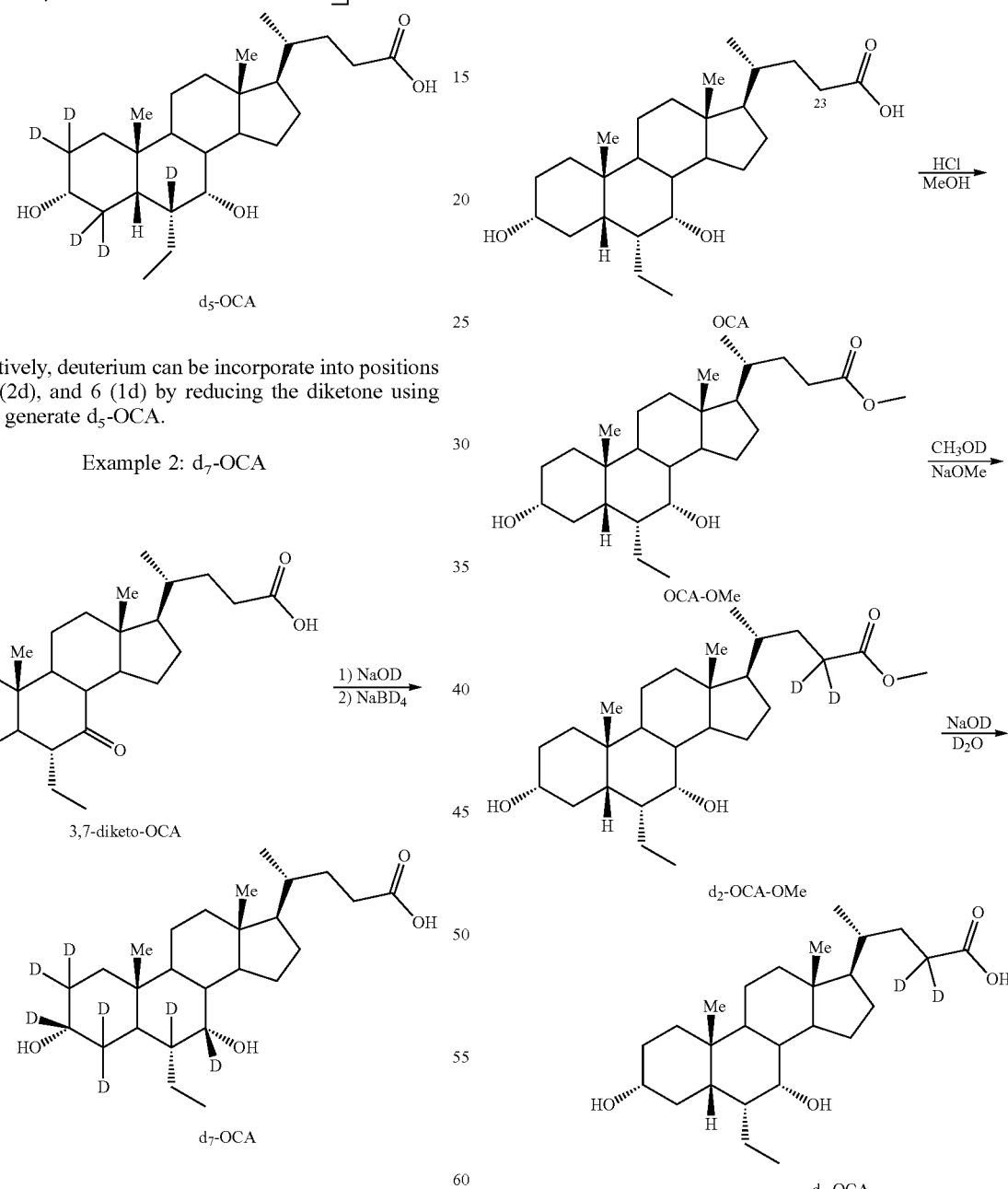

Alternatively, deuterium can be incorporate into positions 2 (2d), 4 (2d), and 6 (1d) by reducing the diketone using NaBH₄ to generate d₅-OCA.

Figure 2:
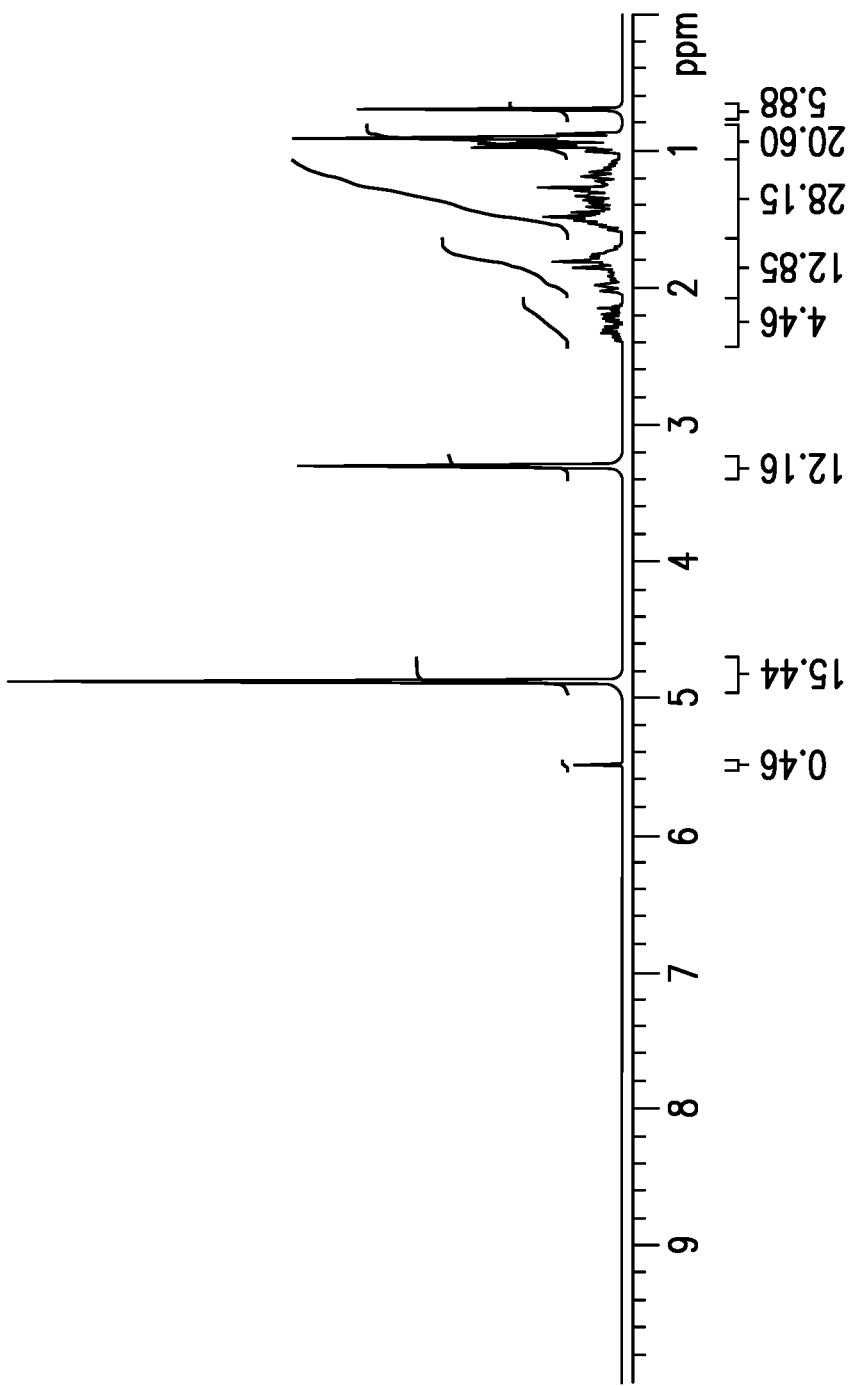
FIG. 2 shows the $^1$H NMR spectrum obtained from d$_7$-OCA.

Example 2: d₇-OCA 3,7-diketo-OCA (100 mg, 0.24 mmol) was dissolved in 0.75 mL of D₂O and 10 drops of NaOD (40% in D₂O) were added. The mixture was stirred for 2 hours at 90° C. then NaBD₄ (21 mg, 0.50 mmol) was added. Stirring continued at 90° C. for another 2 hours. The mixture was cooled to room temperature and quenched with aqueous citric acid. The product was extracted with EtOAc (2×). The combined organic layers were washed with brine, dried over Na₂SO₄ and concentrated. The crude material was purified by means of column chromatography (silica; chloroform/HOAc 9:1). The appropriate fractions were collected and concentrated redissolved in methanol and precipitated with water. After concentration d₇-OCA was obtained as a white solid (75 mg, 75%). ¹H NMR (300 MHz, CD₃OD) confirmed the identity of this compound (FIG. 2).

Example 3: C23(d₂)-OCA

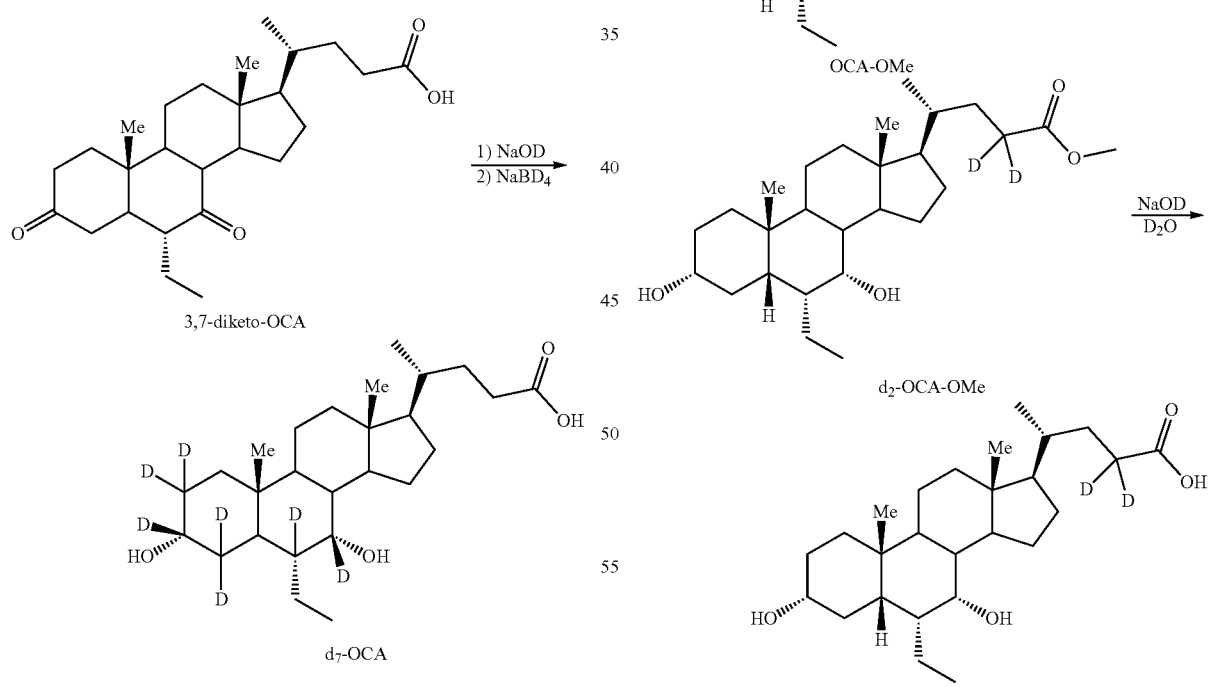

Figure 3:
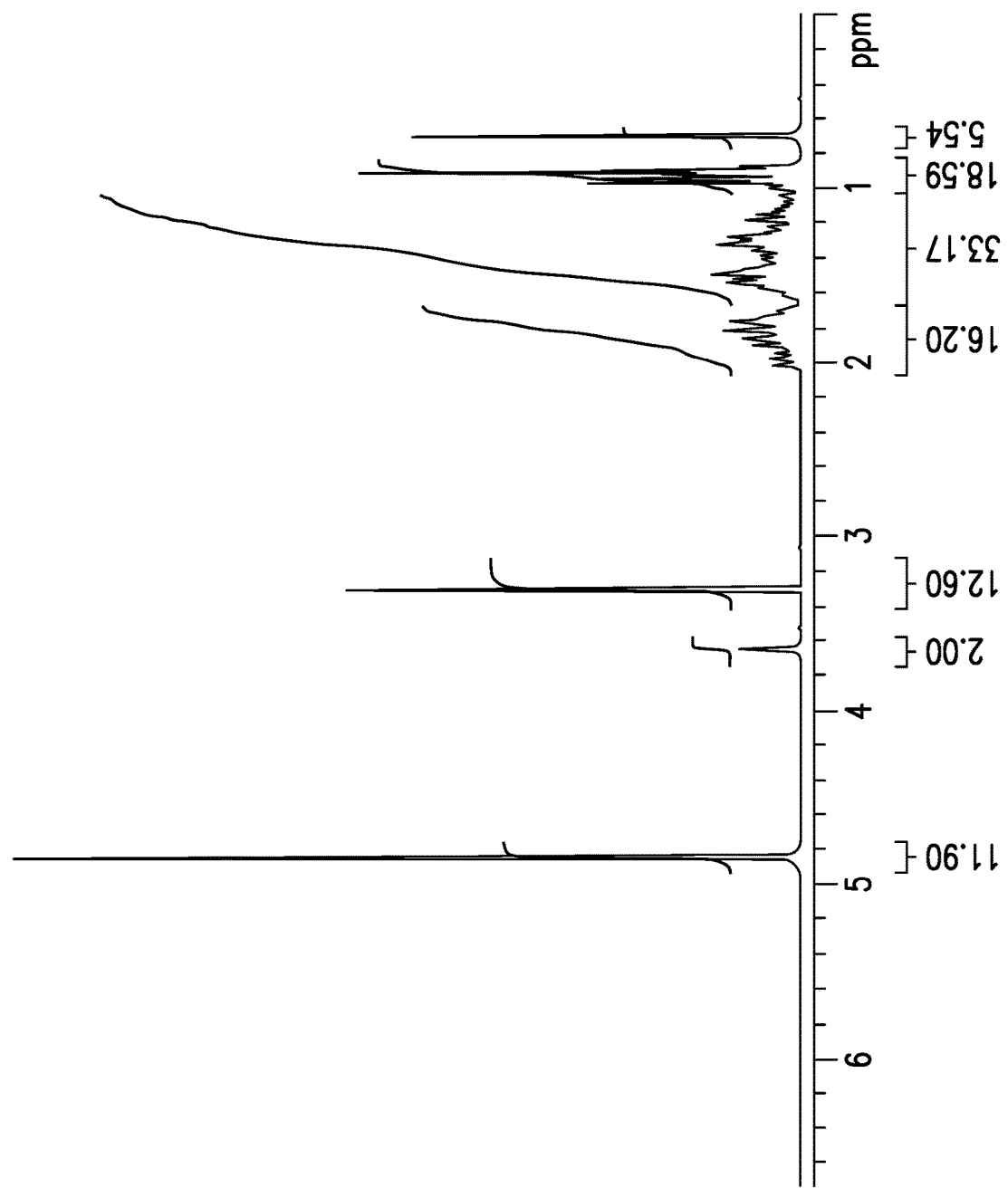
FIG. 3 shows the $^1$H NMR spectrum obtained from d$_2$-OCA (C23(d$_2$)-OCA).

OCA-OMe (methyl ester) prepared from OCA using methanol and HCl or p-toluenesulfonic acid. Sodium (0.4 g, 17.8 mmol) was added to 15 mL of CH₃OD and dissolved completely before the OCA-OMe (3.5 g, 8.1 mmol) was added. The mixture was stirred at 70° C. overnight. The solvent is evaporated and fresh CH₃OD (15 mL) was added. The mixture was refluxed for another 6 hours and cooled to room temperature. NaOD (40% in D₂O, 1 mL) was added and the mixture was stirred overnight. After concentration, the material was redissolved in chloroform with 2% HOAc and concentrated again. The crude material was purified by means of column chromatography (silica; DCM/MeOH 5-10%) affording d₂-OCA as a white solid (2.6 g, 62%). ¹H NMR (300 MHz, CD₃OD) confirmed the identity of this compound (FIG. 3).

Example 4: C3(d)-C7(d)-C23(d₂)-OCA

Figure 4:
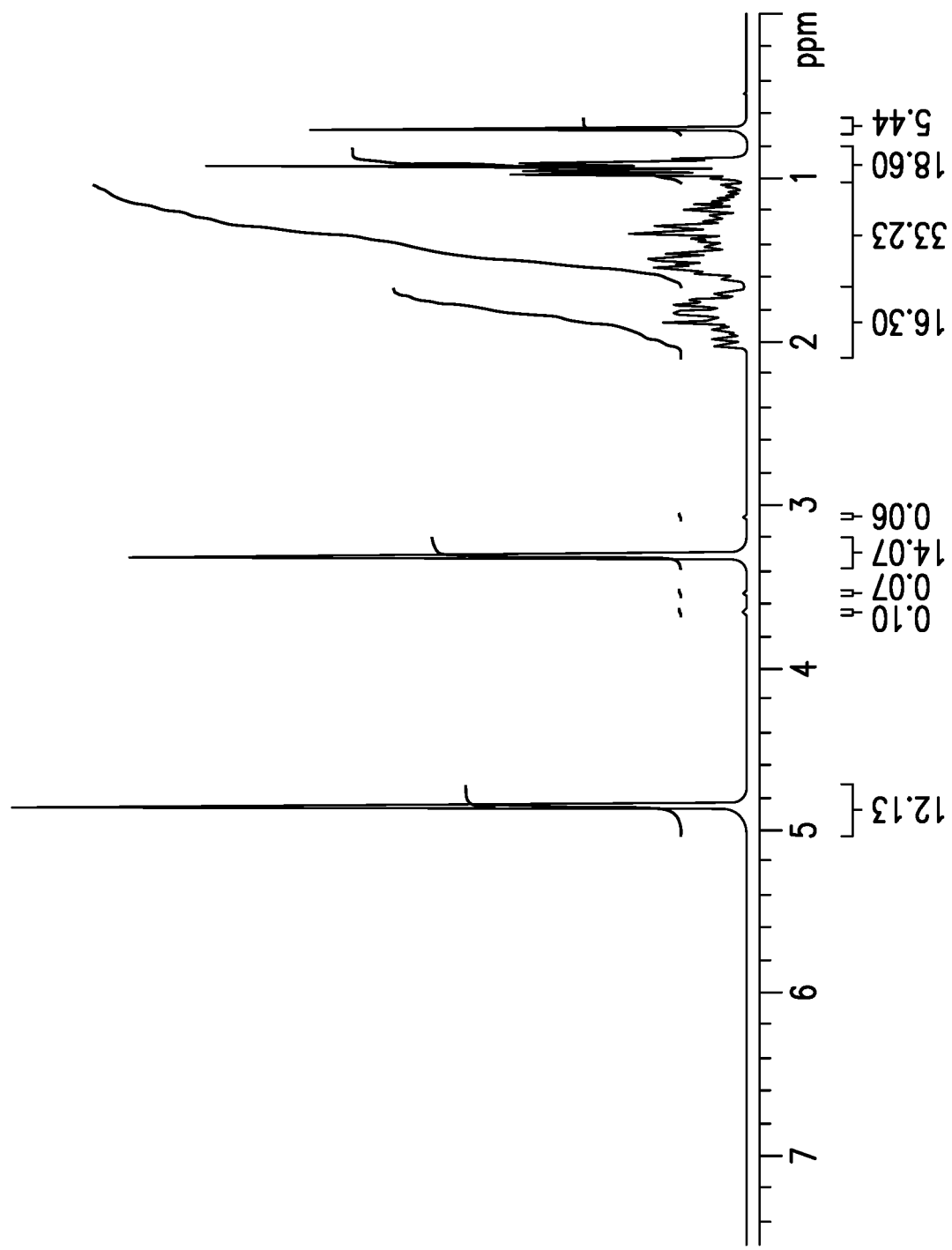
FIG. 4 shows the $^1$H NMR spectrum obtained from d$_4$-OCA (C3(d)-C7(d)-C23(d$_2$)-OCA).

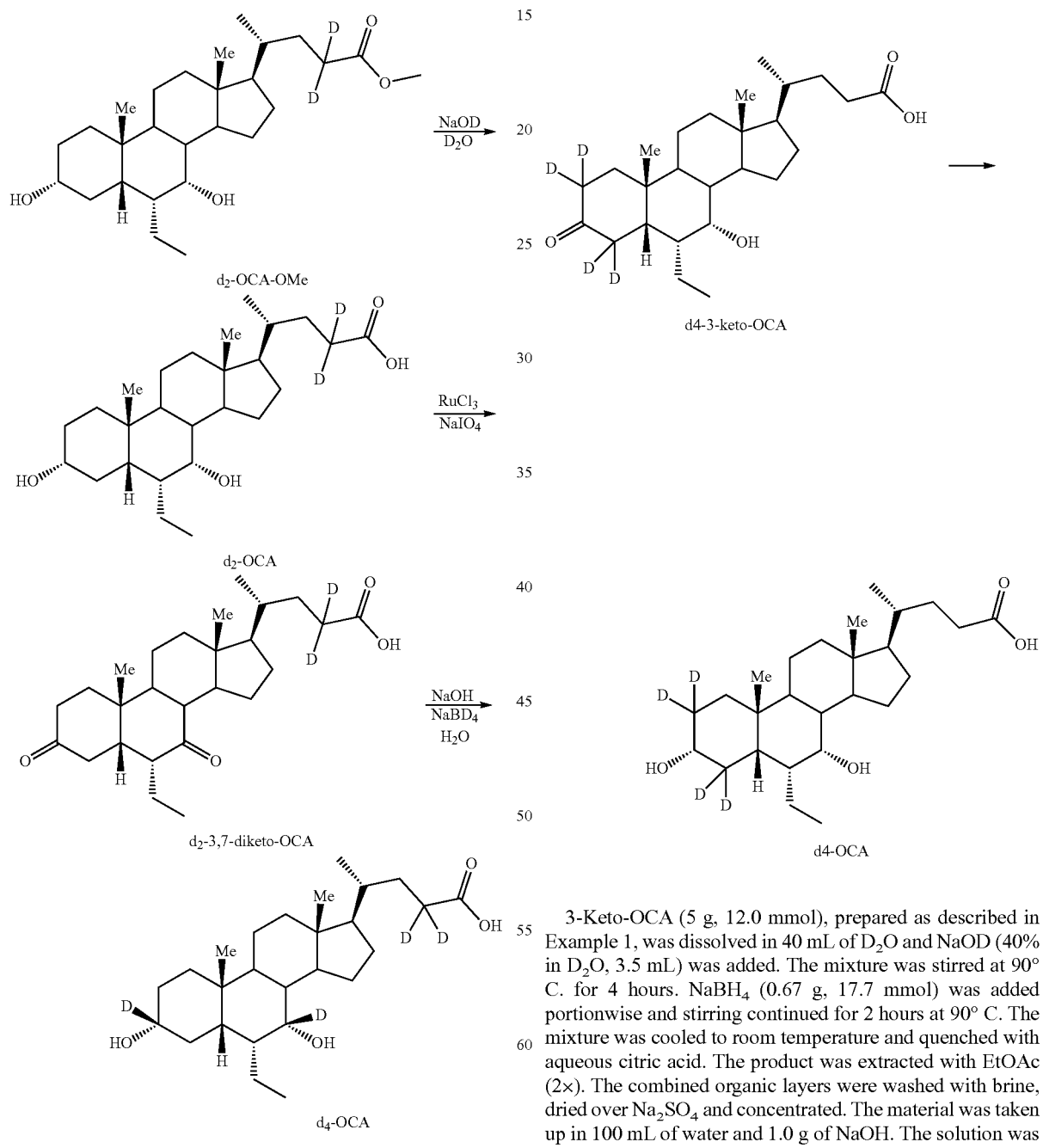

d₂-OCA-OMe d₂-OCA d₂-3,7-diketo-OCA d₄-OCA 3,7-Diketo-(d₂)OCA (1.6 g, 3.8 mmol) was dissolved in 10 mL of H₂O and NaOH (0.15 g, 3.8 mmol) was added. The mixture was warmed to 90° C. and NaBD₄ (0.64 g, 15.3 mmol) was added. Stirring continued at 90° C. for another 2 hours. The mixture was cooled to room temperature and quenched with aqueous citric acid. The product was extracted with EtOAc (2×). The combined organic layers were washed with brine, dried over Na₂SO₄ and concentrated. The crude material was purified by means of column chromatography (silica; DCM/MeOH 5-10%) affording d₄-OCA as a white solid (1.1 g, 69%). ¹H NMR (300 MHz, CD₃OD) confirmed the identity of this compound (FIG. 4).

Example 5: C2(2d)-C4(2d)-OCA

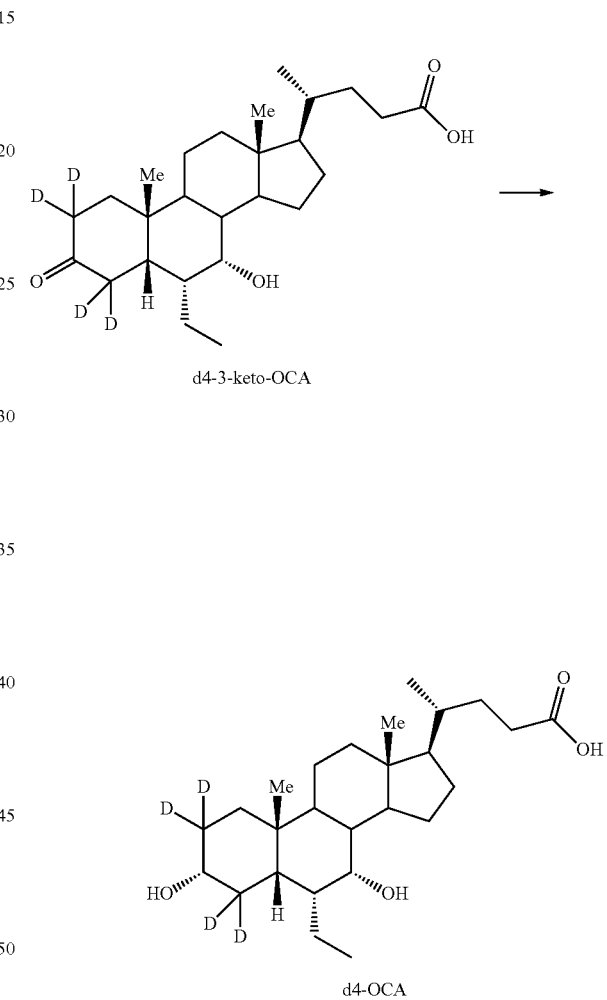

d4-3-keto-OCA d4-OCA

3-Keto-OCA (5 g, 12.0 mmol), prepared as described in Example 1, was dissolved in 40 mL of D₂O and NaOD (40% in D₂O, 3.5 mL) was added. The mixture was stirred at 90° C. for 4 hours. NaBH₄ (0.67 g, 17.7 mmol) was added portionwise and stirring continued for 2 hours at 90° C. The mixture was cooled to room temperature and quenched with aqueous citric acid. The product was extracted with EtOAc (2×). The combined organic layers were washed with brine, dried over Na₂SO₄ and concentrated. The material was taken up in 100 mL of water and 1.0 g of NaOH. The solution was slowly acidified with 10% HCl (aq) until pH 2. The precipitate was collected and washed with water and dried in vacuo.

Example 6: Deuterated Glycine Conjugate of (d₅)-OCA, d₅-OCA-O(d₂)Gly

Example 7: Deuterated Taurine Conjugate of (d₅)-OCA, d₅-OCA-O(d₄)Tau

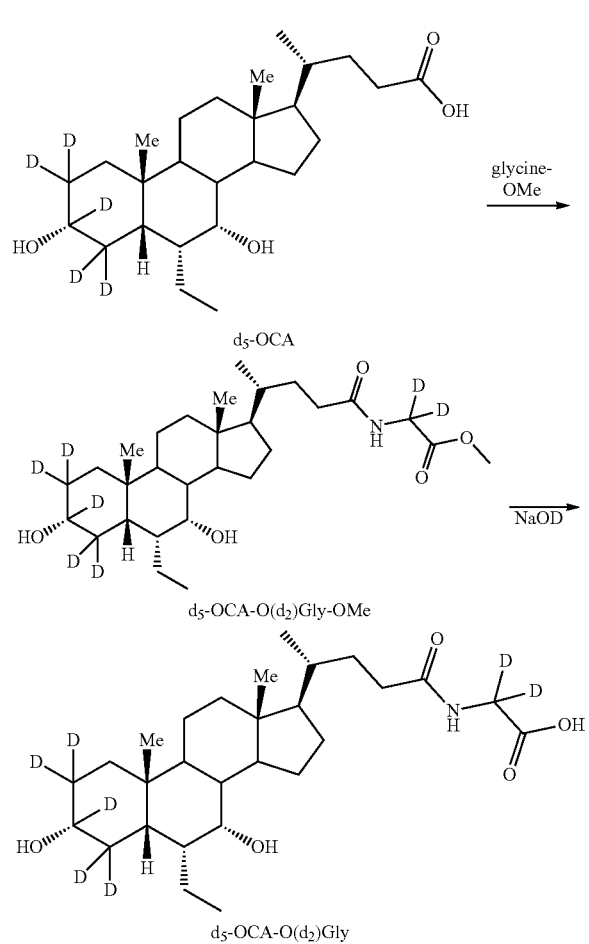

Figure 5:
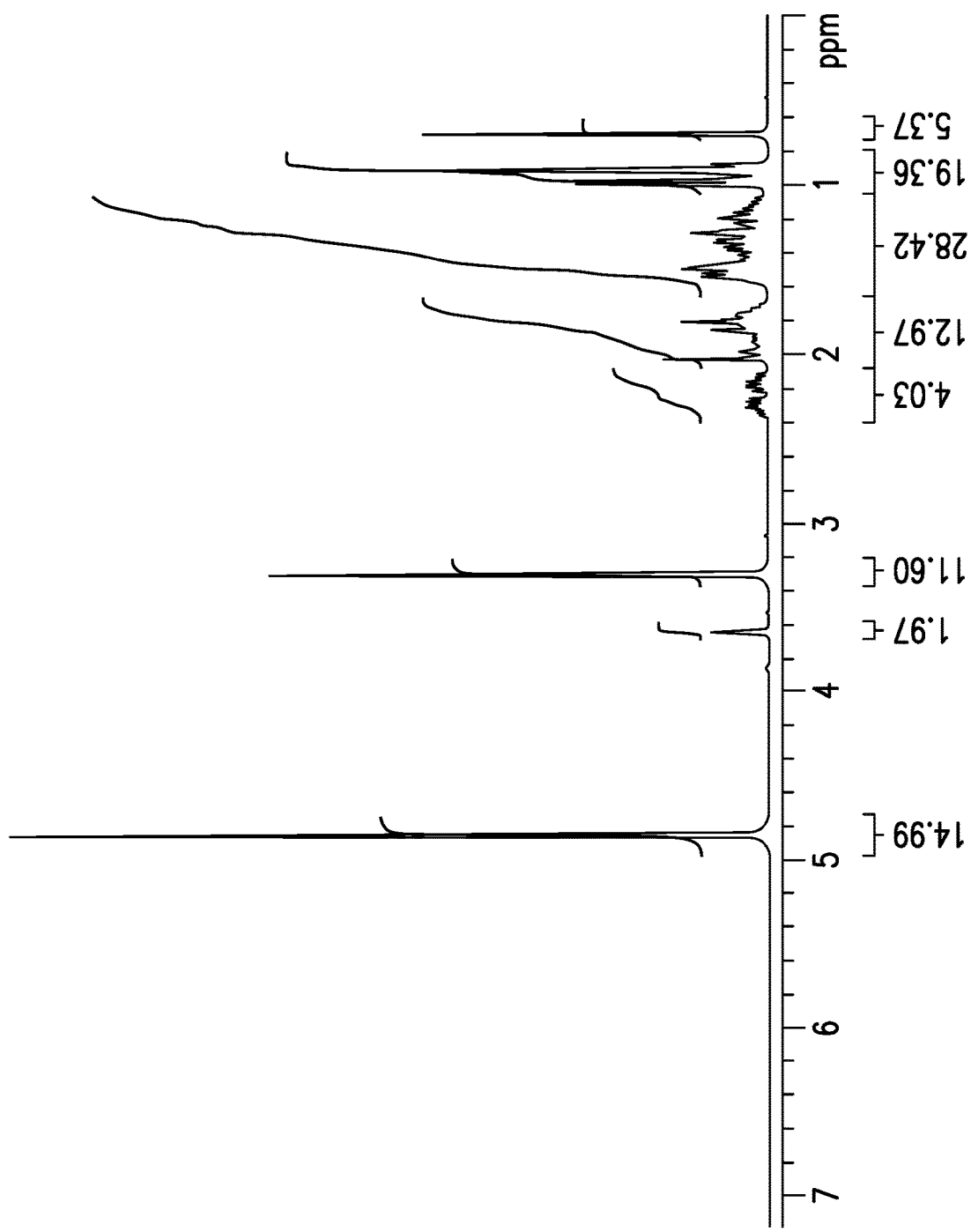
FIG. 5 shows the $^1$H NMR spectrum obtained from deuterated glycine conjugate of d$_5$-OCA, d$_5$-OCA-O(d$_2$)Gly.
Figure 6:
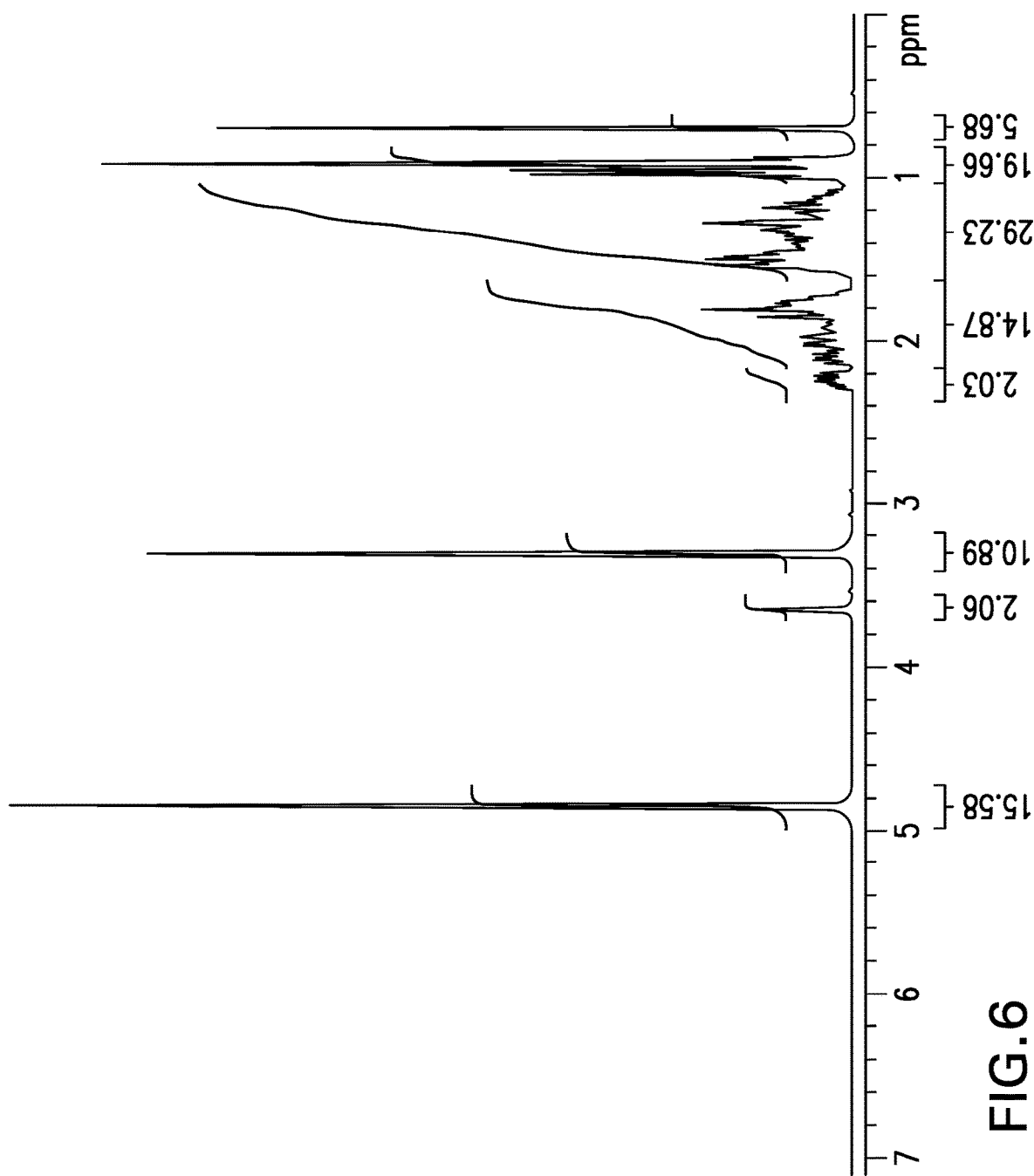
FIG. 6 shows the $^1$H NMR spectrum obtained from deuterated taurine conjugate of d$_5$-OCA, d$_5$-OCA-O(d$_4$)Tau.

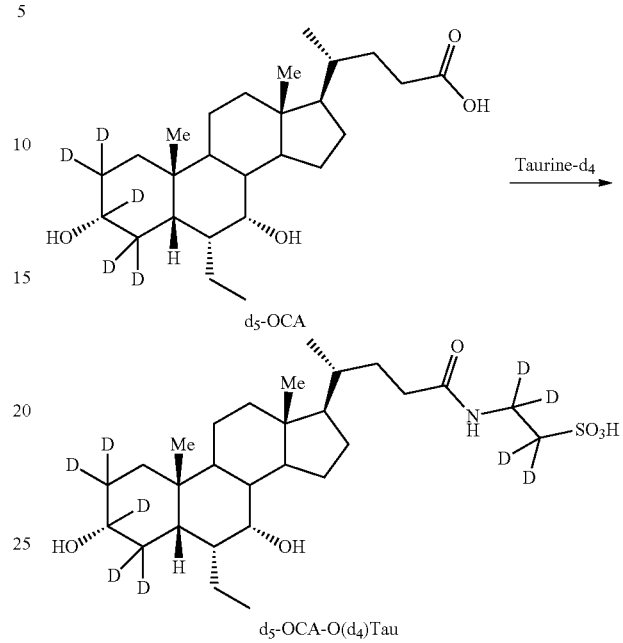

d₅-OCA (2.0 g, 4.7 mmol) was dissolved in 75 mL of DMF and triethylamine (4.7 g, 47 mmol) was added and the mixture was stirred for 5 min. 4-(4,6-Dimethoxy-1,3,5-triazin-2-yl)-4-methylmorpholinium chloride (3.9 g, 14.1 mmol) was added and the mixture was stirred for 5 min. d₂-Gly-OMe.HCl (1.77 g, 14.1 mmol) was added and stirring continued overnight. The mixture was poured into water and extracted with EtOAc (2×). The combined organic layers were washed with brine, dried over Na₂SO₄ and concentrated. The crude material was purified by means of column chromatography (silica; DCM/MeOH 3-7%) affording d₅-OCA-O(d₂)Gly-OMe as a white foam (1.6 g, 68%).

d₅-OCA-O(d₂)Gly-OMe (1.6 g, 3.2 mmol) was dissolved in 20 mL of CH₃OD and NaOD (40% in D₂O, 1 mL) was added. The mixture was stirred for 1 hour and quenched with citric acid (5 g in 100 mL of water). The product was extracted with EtOAc (2×). The combined organic layers were washed with brine, dried over Na₂SO₄ and concentrated. The material was taken up in water with 2 eqv of NaOH. The solution was acidified to pH 1 with 1N HCl and the precipitate was collected and dried in vacuo affording d5-OCA-O(d2)Gly as white solid (1.0 g, 64%). ¹H NMR (300 MHz, CD₃OD) confirmed the identity of this compound (FIG. 5).

d₅-OCA (1.65 g, 3.87 mmol), d₄-Taurine (0.50 g, 3.87 mmol), DIPEA (1.0 g, 7.74 mmol) and EEDQ (0.96 g, 3.87 mmol) were dissolved in 25 mL of DMF and stirred at 90° C. for 2.5 hours. The mixture was cooled to room temperature and 5 mL of NaOH was added. The mixture was concentrated and stripped with toluene twice. The residue was dissolved in water (40 mL) and washed with ethyl acetate (3×). The aqueous layer was acidified with 6N HCl to pH 1 and washed with diethyl ether (3×) and ethyl acetate (3×). The aqueous layer was partially concentrated till some product oils out. The mixture was allowed to stand for a while and the water was decanted from the oily product. The oily product was concentrated and stripped with CH₃CN/MeOH twice. The off-white solid was purified by RP-ISCO (RP=reversed phase). The appropriate fractions were collected, concentrated and stripped with CH₃CN/MeOH twice affording d₅-OCA-O(d)Tau as white solid (1.3 g, 62%). ¹H NMR (300 MHz, CD₃OD) confirmed the identity of this compound (FIG. 6).

Example 8: OCA-3-O-Glucuronide

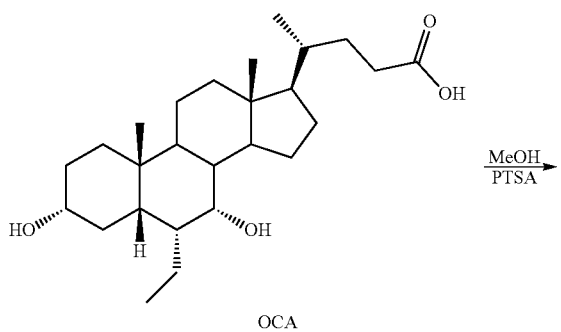

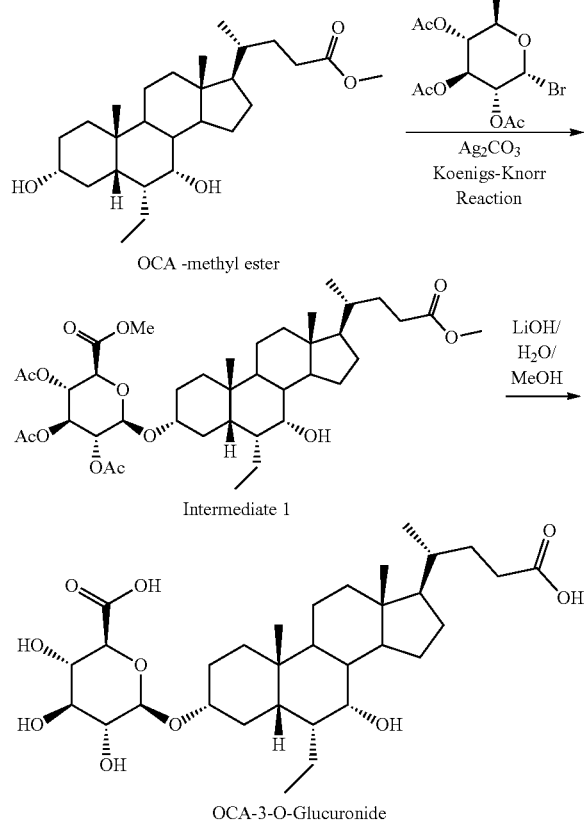

OCA-methyl ester

Intermediate 1

OCA-3-O-Glucuronide

Step 1: OCA Methyl Ester

A solution of OCA (212.7 mg, 0.51 mmol), anhydrous methanol (6 mL), and para-toluenesulfonic acid (19.6 mg, 0.11 mmol) was sonicated for 2 hours at which time the reaction was complete by TLC. The solvent was evaporated via gentle nitrogen and the residue was dried in vacuuo (at room temperature) for 30 minutes. Chloroform (8 mL) and saturated aqueous sodium bicarbonate (5.2 mL) were charged and the aqueous layer was separated. The organic layer was sequentially washed with water (5 mL) and brine (5 mL). The organic layer was dried over sodium sulfate and filtered. The filtrate was concentrated via rotary evaporation to afford OCA-methyl ester (227 mg, 100% yield) as a clear oil. $^1$H NMR confirmed the identity of this compound.

Step 2: Synthesis of Intermediate 1

A solution of OCA-methyl ester (227 mg, 0.52 mmol) in anhydrous toluene (8 mL) was treated with silver carbonate (672.7 mg, 2.4 mmol) and acetobromo-α-D-glucuronic acid methyl ester (1034.9 mg, 2.6 mmol). The resulting solution was stirred at room temperature for four days at which time the reaction was complete by HPLC. The reaction mixture was filtered through a 1.0 μm PTFE syringe filter and the syringe filter was washed with ethyl acetate (2×5 mL). The pooled filtrates were evaporated via rotary evaporation and the residue was purified via silica gel flash column chromatography to afford crude Intermediate 1 (183 mg). The structure of Intermediate 1 was confirmed by $^1$H NMR, $^{13}$C NMR and HMBC NMR. Glucuronide is in 3 position as demonstrated by HMBC coupling between C3 proton (3.45 ppm) and the 1' anomeric carbon (99 ppm).

Step 3: Synthesis of OCA-3-O-Glucuronide

Figure 7:
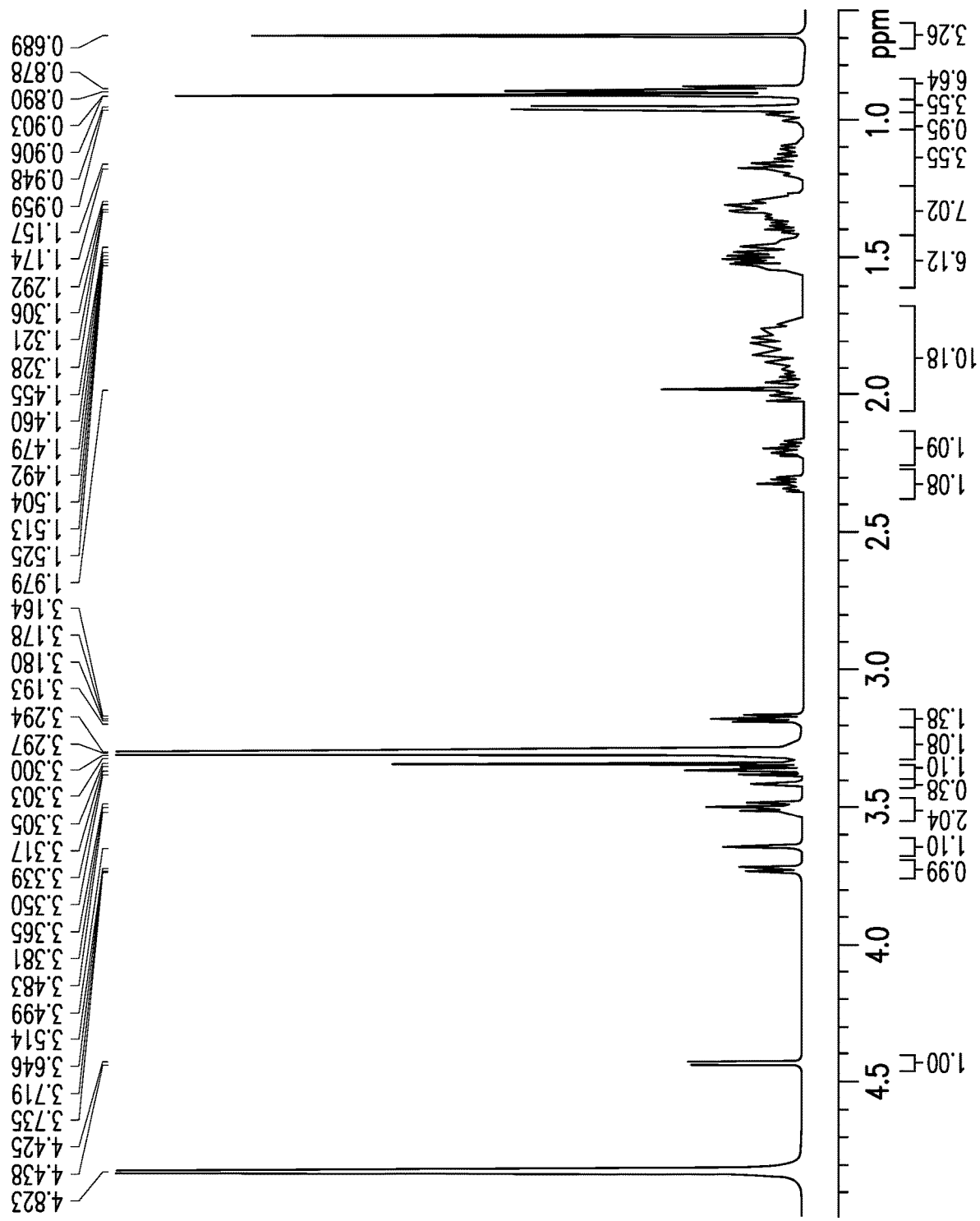
FIG. 7 shows the $^1$H NMR spectrum obtained from OCA-3-O-Glucuronide.

A solution of intermediate 1 (150 mg, 0.2 mmol) in methanol (12 mL) was treated with 6.5 mL of aqueous 2M LiOH (13 mmol). The resulting solution was stirred for 2 hours at room temperature at which time the reaction was complete by TLC. The solvents were evaporated via slow nitrogen stream. Water (2 mL) was added and concentrated hydrochloric acid was added dropwise until the pH of the solution was 4-5 (as measured by narrow range pH paper). The solvents were evaporated via rotary evaporation and the resulting residue was dried in vacuuo overnight. A slurry of crude product in 3 mL of 0.1% (v/v %, acetic acid in water) was applied to a pre-washed (washed with 3 column volumes of methanol followed by 5 column volumes of 0.1% acetic acid in water) 10 gram C18 Sep-Pak® cartridge. The pooled product-containing fractions (as determined by TLC) were evaporated via rotary evaporation and dried in vacuuo to afford OCA-3-O-Glucuronide (64 mg, 0.1 mmol, 50% yield from Intermediate 1, 10% overall yield from OCA). OCA-3-O-Glucuronide was analyzed by $^1$H NMR (Table 1 and FIG. 7).

TABLE 1

$^1$H NMR of OCA-3-O-Glucuronide 600 MHz NMR

| Metabolite | Chemical groups | Chemical Shift ppm |
|---|---|---|
| Solvent, MHz | C-18 $H_3$ | s, 0.69 |
| INT-747-3-glucuronide | C-19 $H_3$, C-26 $H_3$ | m, 0.89 |
| $CH_3OD$, 600 | C-21 $H_3$ | d, 0.95 |
| | C-23 $H_2$ | m, 2.19 |
| | C-23 $H_2$ | m, 2.34 |
| | C-3 $H_2$ | m, 3.18 |
| | C-2', C-3', C-4', $H_3$ | m, 3.51; t, 3.37 |
| | C-7 $H_2$ | t, 3.65 |
| | C-5' $H_2$ | d, 3.73 |
| | C-1' $H_2$ | d, 4.43 ($J_{H, H}$ = 7.8 Hz) |

Example 9: [$^3$H]OCA-24-Glucuronide

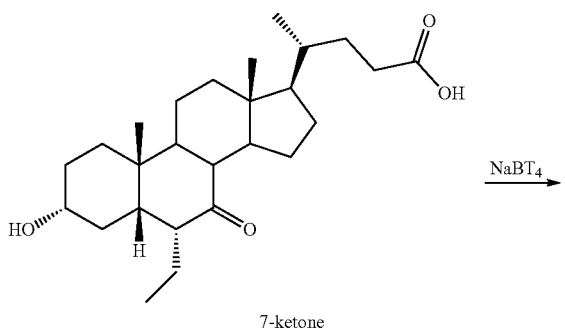

7-ketone

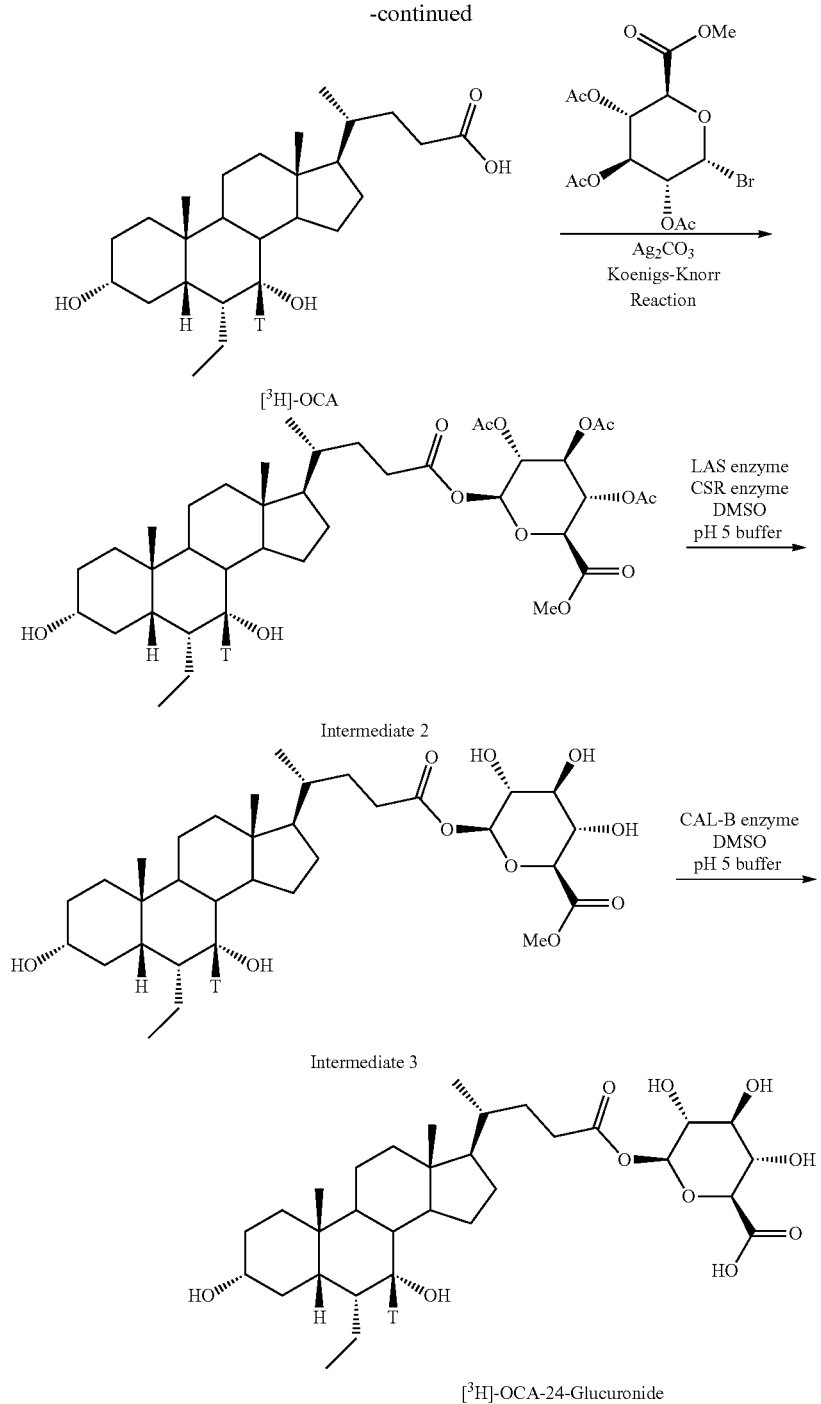

Step 1: Synthesis of [³H]OCA

A solution of 7-ketone (217.6 mg, 0.52 mmol) in water (2.4 mL) and 50% aqueous NaOH (0.21 mL) was heated to 90° C. to afford solution A. The resulting solution was transferred into a dry reaction tube containing NaBT₄ (7.4 mg, 0.19 mmol, 49 mCi). The tube was sealed and heated at 90° C. for 1 hour. Additional unlabeled NaBH₄ (75 mg, 2.0 mmol) was added and the heating was continued at 90° C. for 3 additional hours. The resulting mixture was cooled to room temperature and diluted with a mixture of n-butyl-acetate (3 mL) and a solution of citric acid (1.329 g, 6.92 mmol) in water (1.7 mL). The layers were separated and the aqueous phase was discarded. The reaction was repeated using 240.6 mg 7-ketone and 5.7 mg of NaBT₄.

The pooled organic layers from the two reactions were evaporated and purified via silica gel flash column chromatography eluting with 1/2 (v/v, hexanes/ethyl acetate) to afford [³H]-OCA (198 mg, 0.47 mmol, 4.8 mCi, 6% yield from NaBT₄, 43% yield from 7-ketone). An HPLC/UV chromatogram of OCA standard and a radio-HPLC chromatogram of [³H]-OCA were performed.

Step 2: Synthesis of Intermediate 2

A solution of [$^3$H]-OCA (198 mg, 0.47 mmol, 4.8 mCi) and unlabeled OCA (200 mg, 0.48 mmol) in anhydrous DMF (40 mL) was treated with silver carbonate (754.4 mg, 2.7 mmol) and acetobromo-α-D-glucuronic acid methyl ester (485.4 mg, 1.2 mmol). The resulting solution was stirred at room temperature for four days at which time the composition was 21% product, 71% [$^3$H]-OCA, and 8% side product (by radio-HPLC). The reaction mixture was filtered through a 0.45 μm PTFE syringe filter and the syringe filter was washed with ethyl acetate (2×10 mL). The pooled filtrates were evaporated via rotary evaporation and the residue was purified via silica gel flash column chromatography. The pooled product-containing fractions were evaporated via rotary evaporation to afford crude intermediate 2 (168 mg, 0.23 mmol, 0.87 mCi@ 80% purity with 20% [$^3$H]-OCA by radio-HPLC) which was used in the next step without further purification. The structure of non-labeled intermediate 2 was confirmed by $^1$H NMR, $^{13}$C NMR and HMBC NMR.

Step 3: Synthesis of Intermediate 3

A solution of Intermediate 2 (168 mg) in DMSO (23 mL) and 93 mL of 25 mM citric acid buffer (pH=5) was treated with LAS enzyme (Supplier=Aldrich, 1.245 g) and CSR enzyme (Supplier=Wako chemical, 1.209 g). The resulting solution was heated at 40° C. for 2 hours at which time the reaction was complete by radio-HPLC. The resulting mixture was cooled to room temperature and applied to a pre-washed (washed with 3 column volumes of methanol followed by 5 column volumes of 0.01% acetic acid in water) 10 gram C18 Sep-Pak cartridge. The cartridge was sequentially washed with (3 column volumes each) of 0.01% formic acid in water, 80/20, 50/50, 40/60, 30/70, 20/80, and 10/90 (v/v %, 0.01% formic acid in water/acetonitrile) followed by neat acetonitrile. The pooled product-containing fractions (as determined by radio-HPLC) were evaporated via rotary evaporation and dried in vacuuo to afford intermediate 3 (72.3 mg, 0.12 mmol).

Step 4: Synthesis of [$^3$H]-OCA-24-Glucuronide

Figure 8:
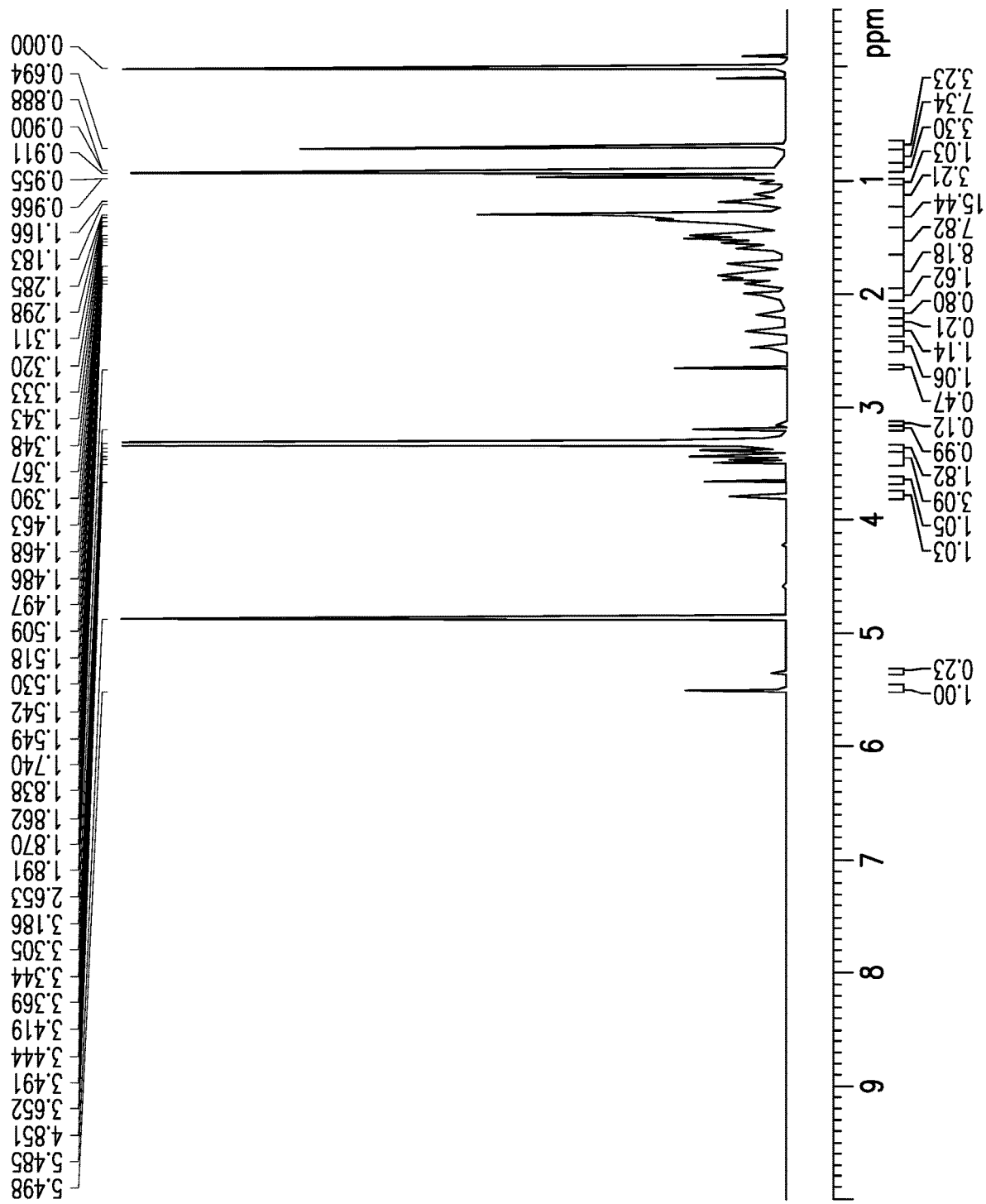
FIG. 8 shows the $^1$H NMR spectrum obtained from [$^3$H]-OCA-24-Glucuronide.
Figure 9:
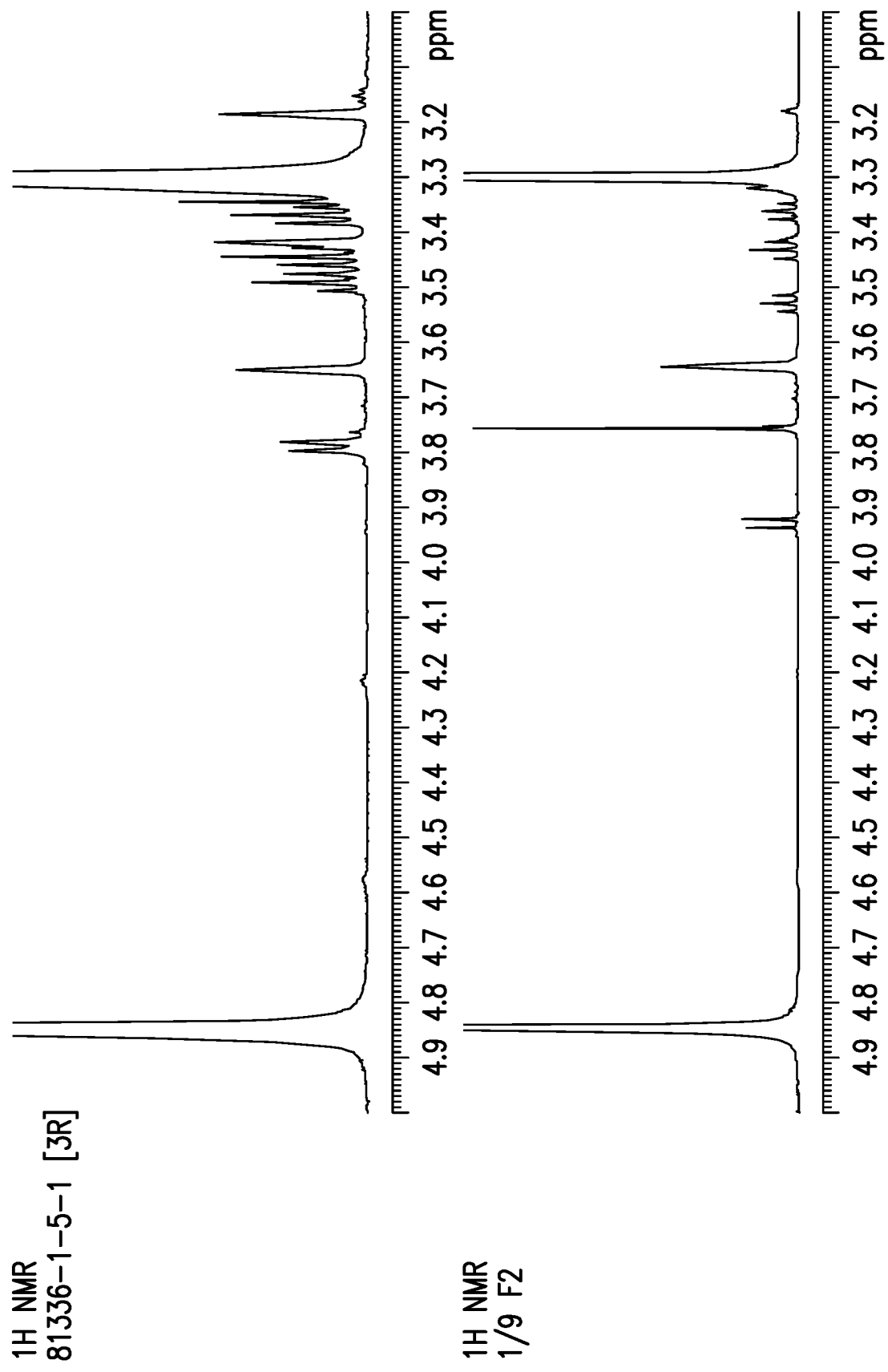
FIG. 9 shows comparison plot for $^1$H NMR spectra of OCA-24-Glucuronide methyl ester and [$^3$H]OCA-24-Glucuronide (expansion of 3.0-5.0 ppm region).

A solution of intermediate 3 (72.3 mg, 0.12 mmol) in DMSO (6.4 mL) and 70 mL of 25 mM citric acid buffer (pH=5) was treated with Cal-B enzyme (Supplier Aldrich, 42.3 mg). The resulting solution was heated at 40° C. for 3 hours at which time the reaction was complete by radio-HPLC. The resulting mixture was cooled to room temperature and applied to a pre-washed (washed with 3× column volumes of methanol followed by 5 column volumes of 0.01% acetic acid in water) 10 gram C18 Sep-Pak cartridge. The cartridge was sequentially washed with (3 column volumes each) of 0.01% formic acid in water, 90/10, 80/20, 70/30, 60/40, 50/50, and 40/60 (v/v %, 0.01% formic acid in water/acetonitrile). The pooled product-containing fractions (as determined by radio-HPLC) were evaporated via rotary evaporation and dried in vacuuo to afford [$^3$H]-OCA-24-Glucuronide (39 mg, 0.065 mmol, 14% overall yield from [$^3$H]-OCA. Structure of [$^3$H]-OCA-24-Glucuronide was confirmed by $^1$H NMR (Table 2 and FIG. 8) and HMBC NMR. Comparison plot for $^1$H NMR spectra of OCA-24-Glucuronide methyl ester and [$^3$H]OCA-24-Glucuronide (expansion of 3.0-5.0 ppm region) (FIG. 9) shows that the methyl ester protons (singlet at 3.78 ppm in OCA-24-Glucuronide methyl ester) are not present in [$^3$H]OCA-24-Glucuronide.

TABLE 2

$^1$H NMR of [$^3$H]-OCA-24-Glucuronide 600 MHz NMR

| Metabolite | Chemical groups | Chemical Shift ppm |
| --- | --- | --- |
| Solvent, MHz [$^3$H]-INT-747- 24-Glucuronide CH$_3$OD, 600 | C-18 H$_3$ | s, 0.69 |
| | C-19 H$_3$, C-26 H$_3$ | m, 0.91 |
| | C-21 H$_3$ | d, 0.95 |
| | C-23 H$_2$ | m, 2.35 |
| | C-23 H$_2$ | m, 2.45 |
| | C-3 H$_2$ | s, 3.19 |
| | C-2', C-3', C-4', H$_3$ | m, 3.46 |
| | C-7 H$_2$ | t, 3.65 |
| | C-5' H$_2$ | d, 3.79 |
| | C-1' H$_2$ | d, 5.49 ($J_{H, H}$ = 7.8 Hz) |

Example 10. [$^{14}$C-24]OCA

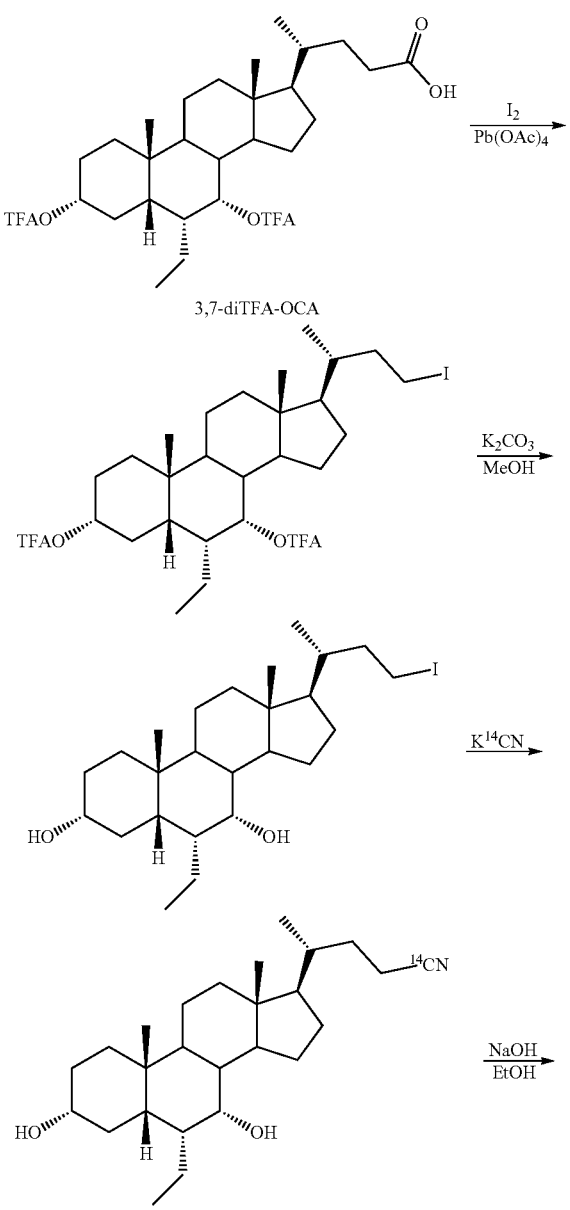

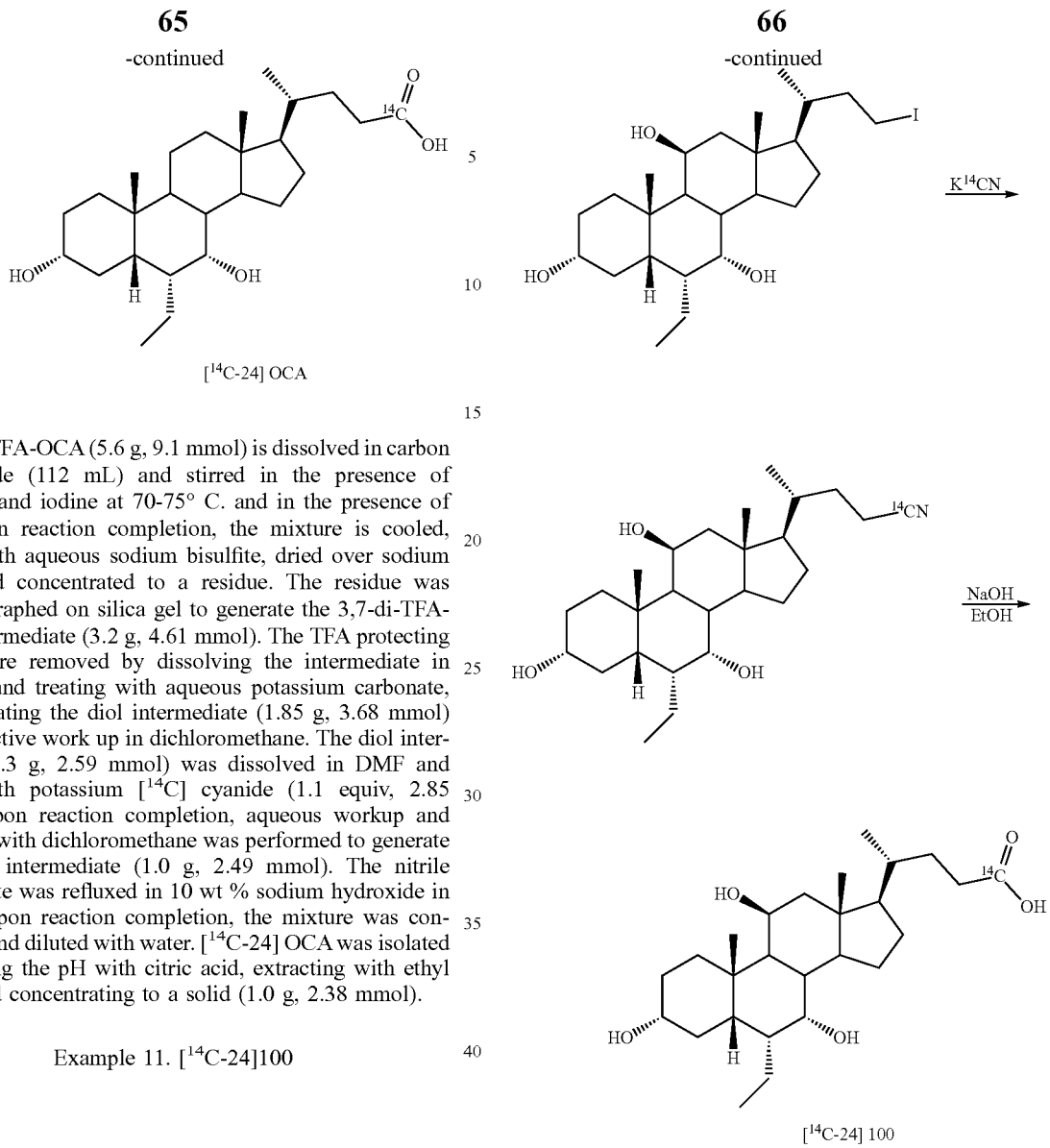

3,7-Di-TFA-OCA (5.6 g, 9.1 mmol) is dissolved in carbon tetrachloride (112 mL) and stirred in the presence of Pb(OAc)$_4$ and iodine at 70-75° C. and in the presence of light. Upon reaction completion, the mixture is cooled, washed with aqueous sodium bisulfite, dried over sodium sulfate and concentrated to a residue. The residue was chromatographed on silica gel to generate the 3,7-di-TFA-iodide intermediate (3.2 g, 4.61 mmol). The TFA protecting groups were removed by dissolving the intermediate in methanol and treating with aqueous potassium carbonate, thus generating the diol intermediate (1.85 g, 3.68 mmol) after extractive work up in dichloromethane. The diol intermediate (1.3 g, 2.59 mmol) was dissolved in DMF and treated with potassium [$^{14}$C] cyanide (1.1 equiv, 2.85 mmol). Upon reaction completion, aqueous workup and extraction with dichloromethane was performed to generate the nitrile intermediate (1.0 g, 2.49 mmol). The nitrile intermediate was refluxed in 10 wt % sodium hydroxide in ethanol. Upon reaction completion, the mixture was concentrated and diluted with water. [$^{14}$C-24] OCA was isolated by adjusting the pH with citric acid, extracting with ethyl acetate and concentrating to a solid (1.0 g, 2.38 mmol).

Example 11. [$^{14}$C-24]100

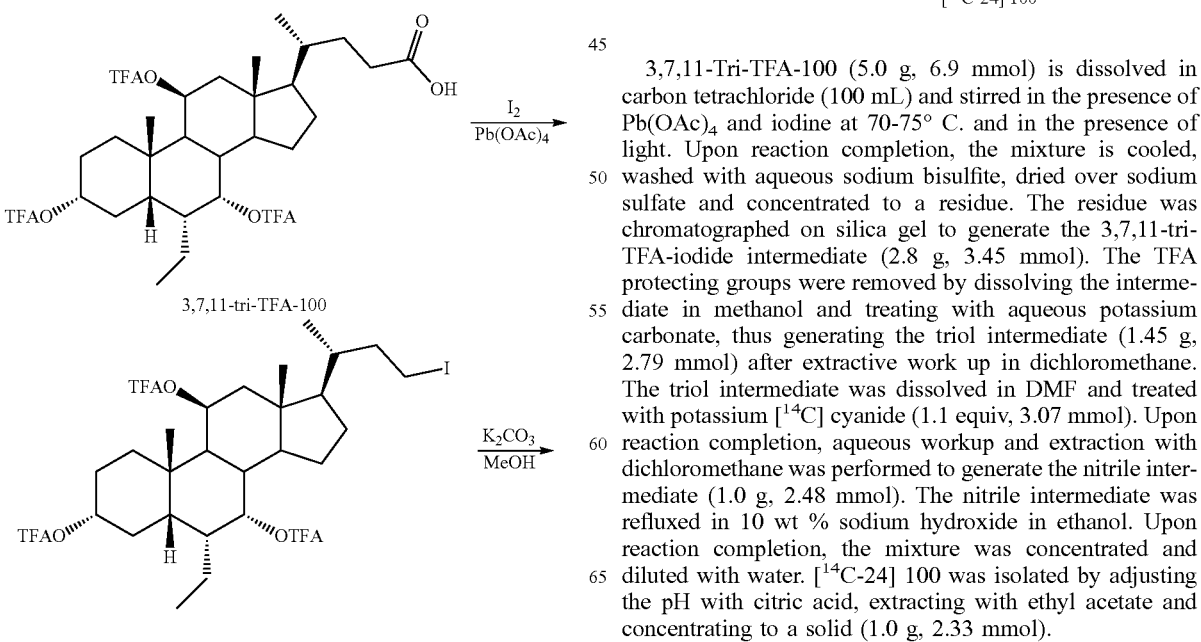

3,7,11-Tri-TFA-100 (5.0 g, 6.9 mmol) is dissolved in carbon tetrachloride (100 mL) and stirred in the presence of Pb(OAc)$_4$ and iodine at 70-75° C. and in the presence of light. Upon reaction completion, the mixture is cooled, washed with aqueous sodium bisulfite, dried over sodium sulfate and concentrated to a residue. The residue was chromatographed on silica gel to generate the 3,7,11-tri-TFA-iodide intermediate (2.8 g, 3.45 mmol). The TFA protecting groups were removed by dissolving the intermediate in methanol and treating with aqueous potassium carbonate, thus generating the triol intermediate (1.45 g, 2.79 mmol) after extractive work up in dichloromethane. The triol intermediate was dissolved in DMF and treated with potassium [$^{14}$C] cyanide (1.1 equiv, 3.07 mmol). Upon reaction completion, aqueous workup and extraction with dichloromethane was performed to generate the nitrile intermediate (1.0 g, 2.48 mmol). The nitrile intermediate was refluxed in 10 wt % sodium hydroxide in ethanol. Upon reaction completion, the mixture was concentrated and diluted with water. [$^{14}$C-24] 100 was isolated by adjusting the pH with citric acid, extracting with ethyl acetate and concentrating to a solid (1.0 g, 2.33 mmol).

Example 12: [$^{14}$C]OCA at High Specific Activity (Synthesis was Carried Out on a 105 mCi Scale)

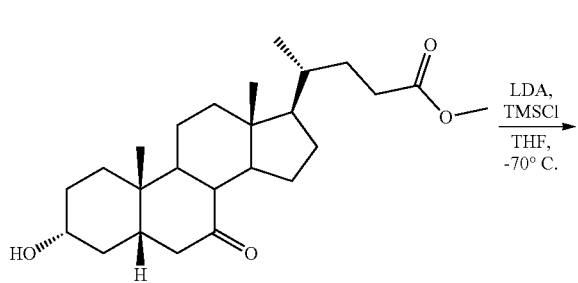

C1

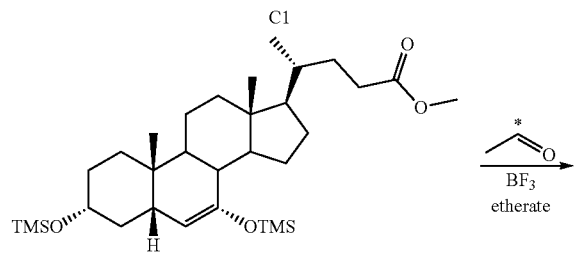

C2

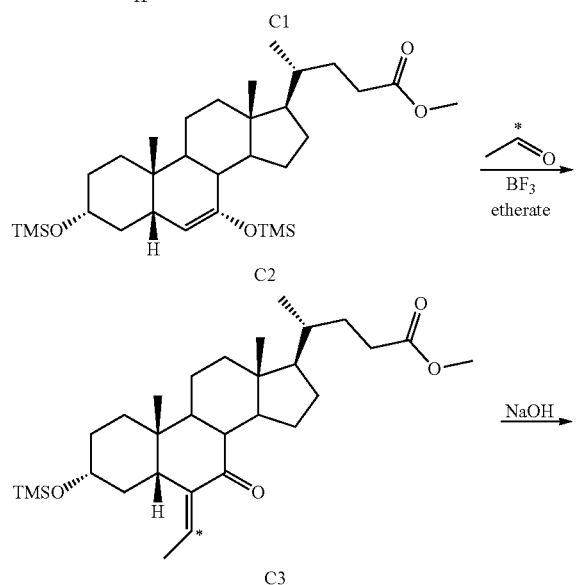

C3

C4

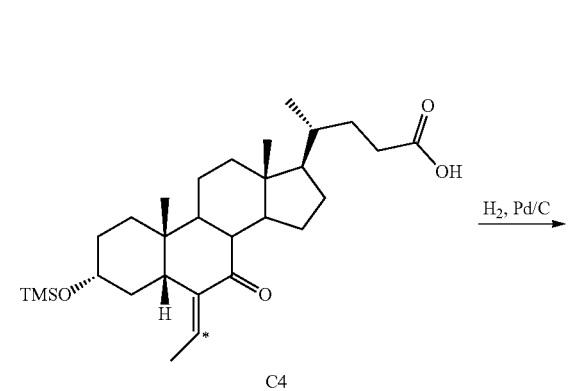

C5

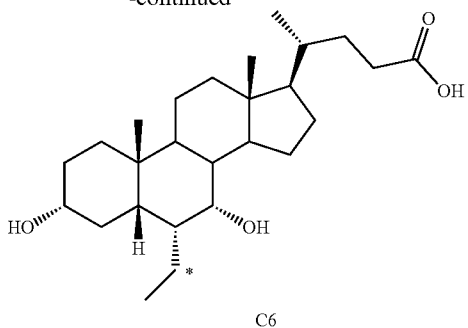

C6

* indicates $^{14}$C

Step 1: Preparation of Compound C2

Diisopropylamine and tetrahydrofuran (THF) are stirred at approximately −20° C. under argon. N-butyllithium is added slowly and the mixture stirred at approximately −20° C. before cooling to approximately −70° C. Chlorotrimethylsilane is added and the mixture stirred. Compound C1 dissolved in THF is added slowly and stirred at approximately −70° C. and then warmed to approximately −50° C. and further stirred. Aqueous sodium hydrogen carbonate is added and the mixture warmed to room temperature. The aqueous layer is separated and washed with ethyl acetate. The organic layers are combined and washed with aqueous sodium hydrogen carbonate, water and brine and dried over sodium sulphate. The solution is filtered, washed with toluene, rotary evaporated and desiccated under vacuum to yield compound C2 as a yellow oil.

Step 2: Preparation of Compound [$^{14}$C]C3

[1-$^{14}$C] Acetaldehyde, compound C2 and dichloromethane are stirred at approximately −70° C. under nitrogen. Boron trifluoride etherate is added slowly and the reaction stirred at approximately −70° C. and then at room temperature overnight. Nitrogen is bubbled through the solution. The solution is then cooled in an ice bath and aqueous sodium hydrogen carbonate is added. The aqueous layer is separated and washed with dichloromethane. The organic layers are combined and dried over sodium sulphate. The solution is filtered, rotary evaporated and the residue is purified by flash chromatography (silica, hexane:ethyl acetate). The solution is rotary evaporated, methanol added and rotary evaporated to yield [$^{14}$C] C3 as a gum.

Step 3: Preparation of Compound [$^{14}$C]C4

Compound [$^{14}$C]C3, methanol and sodium hydroxide are stirred at approximately 45° C. The reaction is cooled, partially rotary evaporated to remove methanol, and water is added. The solution is cooled in an ice bath and acidified with aqueous phosphoric acid. The mixture is extracted with dichloromethane. The organic layers are combined and dried over sodium sulphate. The solution is filtered, rotary evaporated and desiccated under vacuum to yield compound [$^{14}$C]C4 as a solid.

Step 4: Preparation [$^{14}$C]OCA Ketone C5

[$^{14}$C]C4 is dissolved in sodium hydroxide, 5% palladium on carbon is added, and hydrogenated at room temperature and then at approximately 115° C. The reaction is cooled to room temperature, filtered and cooled in ice. The solution is acidified with concentrated hydrochloric acid and extracted with dichloromethane. The dichloromethane solution is dried over sodium sulphate, filtered and rotary evaporated. The residue is dissolved in ethanol:acetonitrile:water to give a solution containing [$^{14}$C]OCA ketone C5. This solution was purified by HPLC (C18 column, aqueous hydrochloric acid:acetonitrile). The solution is rotary evaporated, water is added and the solution is rotary evaporated again. The solid is desiccated under vacuum to yield [$^{14}$C]OCA ketone C5.

The quality of the radiolabelled precursor [$^{14}$C]OCA ketone C5 is considered to be critical to the quality of [$^{14}$C]OCA C6 drug substance and is therefore controlled according to the results given in Table 3.

TABLE 3

Critical intermediate for synthesis of [$^{14}$C]OCA C6

| Component | Supplier | Analysis | Results | |
|---|---|---|---|---|
| Radiolabelled designated starting material [$^{14}$C]OCA Ketone | Quotient Bioresearch (Radiochemicals) Ltd | Specific activity | 25 mCi mmol$^{-1}$ | |
| | | Purity by HPLC (UV and RCP) | UV | 99.5% |
| | | | RCP | 99.3% |
| | | Co-chromatography with reference (HPLC) | Co-chromatographs Conforms | |
| | | NMR spectrometry | Conforms | |
| | | Mass spectrometry | | |

Step 5: Preparation of [$^{14}$C]OCA C6

[$^{14}$C]OCA ketone C5 is suspended in 2M sodium hydroxide and heated to approximately 80° C. A solution of sodium borohydride in water is added and the resulting reaction mixture is heated at approximately 100° C. The progress of the reaction is monitored by TLC. Water and dichloromethane are added to the reaction mixture. To quench the reaction ortho-phosphoric acid is slowly added whilst stirring until no effervescence occurs and no solid remains. The aqueous layer is separated and extracted with dichloromethane. The organic layers are combined, dried over sodium sulphate, filtered and evaporated to yield crude [$^{14}$C]OCA C6 as a white solid. Crude [$^{14}$C]OCA C6 is dissolved in the minimum volume of ethyl acetate and diluted with an equal volume of heptane. The solution is loaded onto a silica column and eluted with heptane:ethyl acetate (1% acetic acid in ethyl acetate). The fractions are collected and analysed by TLC. Fractions containing [$^{14}$C]OCA C6 are combined, washed with water, dried with sodium sulphate and concentrated under reduced pressure to remove solvent.

The material from the flash column is dissolved in dichloromethane and stirred for at least 16 hours with QuadraPure Tu palladium scavenger. The scavenger is removed by filtration and filtrate concentrated under reduced pressure to remove solvent. The material from the filtrate is further purified using preparative HPLC with a C18 column eluting with 5 mM sodium phosphate:acetonitrile:methanol. The fractions containing [$^{14}$C]OCA C6 are combined and the organic solvent is removed under reduced pressure. The remaining aqueous solution is extracted with ethyl acetate. The ethyl acetate extracts are combined, washed with brine and the solvent is removed portion-wise under reduced pressure.

Purified [$^{14}$C]OCA C6 is dissolved in 0.2 M sodium hydroxide under stirring. The solution is filtered, washed with water and stored at room temperature. Separately 0.2 M hydrochloric acid is stirred and filtered. The solution of [$^{14}$C]OCA C6 in sodium hydroxide is added to the hydrochloric acid drop wise. The resulting suspension is stirred and the solid collected by centrifugation. The solid is washed with water, centrifuged and the solid is then transferred to a sinter funnel and dried under suction. The resulting dried product is [$^{14}$C]OCA C6 at high specific activity.

[$^{14}$C]OCA was characterised by mass spectrometry, HPLC and $^1$H NMR. The data show that the end product of the technical synthesis, [$^{14}$C]OCA drug substance was 99.6% chemically pure and 98.0% radiochemically pure, which is considered to be of suitable quality for clinical use. The batch also met the specific activity requirements (result obtained 299.4 kBq mg-1).

Figure 10:
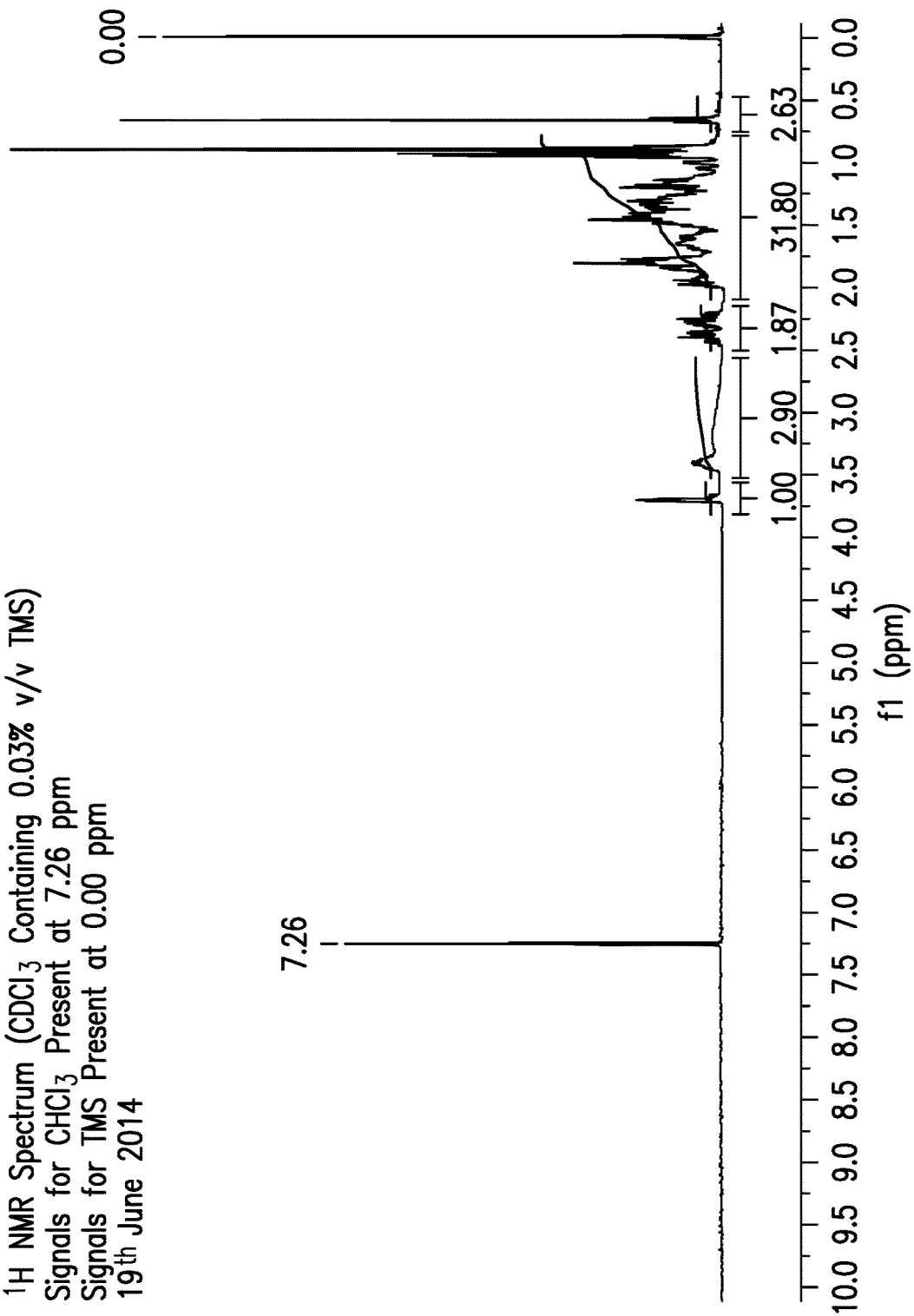
FIG. 10 shows the $^1$H NMR spectrum obtained from [$^{14}$C]OCA.
Figure 11:
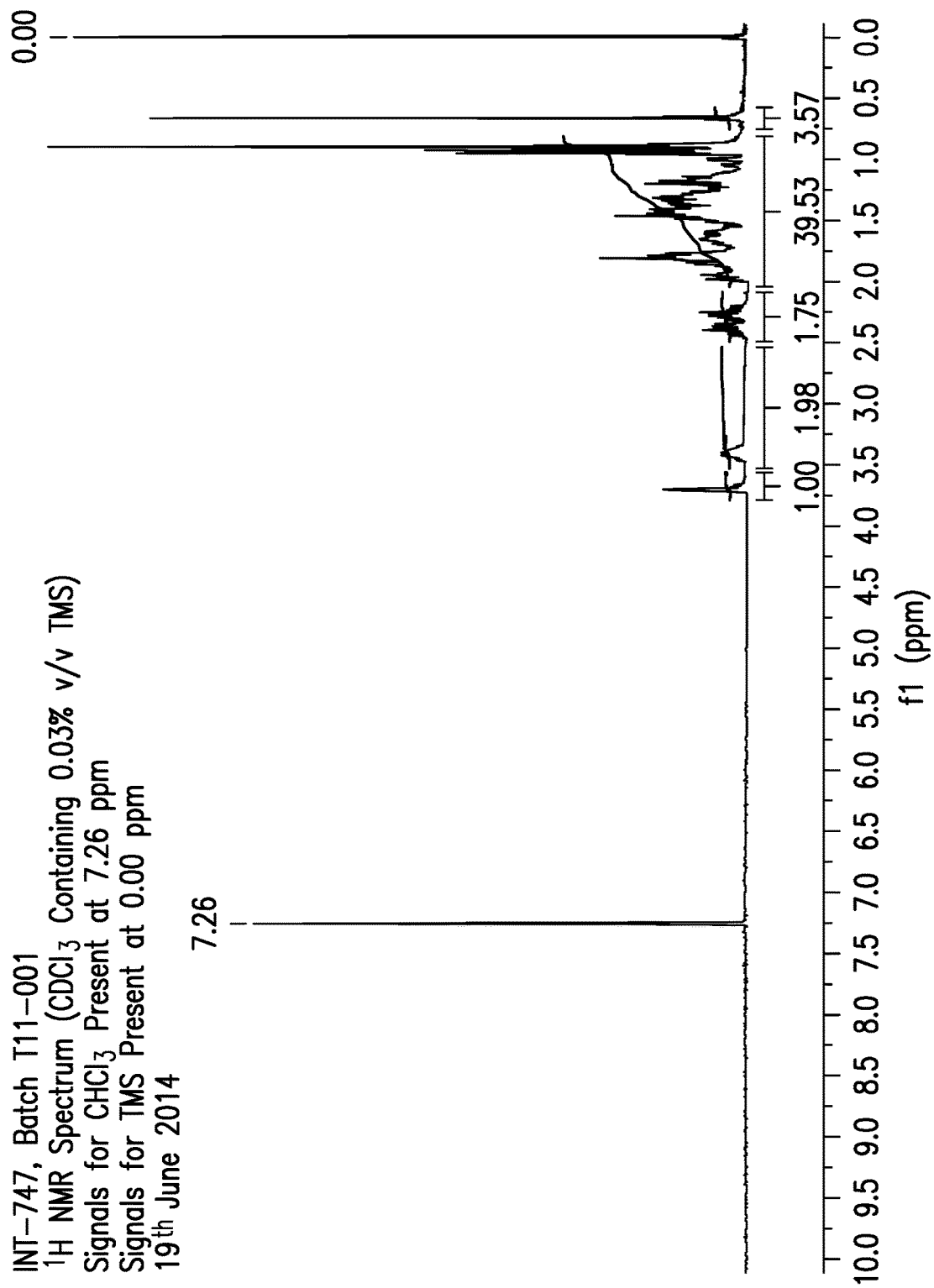
FIG. 11 shows the $^1$H NMR spectrum obtained from OCA Reference Material.

The $^1$H NMR spectrum obtained from [$^{14}$C]OCA (FIG. 10) was compared with the $^1$H NMR spectrum obtained from OCA Reference Material (FIG. 11).

Mass Spectrum for [$^{14}$C]OCA (MeOH: 0.5% ammonia, 9:1, 10 µg/mL, 20 µL/min inf, ES−, cone=85 V, Temp=80° C.):

Chemical formula (unlabelled): $C_{26}H_{44}O_4$
Exact Mass: 420.32

| m/z | Intensity | Assignment | |
|---|---|---|---|
| 419.3 | 1.26 × 10$^6$ | [M − H]$^−$ | unlabelled |
| 420.3 | 3.67 × 10$^7$ | [M − H]$^−$ | 1 × C-13 |
| 421.3 | 1.35 × 10$^7$ | [M − H]$^−$ | 1 × C-14 label or 2 × C-13 |
| 451.5 | 1.41 × 10$^7$ | [(M − H)MeOH]$^−$ | unlabelled |
| 452.4 | 4.24 × 10$^6$ | [(M − H)MeOH]$^−$ | 1 × C-13 |
| 453.4 | 1.57 × 10$^8$ | [(M − H)MeOH]$^−$ | 1 × C-14 label or 2 × C-13 |

Mass Spectrum for Reference Standard OCA (MeOH: 0.5% ammonia, 9:1, 10 µg/mL, 20 µL/min inf, ES−, cone=85 V, Temp=80° C.):

| m/z | Intensity | Assignment | |
|---|---|---|---|
| 419.3 | 1.30 × 10$^8$ | [M − H]$^−$ | |
| 420.3 | 5.12 × 10$^7$ | [M − H]$^−$ | 1 × C-13 |
| 421.3 | 8.54 × 10$^8$ | [M − H]$^−$ | 2 × C-13 |
| 451.4 | 1.86 × 10$^7$ | [(M − H)MeOH]$^−$ | 1 × C-13 |
| 452.4 | 5.59 × 10$^8$ | [(M − H)MeOH]$^−$ | 2 × C-13 |

Example 13: Clinical Study

The objectives of this study were to determine the absolute bioavailability of OCA, and evaluate the absorption, distribution, metabolism, and excretion of OCA in healthy male subjects. In addition, the oral pharmacokinetics (PK) of OCA and carbon-14 ([$^{14}$C]-OCA, and intravenous (IV) PK of [$^{14}$C]-OCA were evaluated.

The Simplified Investigational Medicinal Product Dossier (sIMPD) describes the [$^{14}$C]-OCA Solution for Intravenous Administration (20 µg/mL), the [$^{14}$C]-OCA Drug in Capsule and the OCA Tablet. The non-radiolabelled OCA drug substance and drug product (OCA Tablet (25 mg)) were used in this study.

In order to obtain [$^{14}$C]OCA at the specific activity required for clinical use, [$^{14}$C]OCA is synthesised at high specific activity and is then radiodiluted using non-radiolabelled OCA to give the final [$^{14}$C]OCA drug substance at the correct specific activity for use in the proposed clinical trial. The described above synthesis was carried out on a 105 mCi scale. [$^{14}$C]OCA high specific activity component can be combined with the OCA cold component at an approximate ratio of 1:6, [$^{14}$C]OCA to OCA to produce [$^{14}$C]OCA drug substance with the specific activity required for use in the [$^{14}$C]-OCA Solution for intravenous administration (e.g., 20 μg/mL) or oral administration in clinical trial or other study. The material can then further diluted by a factor of 1:2 (overall 1:12) [$^{14}$C]OCA to OCA to produce [$^{14}$C]OCA drug substance with the specific activity required for use in the [$^{14}$C]-OCA Drug in Capsule in clinical trial or other study.

Absolute Bioavailability of OCA

Absolute bioavailability is the percentage of the administered dose that is absorbed into the systemic circulation unchanged. Data in human subjects to date indicate that the PK profile of OCA is consistent with that expected of a bile acid. There is rapid absorption, followed by extensive conjugation (metabolism) to glycine and taurine to form glyco-OCA and tauro-OCA, respectively, which undergo extensive enterohepatic circulation. Plasma concentrations dramatically increase shortly after food intake, consistent with gallbladder emptying into the duodenum. A small percentage the conjugates are subsequently deconjugated to re-form the parent drug (OCA) in the colon. Notably, glyco-OCA and tauro-OCA have been shown to have equipotent pharmacological action to that of the parent drug, thus, their plasma PK profiles are of interest. The total metabolite profile was also investigated in this study.

(a) IV PK as Part of Absolute Bioavailability Assessment

The PK objectives of Part 1 were to determine the absolute bioavailability of OCA, to define the intravenous (IV) PK of a microtracer dose of [14C] OCA, and to evaluate the oral PK of OCA. In Part 1, subjects were administered the oral dose (Regimen A: 25 mg OCA tablet), followed by the IV microtracer dose (Regimen B: 100 μg [14C]-OCA) 1 hour 45 minutes after the oral dose administration. The 15 minute IV infusion ended at the estimated tmax for the oral dose (2 hours).

Figure 12:
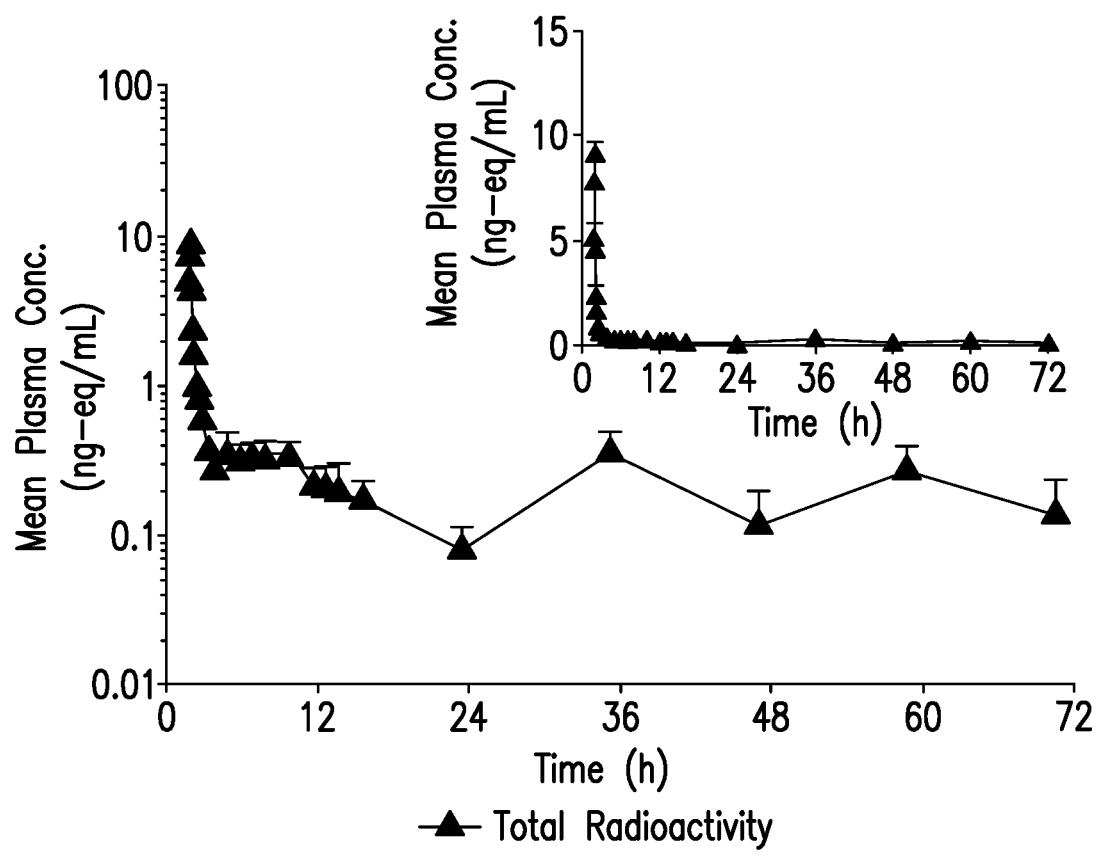
FIG. 12 is a graph showing Mean (SD) Plasma Concentrations of Total Radioactivity from 0 to 72 Hours Following IV 100 µg Microtracer Dose of [$^{14}$C] OCA, Log and Linear Scales, Part 1—PK Population (N=5).
Figure 13:
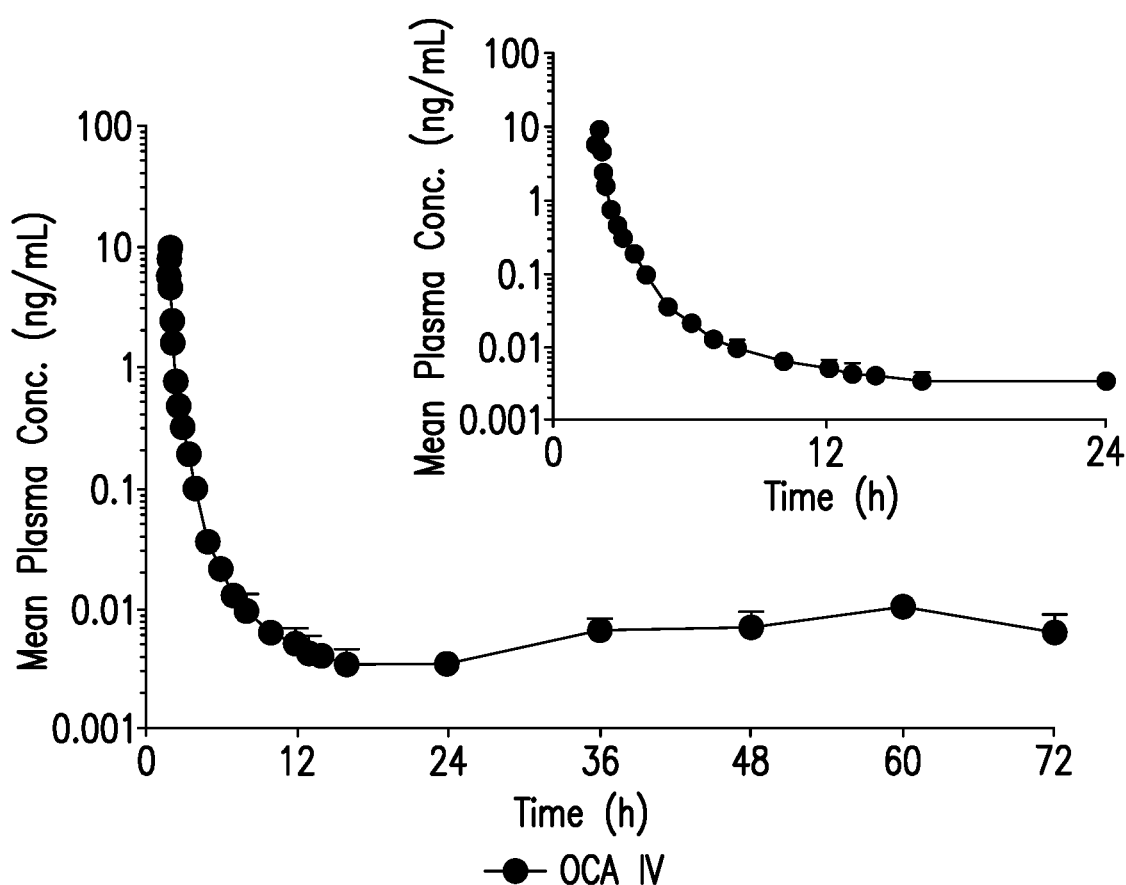
FIG. 13 is a graph showing Mean (SD) Plasma Concentrations of OCA from 0 to 72 and 0 to 24 Hours Following IV 100 µg Microtracer Dose of [$^{14}$C]-OCA, Log Scale, Part 1—PK Population (N=5).

Mean plasma concentrations of total radioactivity are shown in FIG. 12, and of [$^{14}$C]-OCA in FIG. 13. The highest concentration of radioactivity in plasma was measured after completion of the IV dose, and the concentrations of OCA declined rapidly within 4 hours. After the initial decline, a low-level, prolonged profile of OCA and total radioactivity was observed, as expected due to enterohepatic recirculation. Concentrations of total radioactivity demonstrated exposure peaks in measurements taken at 36 and 60 hours, likely due to the conjugates being released from the gallbladder following meals.

Pharmacokinetic parameters of [$^{14}$C]-OCA and total radioactivity are summarized in Table 4. The $AUC_{0-t}$ of [$^{14}$C]-OCA accounted for approximately 20% of the total radioactive exposure over 72 hours, indicating that the formation of OCA conjugates (glyco-OCA, tauro-OCA, and potentially other metabolites) accounted for the majority of the circulating radioactivity. Also, [$^{14}$C]-OCA showed a moderate clearance value and a relatively low volume of distribution.

TABLE 4

Mean (SD) of IV Plasma Pharmacokinetic Parameters: Regimen B, Study Part 1: PK Population (N = 5)

| | OCA Part 1 | |
|---|---|---|
| Parameter | IV [$^{14}$C]-OVA N = 5 | Total Radioactivity N = 5 |
| $C_{max}$ (ng/mL) | 9.71 (0.3279) | 9.13 (0.5512) |
| $AUC_{0-t}$ (hours*ng/mL) | 3.86 (0.1738) | 18.5 (4.234) |
| CL (L/hours) | 25.0 (1.052) | N/A |
| $V_s$ (L) | 618 (341.9) | N/A |
| $V_{ss}$ (L) | 210 (62.14) | N/A |

Figure 14:
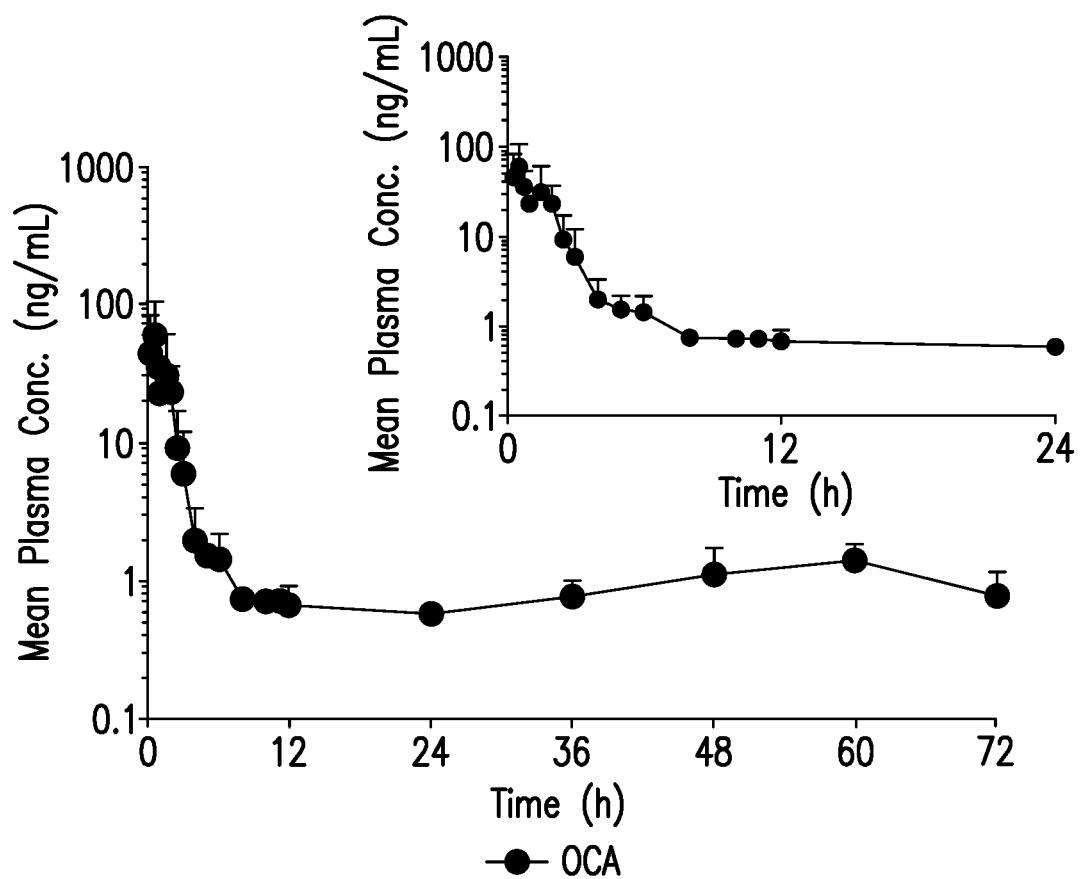
FIG. 14 is a graph showing Mean (SD) Plasma Concentrations of OCA from 0 to 24 and 0 to 72 Hours Following 25 mg Oral Dose of OCA, Log Scale, Part 1—PK Population (N=5).

$AUC_{0-t}$ = Area under the concentration versus time curve from time zero to the last sampling time with quantifiable analyte;
CL = total plasma clearance;
$C_{max}$ = Maximum observed analyte concentration in plasma;
IV = Intravenous;
N/A = Not applicable;
OCA = Obeticholic acid;
$V_{ss}$ = Volume of distribution at steady state;
$V_s$ = Volume of distribution;
Regimen B = 15 minute IV infusion of 100 μg [$^{14}$C]-OCA (b) Oral PK as Part of Absolute Bioavailability Assessment To evaluate the oral PK, plasma concentrations of OCA and its conjugates were measured following an oral dose (Regimen A: 25 mg OCA). Mean (SD) plasma concentrations over time of OCA are presented in FIG. 14 and PK parameters are presented in Table 5. OCA was rapidly absorbed; the median tmax was 0.5 hrs. Following Cmax, OCA concentration declined rapidly within 4 hours, consistent with the IV profile of OCA. Subsequent OCA concentrations remained, on average, less than 10% of Cmax up to 72 hours post-dose. A prolonged profile of OCA was observed over the course of 72 hours (FIG. 4). This low level persistence of parent OCA is most likely due to deconjugation of glyco-OCA and tauro-OCA by commensal bacteria in the ileum and colon, followed by reabsorption of OCA.

Figure 15:
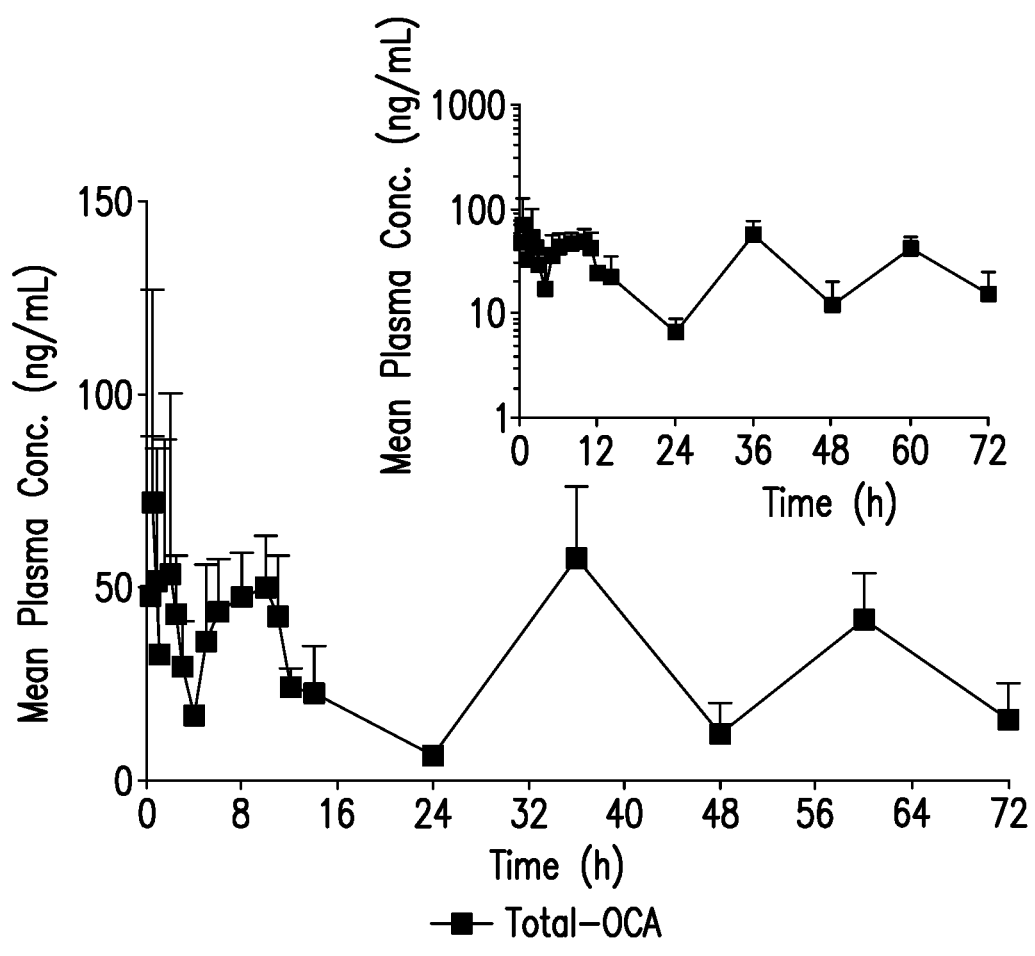
FIG. 15 is a graph showing Mean (SD) Plasma Concentrations of Total OCA from 0 to 72 Hours Following 25 mg Oral Dose of OCA, Linear and Log scales, Part 1—PK Population (N=5).

Mean (SD) plasma concentrations over time of total OCA (the sum of OCA, glyco-OCA, and tauro-OCA) are presented in FIG. 15 (Note: Total OCA calculated as sum of OCA, glyco-OCA, and tauro-OCA concentrations at each time point, glyco-OCA, and tauro-OCA concentrations at each time point expressed as mass equivalents of OCA). Pharmacokinetic parameters of OCA, glyco-OCA, tauro-OCA, and total OCA are summarized in Table 5. Consistent with the [$^{14}$C]-OCA results, the maximum exposure of total OCA occurred after a meal, consistent with gallbladder release and enterohepatic recirculation, leading to exposure levels being observed up to 72 hours post-dose. Based on overall exposure of total OCA ($AUC_{0-t}$), glyco-OCA and tauro-OCA are the primary components of exposure, with minimal contribution (less than 10%) from the parent (OCA).

TABLE 5

Mean (SD) Oral Plasma Pharmacokinetic Parameters (Regimen A, Study Part 1: PK Population (N = 5))

| Parameter | OCA Part 1 (N = 5) | | | |
|---|---|---|---|---|
| | OCA | Glyco-OCA | Tauro-OCA | Total OCA[a] |
| $t_{max}$ (h)[b] | 0.500 (0.50, 2.03) | 8.000 (2.00, 36.00) | 36.000 (2.00, 60.00) | 1.500 (0.50, 11.00) |
| $C_{max}$ (ng/mL) | 80.9 (26.41) | 57.4 (24.43) | 23.1 (7.412) | 105 (28.93) |
| $AUC_{0-t}$ (hours*ng/mL) | 144 (21.06) | 1540 (480.7) | 624 (159.6) | 1990 (525.6) |
| F (%) | 17.1 (2.993) | | | |

$AUC_{0-t}$ = Area under concentration versus time curve from time zero to the last sampling time with quantifiable analyte;
$C_{max}$ = Maximum observed analyte concentration in plasma;
F = Absolute bioavailability as determined by the ratio of dose normalized AUC for oral dose/dose normalized AUC for IV dose;
glyco-OCA = glycine conjugate of obeticholic acid;
OCA = obeticholic acid;
tauro-OCA = taurine conjugate of obeticholic acid;
$t_{max}$ = Time of maximum plasma concentration
[a]Total OCA calculated as sum OCA, glyco-OCA and tauro-OCA concentrations at each time point expressed as mass equlivants of OCA.
[b]Median and range.
Note:
Regimen A was a single oral dose of a 25 mg OCA tablet administered with 240 mL water.

Absolute bioavailability was determined by the ratio of dose normalized AUC for oral dose/dose normalized AUC for IV dose. As shown in Table 5, the mean absolute bioavailability (F) of OCA was approximately 17%. This relatively low value for bioavailability is consistent with the efficient uptake typical of bile acids into the liver, the primary site of action of OCA. PK results were as expected for a bile acid. OCA is rapidly absorbed in the intestine and taken up in the liver, where it is conjugated with glycine and taurine. Glyco-OCA and tauro-OCA were the primary components of exposure, with minimal contribution from the parent (OCA). Enterohepatic recirculation produced an extended profile, with maximum exposure occurring after meals.

The results from Part 1 (Absolutely Bioavailability) showed that the oral bioavailability of OCA is 17%. Following an oral dose of 25 mg OCA and an IV microtracer dose of 100 μg [$^{14}$C]-OCA, the concentrations of total radioactivity and of [$^{14}$C]-OCA declined rapidly within the first 4 hours, as the concentrations of the conjugates (glyco-OCA, and tauro-OCA) increased and persisted over 72 hours. Exposure of total OCA (sum of OCA, glyco-OCA, and tauro-OCA) peaked after meals, consistent with gallbladder release and enterohepatic recirculation. Taken together, these data indicate that OCA is rapidly absorbed in the intestine and taken up in the liver, where it is conjugated with glycine and taurine prior to excretion via the bile.

Mass Balance and Metabolite Identification (Absorption, Distribution, Metabolism, and Excretion of OCA (in Healthy Male Subjects)

Preclinical mass balance and radiolabeled single dose PK studies in the rat have examined biliary, urinary, and fecal excretion of OCA and its metabolites. These results revealed that the radioactivity derived from [$^{14}$C] OCA after a single oral administration was excreted mainly in the feces (due primarily to extensive biliary excretion), and excretion of OCA appears to be consistent with that of natural bile acids. This study sought to confirm the routes of elimination in humans.

The PK objectives of Part 2 were to assess the mass balance recovery from excreta after an oral dose of 25 mg [$^{14}$C]-OCA, and to assess the metabolite profile of [$^{14}$C]-OCA in plasma, urine, and fecal samples. Part 2 also evaluated the extent of distribution of total radioactivity into blood cells, and identified metabolites accounting for more than 10% of circulating total radioactivity.

(a) Oral Pharmacokinetics

Figure 16:
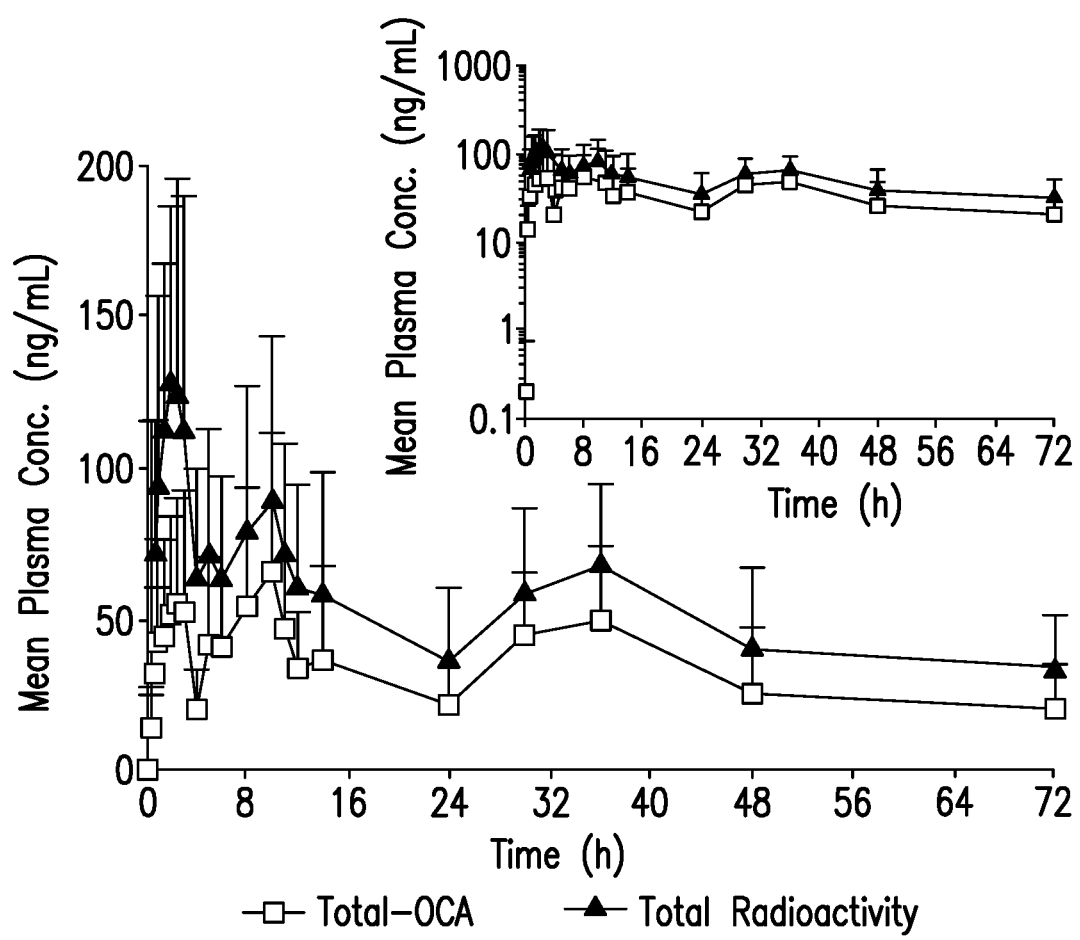
FIG. 16 is a graph showing Mean (SD) Plasma Concentrations of Total OCA and Total Radioactivity Following a 25 mg Oral Dose of [$^{14}$C]-OCA from 0 to 72 Hours, Linear and Log Scales, Part 2, PK Population (N=8).
Figure 17:
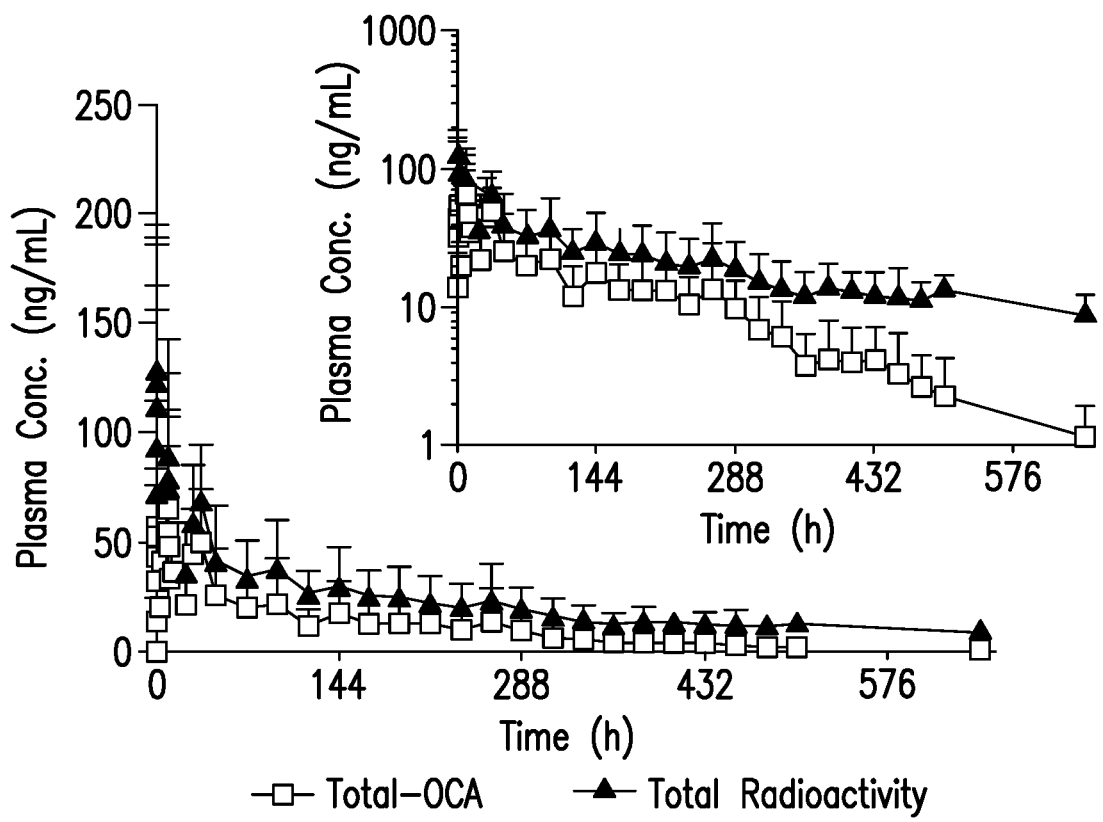
FIG. 17 is a graph showing Mean (SD) Plasma Concentrations of Total OCA and Total Radioactivity Following a 25 mg Oral Dose of [$^{14}$C]-OCA, 4-Week Sampling Period, Part 2, Linear and Log Scales, PK Population (N=8).

The concentrations of total radioactivity and total OCA in plasma over time are shown in FIG. 16 (Note: Total OCA calculated as sum of OCA, glyco-OCA, and tauro-OCA concentrations at each time point, glyco-OCA, and tauro-OCA concentrations at each time point expressed as mass equivalents of OCA) and FIG. 17 (Note: Total OCA calculated as sum of OCA, glyco-OCA, and tauro-OCA concentrations at each time point, glyco-OCA, and tauro-OCA concentrations at each time point expressed as mass equivalents of OCA. Units for total radioactivity are mass equivalent to OCA (i.e. ng-eq OCA/mL)). These concentrations differed by a consistent amount, which suggested the presence of circulating OCA metabolites other than glyco-OCA and tauro-OCA. Two additional OCA metabolites were identified: OCA-3 glucuronide and OCA-24 glucuronide, based on the metabolite profiling of radioactivity, mass spectrometry, and authentic standards for the glucuronide metabolites.

Pharmacokinetic parameters of OCA and its conjugates, and total radioactivity, are summarized in Table 6. Similar to the results observed in Part 1, OCA was rapidly absorbed; the median tmax was 1.25 hrs. Following Cmax, OCA concentration declined rapidly within the first 4 hours. The maximum exposure of total OCA, including the conjugates, occurred after meals, consistent with gallbladder release and enterohepatic recirculation, leading to exposure levels being observed over the approximately 4-week sampling period.

TABLE 6

Mean (SD) of Plasma Pharmacokinetic Parameters: Regimen C, Study Part 2: PK Population, (N = 8)

| | OCA Part 2 (N = 8) | | | | |
|---|---|---|---|---|---|
| Parameter | OCA | Glyco-OCA | Tauro-OCA | Total OCA[a] | Total Radioactivity in Plasma |
| $t_{max\ (h)}$[b] | 1.25 (0.750, 2.50) | 10.0 (3.00, 36.0) | 9.03 (2.50, 36.0) | 9.03 (0.750, 36.0) | 1.25 (0.750, 3.00) |
| $C_{max}$ (ng/mL) | 63.7 (19.07) | 73.8 (39.96) | 24.4 (14.21) | 97.8 (39.47) | 172 (45.86) |
| $AUC_{0-t}$ (hours*ng/mL) | 475 (215.5) | 4690 (2232) | 2550 (2155) | 6600 (3646) | 12700 (5151) |

$AUC_{0-t}$ = Area under concentration versus time curve from time zero to the last sampling time with quantifiable analyte;
$C_{max}$ = Maximum observed analyte concentration in plasma;
glyco-OCA = glycine conjugate of obeticholic acid;
OCA = obeticholic acid;
tauro-OCA = taurine conjugate of obeticholic acid;
$t_{max}$ = Time of maximum plasma concentration
Note:
Regimen C = a 25 mg Oral Dose of [14C]-OCA
[a]Total OCA calculated as sum OCA, glyco-OCA and tauro-OCA concentrations at each time point expressed as mass equlivants of OCA.
[b]Median and range.

(b) Mass Balance

Figure 18:
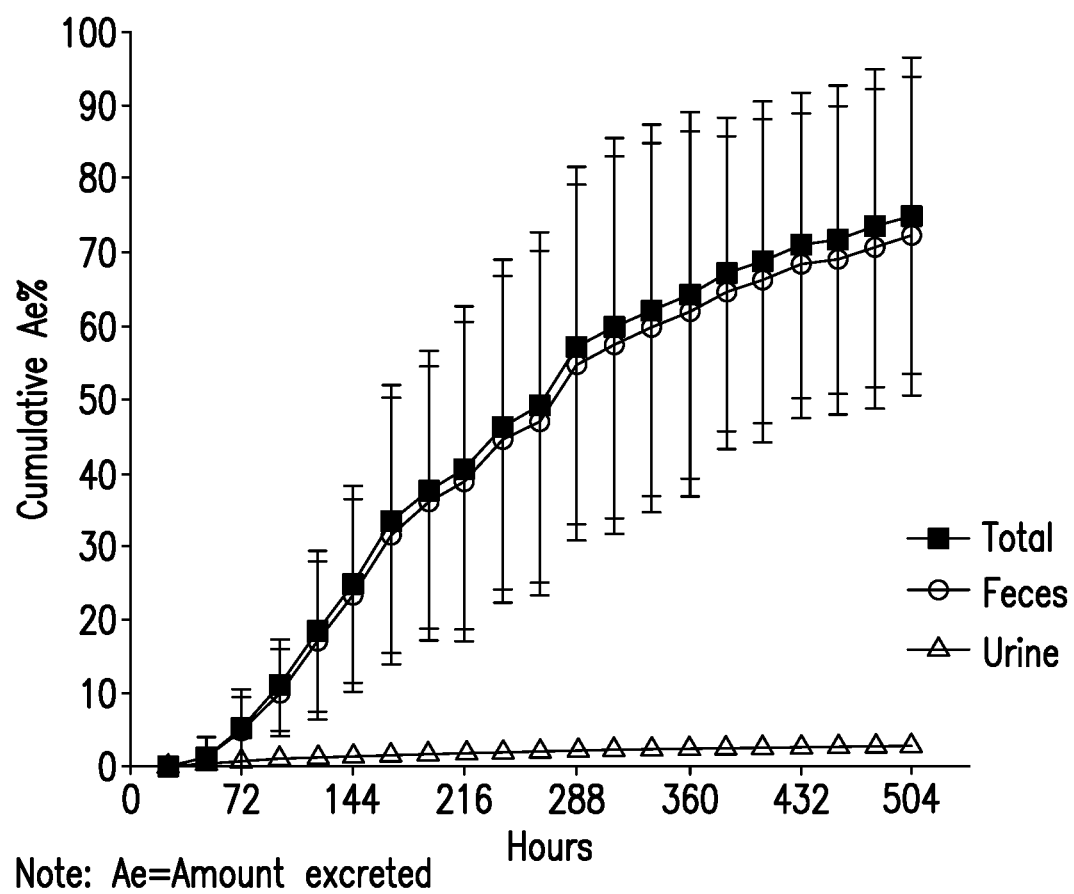
FIG. 18 is a graph showing Mean (SD) Cumulative Amount Excreted, Mass Balance of Urine, Fecal and Total Excretion and Recovery, Study Part 2, Mass Balance Population, (N=8).

The mean cumulative recovery (cumulative % Ae (Amount excreted)) of radioactivity in the urine and feces of subjects receiving oral [$^{14}$C]-OCA is shown in FIG. 18. Following a single oral dose of 25 mg [$^{14}$C]-OCA a mean of 75.1% (range between 28.3% and 97.5%) of the total radioactivity administered was recovered from urine and feces by the end of the inpatient sampling period (504 hours postdose). An average of 2.83% (range 1.57% to 4.00%) of the total radioactivity was recovered from the urine, and the majority of drug-related material in the urine was recovered within the first 312 hours after investigational product administration. An average of 72.3% (range 25.2% to 95.9%) was recovered from feces by 504 hours postdose. However, because only 1 subject had achieved a cumulative recovery of greater than 90% at 504 hours, the other 7 subjects conducted additional home fecal collections beyond 504 hours postdose (7/8 subjects until 816 hours, 3/8 subjects until 888 hours postdose and 2/8 subjects until 1152 hours postdose). Total recovery (urine and feces combined, sampled up to 1152 hours) from each of the subjects ranged from 76.31% to 111.28% of the administered radioactivity). At 1152 hours, a mean of 87.0% of the total radioactivity administered (range 73.2 to 107%) was recovered from feces. The majority of drug-related material in the feces was recovered within 552 hours of dosing with investigational product. In Part 2 (Mass Balance), the mass balance data confirmed that the primary elimination route of OCA is through the feces. A mean of 87% of administered radioactivity was recovered from the feces over the entire collection period, and a minor percentage (<3%) was recovered from the urine.

EQUIVALENTS

Those skilled in the art will recognize, or be able to ascertain, using no more than routine experimentation, numerous equivalents to the specific embodiments described specifically herein. Such equivalents are intended to be encompassed in the scope of the following claims.

The invention claimed is:

1. A compound of Formula I

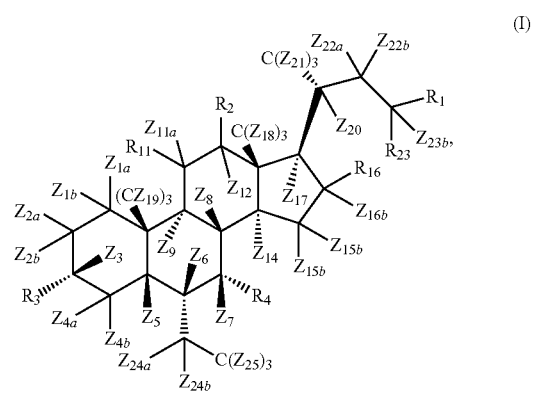

or a pharmaceutically acceptable salt thereof, wherein
$R_1$ is OH, glucuronide, $OSO_3H$, $SO_3H$, $C(O)R_6$, or $^{14}C(O)R_6$;
$R_2$ is hydrogen, deuterium, or OH;
$R_3$ is OH or glucuronide;
$R_4$ is OH or glucuronide;
$R_6$ is $NH(CH_2)_2SO_3H$, $NHCH_2CO_2H$, or $N(CH_3)CH_2CO_2H$ or glucuronide, wherein the hydrogen atoms in $R_6$ can be replaced with deuterium;
$R_{11}$ is $Z_{11b}$, hydroxy, halogen, or alkoxy, or oxo when $Z_{11a}$ is not present;
$R_{16}$ is $Z_{16a}$, hydroxy, halogen, or alkoxy, or oxo when $Z_{16b}$ is not present;
$R_{23}$ is $Z_{23a}$ or alkyl; and
$Z_{1a}$, $Z_{1b}$, $Z_{2a}$, $Z_{2b}$, $Z_3$, $Z_{4a}$, $Z_{4b}$, $Z_5$, $Z_6$, $Z_7$, $Z_8$, $Z_9$, $Z_{11a}$, $Z_{11b}$, $Z_{12}$, $Z_{14}$, $Z_{15a}$, $Z_{15b}$, $Z_{16a}$, $Z_{16b}$, $Z_{17}$, $Z_{18}$, $Z_{19}$, $Z_{20}$, $Z_{21}$, $Z_{22a}$, $Z_{22b}$, $Z_{23a}$, $Z_{23b}$, $Z_{24a}$, $Z_{24b}$, or $Z_{25}$ is independently hydrogen or deuterium, and at least one of $Z_{1a}$, $Z_{1b}$, $Z_{2a}$, $Z_{2b}$, $Z_3$, $Z_{4a}$, $Z_{4b}$, $Z_5$, $Z_6$, $Z_7$, $Z_8$, $Z_9$, $Z_{11a}$, $Z_{11b}$, $Z_{12}$, $Z_{14}$, $Z_{15a}$, $Z_{15b}$, $Z_{16a}$, $Z_{16b}$, $Z_{17}$, $Z_{18}$, $Z_{19}$, $Z_{20}$, $Z_{21}$, $Z_{22a}$, $Z_{22b}$, $Z_{23a}$, $Z_{23b}$, $Z_{24a}$, $Z_{24b}$, or $Z_{25}$ is deuterium; and
any carbon atom is $^{12}C$, $^{13}C$, or $^{14}C$.

2. The compound of claim 1, wherein the compound of Formula I is a compound of Formula II (II)

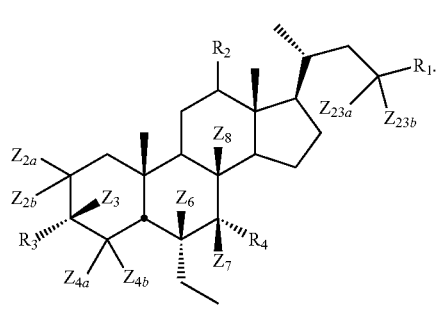

3. The compound of claim 1, wherein the compound of Formula I is a compound of Formula III (III)

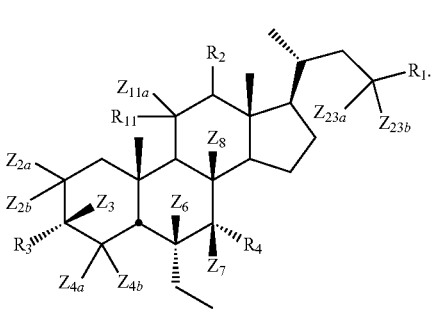

4. The compound of claim 1, wherein the compound of Formula I is a compound of Formula IV (IV)

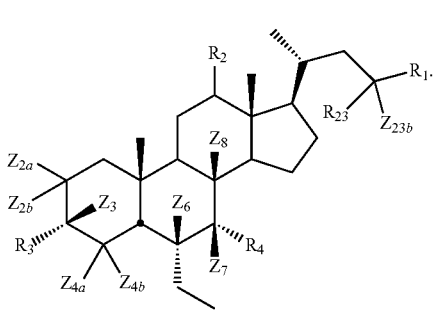

5. The compound of claim 1, wherein the compound of Formula I is a compound of Formula V (V)

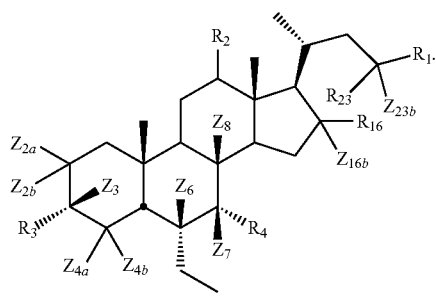

6. The compound of claim 1, wherein the compound of Formula I is a compound of Formula VI (VI)

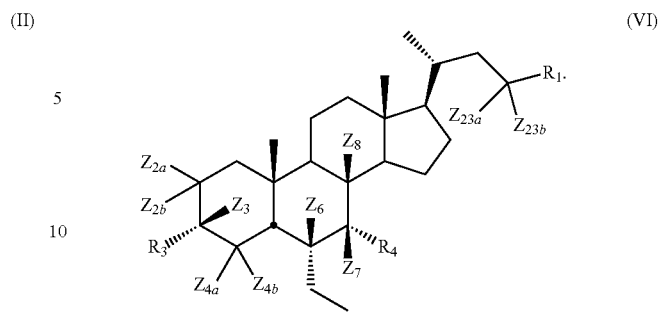

7. The compound of claim 1, wherein the compound of Formula I is a compound of Formula VII (VII)

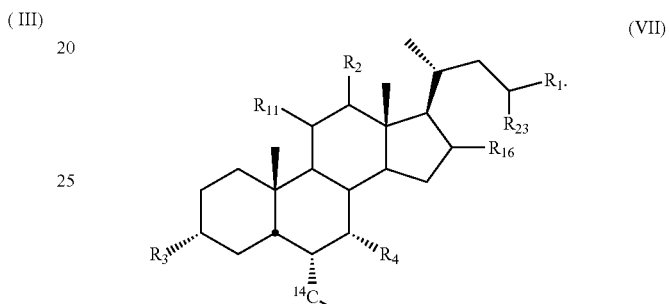

8. The compound of claim 1, wherein the compound of Formula I is a compound of Formula VIII (VIII)

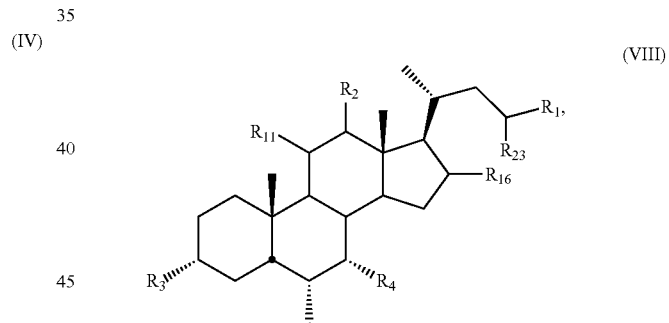

wherein $R_1$ is $^{14}C(O)R_6$.

9. The compound of claim 1, wherein $R_2$ is hydrogen.

10. The compound of claim 1, wherein the compound is selected from

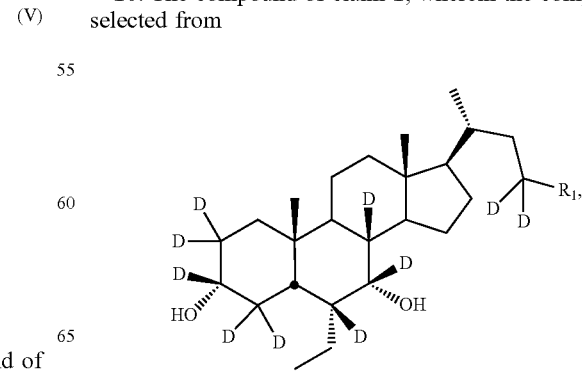

-continued
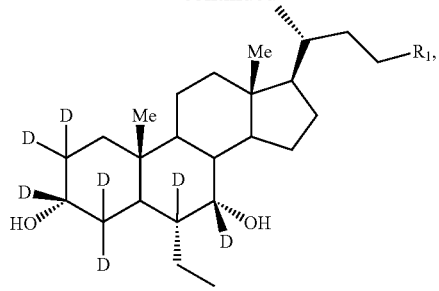
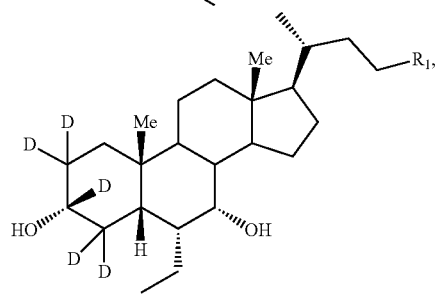
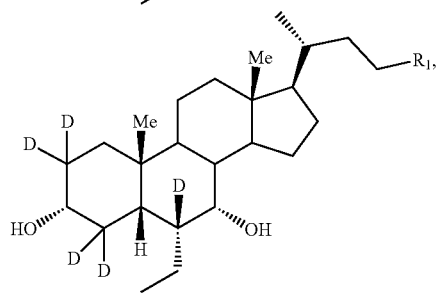
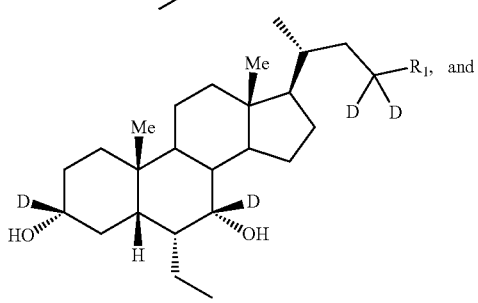
-continued
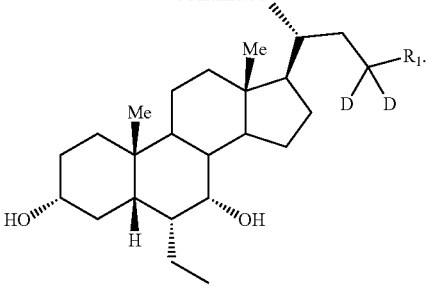
11. The compound of claim 1, wherein $R_1$ is $C(O)R_6$.
12. The compound of claim 1, wherein $R_1$ is $^{14}C(O)R_6$.
13. The compound of claim 1, wherein $R_6$ is $NH(CH_2)_2 SO_3H$, $NHCH_2CO_2H$, or $N(CH_3)CH_2CO_2H$.
14. The compound of claim 1, wherein $R_3$ is glucuronide.
15. The compound of claim 1, wherein the compound is
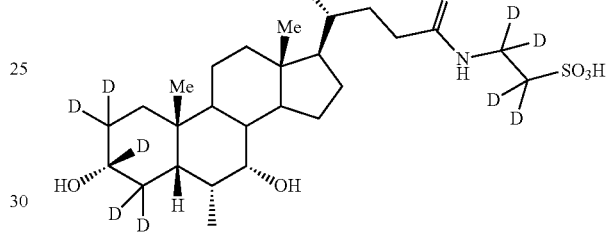
or
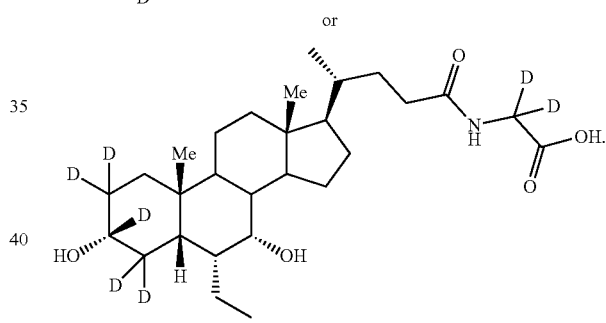
* * * * *